(12) United States Patent
Weterings et al.

(10) Patent No.: US 12,054,471 B2
(45) Date of Patent: Aug. 6, 2024

(54) THIOCYCLOHEPTYNE DERIVATIVES AND THEIR USE

(71) Applicant: Cristal Delivery B.V., Maastricht (NL)

(72) Inventors: Josephus Johannes Weterings, Maastricht (NL); Cristianne Johanna Ferdinand Rijcken, Maastricht (NL)

(73) Assignee: Cristal Delivery B.V., Maastricht (NL)

( * ) Notice: Subject to any disclaimer, the term of this patent is extended or adjusted under 35 U.S.C. 154(b) by 637 days.

(21) Appl. No.: 17/260,210

(22) PCT Filed: Jul. 12, 2019

(86) PCT No.: PCT/NL2019/050438
§ 371 (c)(1),
(2) Date: Jan. 13, 2021

(87) PCT Pub. No.: WO2020/013696
PCT Pub. Date: Jan. 16, 2020

(65) Prior Publication Data
US 2021/0395216 A1    Dec. 23, 2021

(30) Foreign Application Priority Data
Jul. 13, 2018 (EP) .................................... 18183537

(51) Int. Cl.
| | | |
|---|---|---|
| C07D 337/04 | (2006.01) |
| A61K 47/61 | (2017.01) |
| A61K 47/62 | (2017.01) |
| A61K 47/69 | (2017.01) |
| C07D 409/12 | (2006.01) |
| C07D 495/04 | (2006.01) |
| C08F 12/30 | (2006.01) |

(52) U.S. Cl.
CPC ............ *C07D 337/04* (2013.01); *A61K 47/61* (2017.08); *A61K 47/62* (2017.08); *A61K 47/6929* (2017.08); *C07D 409/12* (2013.01); *C07D 495/04* (2013.01); *C08F 12/30* (2013.01)

(58) Field of Classification Search
CPC ...... A61K 47/545; A61K 47/58; A61K 47/61; A61K 47/62; A61K 47/6907; A61K 47/6929; C07D 333/04; C07D 333/06; C07D 333/08; C07D 337/04; C07D 409/12; C07D 495/04; G01N 33/5432; C08F 12/30
See application file for complete search history.

(56) References Cited

PUBLICATIONS

Schulte et al. (Metallorganische Verbindungen des Kupfers XVI. . . .,Journal of Organometallic Chemistry, vol. 584, pp. 1-10, Published 1999) (Year: 1999).*

Li et al. "Development and Applications of the Copper-Catalyzed Azide-Alkyne Cycloaddition (CuAAC) as a Bioorthogonal Reaction" Molecules 2016, 21, 1393; doi:10.3390/molecules21101393.

* cited by examiner

*Primary Examiner* — Yevgeny Valenrod
*Assistant Examiner* — Blaine G Doletski
(74) *Attorney, Agent, or Firm* — Banner & Witcoff, Ltd.

(57) ABSTRACT

The present invention pertains to novel thiocycloheptyne derivatives of general formula (I): and in particular to thiacycloalkynesulfoimine derivatives and their synthesis. The invention also relates to the use of the novel thiocycloheptyne derivatives in coupling reactions with linkers and drugs. The invention further relates to the use of the novel thiocycloheptynes in bioorthogonal (copper-free) click reactions. The invention further pertains to the use of the novel thiocycloheptyne derivatives in the generation of advanced multifunctional drug delivery systems (drug-loaded) nanoparticles.

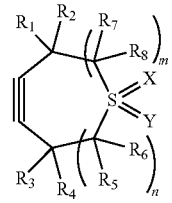

21 Claims, 56 Drawing Sheets

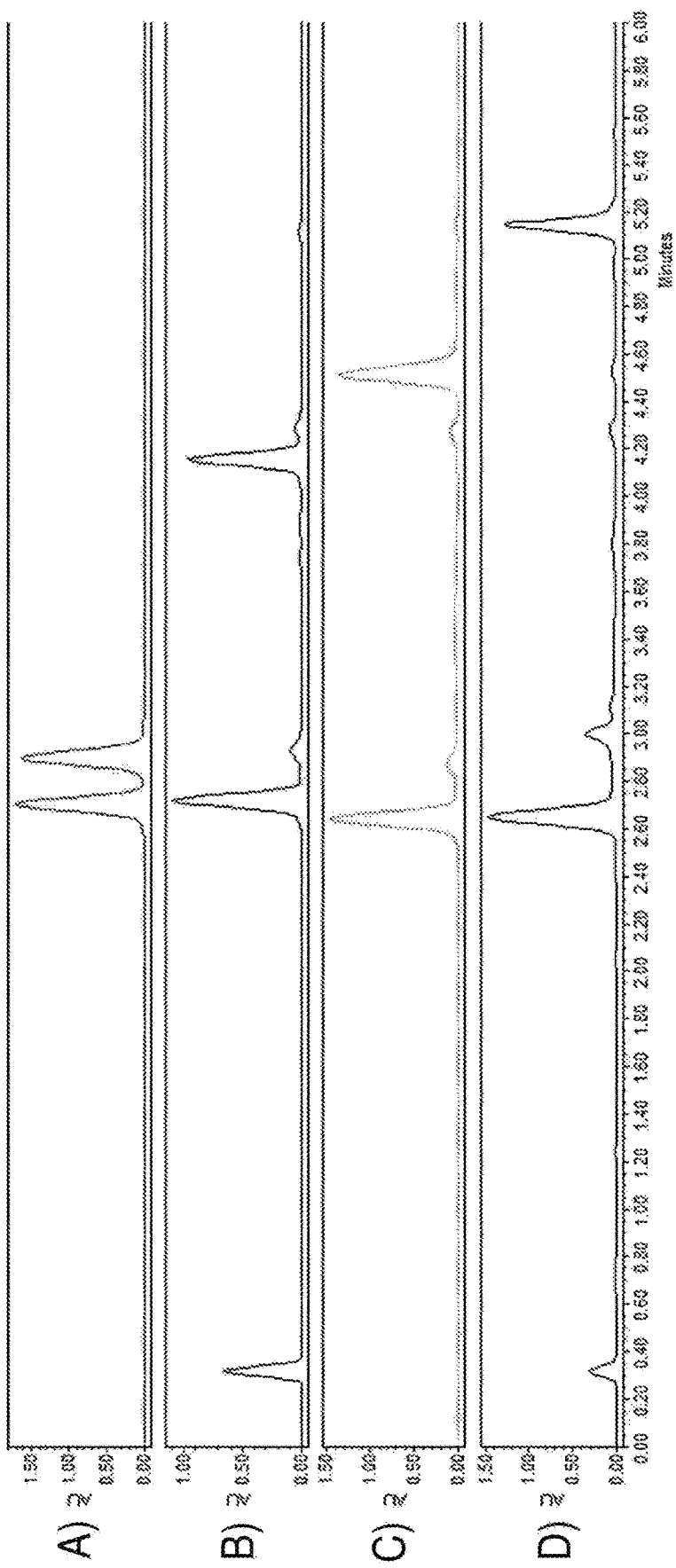
FIG. 56A-D

THIOCYCLOHEPTYNE DERIVATIVES AND THEIR USE

CROSS-REFERENCE TO RELATED APPLICATIONS

This application is the national phase of PCT application PCT/NL2019/050438 having an international filing date of Jul. 12, 2019, and published as WO 2020/013696 on Jan. 16, 2020, which claims benefit of European patent application No. 18183537.2 filed Jul. 13, 2018. The contents of the above patent applications are incorporated by reference herein in their entireties.

FIELD OF THE INVENTION

The present invention pertains to novel thiocycloheptyne derivatives, in particular thiacycloalkynesulfoimine derivatives and their synthesis. The invention also relates to the use of the novel thiocycloheptyne derivatives in various coupling reactions such as those involving linkers, drugs and drug delivery systems, proteins, imaging agents, dyes, chromophores, ligands etc. The invention further relates to the use of the novel thiocycloheptynes in copper-free click reactions. The invention further pertains to the use of the novel thiocycloheptyne derivatives in the generation of a wide variety of systems such as targeted and/or labelled delivery systems like nanoparticles, proteins, hydrogels, liposomes, antibody-drug conjugates, drug polymer conjugates etc.

BACKGROUND OF THE INVENTION

Bioorthogonal chemistry is used in the investigation of biomolecules and physiological processes. Bioorthogonal chemistry can be used when other, more conventional research tools or medical treatment are not available or inadequate. Typically, a protocol starts by labelling a target biomolecule in cells or live organisms with a bioorthogonal functional group. A probe molecule bearing complementary functionality is provided to the system and the bioorthogonal chemical reaction delivers the probe specifically to the targets of interest. Kinetic optimization and yield optimization, e.g. by enabling easier purification, are seen as a key factor in the further development of this useful approach. In the past, the strain-promoted cycloaddition reaction of azides and cyclooctynes has been found as a well-tolerated bioorthogonal reaction. The strain-promoted cycloaddition reaction of azides and cyclooctynes, also called Cu-free (or copper-free) click chemistry was inspired by the classic work of Krebs and Kimling in the 1970s. They observed that, in contrast to unactivated linear alkynes, which undergo 1,3-dipolar cycloaddition with azides only at elevated temperatures, cyclooctyne readily reacts with the same substrates at room temperature. The heightened reactivity of cyclooctyne was attributed to the ring strain resulting from deformation of the bond angles of the alkyne.

Almeida et al. have described a group of cyclooctynes that have been developed over the years and used in the biorthogonal coupling reactions. Almeida investigated the effect of an endocyclic sulfur on the cyclooctyne activity and synthesized a number of thiocycloalkynes. It was found that the reactivity of 3,3,6,6-tetramethylthiacycloheptyne (TMTH) in the cycloaddition reaction was faster than the previous cyclooctyne compounds. King et al (Chem Commun 2102, 48, 9308) described a reasonable stability for TMTH only when derivatised at the sulphur atom with benzyl bromides. It was further found that other derivatives of TMTH were difficult to synthesize and the sulphur was difficult to derivatize further. Dommerholt et al. (NATURE COMMUNICATIONS 2014, 5, 5378, Top Curr (limn (Z) 2016, 374:16) indicated that TMTH suffers from poor stability and cannot be isolated in pure form. Li et al. (Molecules, 2016, 21, 1393) indicated that TMTH was the fastest SPAAC so far reported, but could not be equipped with a label which hampers the application in bioorthogonal reactions.

With the advantages of TMTH in the copper-free click reaction, there is a need for more compounds that are novel, readily accessible and reactive and that at least have the same reactivity in 1,3 dipolar cycloadditions with azides, and other 1,3 dipoles for use in copper-free click reactions.

SUMMARY OF THE INVENTION

The present inventors have found a novel class of sulphur containing cycloalkynes, in particular thiocycloheptynes. The cycloalkynes of the invention form a novel class of compounds that can be used for a wired variety of purposes, one of which is that they are reactive in copper-free click chemistry.

In a first aspect the invention relates to a Compound of Formula (I)

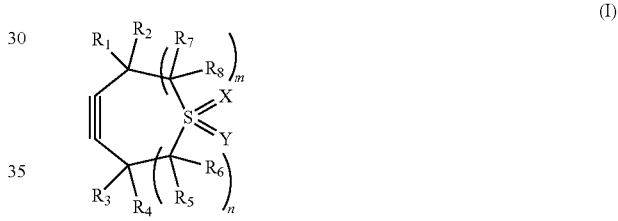

wherein:
n and m are independently 0, 1, or 2 and n+m is 2;
X is O or $NR^9$,
Y is $NR^{10}$,
$R^1$, $R^2$, $R^3$, $R^4$ are independently selected from the group consisting of hydrogen, halogen (F, CL, Br, I), O, N, P and S, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, wherein the O, N, P, and S are further independently coupled to hydrogen, halogen (F, CL, Br, I), $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, the alkyl groups optionally being interrupted by one of more hetero-atoms selected from the group consisting of O, N, P and S, wherein the alkyl groups, (hetero)aryl groups, alkyl(hetero)aryl groups and (hetero)arylalkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, CL, Br, I), amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S, wherein the silyl groups are represented by the formula $(R^{11})_3Si—$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S;

$R^5$, $R^6$, $R^7$, $R^8$ are independently selected from the group consisting of hydrogen, halogen (F, CL, Br, I), O, N, P and S, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, wherein the O, N, P, and S are further independently coupled to hydrogen, halogen (F, CL, Br, I), $C_3$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, the alkyl groups optionally being interrupted by one of more hetero-atoms selected from the group consisting of O, N, P and S, wherein the alkyl groups, (hetero)aryl groups, alkyl(hetero)aryl groups and (hetero)arylalkyl groups are independently optionally substituted with one or more substituents independently selected from the group consisting of $C_2$-$C_{12}$ alkyl groups, $C_2$-$C_{12}$ alkenyl groups, $C_2$-$C_{12}$ alkynyl groups, $C_1$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, CL, Br, I), amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S, wherein the silyl groups are represented by the formula $(R^{11})_3Si—$, wherein RH is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_3$-$C_{12}$ alkoxy groups, $C_2$-$C_{12}$ alkenyloxy groups, $C_1$-$C_{12}$ cycloalkyloxy groups, $C_2$-$C_{12}$ alkynyloxy groups and $C_1$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S;

wherein, optionally, R1 and R7, R1 with R8, R2 with R7, R2 with R8, R3 with R5, R3 with R6, R4 with R5, and/or R4 with R6 independently form fused ring systems such as cycloalkyl-, cyclo(hetero)aryl-, cycloalkyl(hetero)aryl, -cyclo(hetero)arylalkyl systems, wherein the alkyl groups of the fused ring systems optionally being interrupted by one or more hetero-atoms selected from the group consisting of O, N, P and S, wherein the alkyl groups, (hetero)aryl groups, alkyl(hetero)aryl groups and (hetero)arylalkyl groups of the fused systems are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S, wherein the silyl groups are represented by the formula $(R^{11})_3Si—$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S;

$R^9$, $R^{10}$ are independently selected from the group consisting of hydrogen, halogen (F, CL, Br, I), $R^{12}$, —CH=C$(R^{12})_2$, —C≡CR$^{12}$, —[C$(R^{12})_2$C$(R^{12})_2$O]$_q$—R$^{12}$, wherein q is in the range of 1 to 200, —CN, —N$_3$, —NCX, —XCN, —XR$^{12}$, —N$(R^{12})_2$, —$^+$N$(R^{12})_3$, —C(X)N$(R^{12})_2$, —C$(R^{12})_2$XR$^{12}$, —C(X)R$^{12}$, —C(X)XR$^{12}$, —S(O)R$^{12}$, —S(O)$_2$R$^{12}$, —S(O)OR$^{12}$, —S(O)$_2$OR$^{12}$, —S(O)N$(R^{12})_2$, —S(O)$_2$N$(R^{12})_2$, —OS(O)R$^{12}$, —OS(O)$_2$R$^{12}$, —OS(O)OR$^{12}$, —OS(O)$_2$OR$^{12}$, —P(O)$(R^{12})$(OR$^{12}$), —P(O)(OR$^{12}$)$_2$, —OP(O)(OR$^{12}$)$_2$, —Si$(R^{12})_3$, —XC(X)R$^{12}$, —XC(X)XR$^{12}$, —XC(X)N$(R^{12})_2$, —N$(R^{12})$C(X)R$^{12}$, —N$(R^{12})$C(X)XR$^{12}$ and —N$(R^{12})$C(X)N$(R^{12})_2$, wherein X is oxygen or sulphur and wherein $R^{12}$ is independently selected from the group consisting of hydrogen, halogen (F, CL, Br, I), $C_7$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups.

In a second aspect the invention relates to a method for the preparation of a compound of Formula (I the method comprising the steps of:

a. converting bishydrazone (2) to an iminodidehydrosulfonimino (3);

b. isolating the resulting an iminodidehydrosulfonimino (3).

In a third aspect the invention relates to a compound wherein X and/or Y and/or one of the atoms in the thiocycloheptyne ring adjacent to the S atom of a compound of Formula (I), independently, are coupled to an optional linking group (L) and a functional group (Q) to yield a compound of Formula (III):

(Formula I)-L-Q                                    (III)

wherein the linking group (L) is absent or selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_5$-$C_{24}$ cycloalkynylene groups, $C_7$-$C_{24}$ alkyl(hetero)arylene groups, $C_7$-$C_{24}$ (hetero)arylalkylene groups, $C_5$-$C_{24}$ (hetero)arylalkenylene groups, $C_9$-$C_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_5$-$C_{12}$ cycloalkynyl groups, $C_5$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, CL, Br, I), amino groups, oxo and silyl groups, wherein the silyl groups can be represented by the formula $(R^{11})_3Si-$, wherein $R^{11}$ is defined as above;

wherein the functional group Q is selected from the group consisting of hydrogen, halogen (F, CL, Br, I), $R^{12}$, $-CH=C(R^{12})_2$, $-C\equiv CR^{12}$, $-[C(R^{12})_2C(R^{12})_2O]_q-R^{12}$, wherein q is in the range of 1 to 200, $-CN$, $-N_3$, $-NCX$, $-XCN$, $-NR^{12}$, $-N(R^{12})_2$, $-^+N(R^{12})_3$, $-C(X)N(R^{12})_2$, $-C(R^{12})_2XR^{12}$, $-C(X)R^{12}$, $-C(X)XR^{12}$, $-S(O)_2R^{12}$, $-S(O)OR^{12}$, $-S(O)_2OR^{12}$, $-S(O)N(R^{12})_2$, $-S(O)_2N(R^{12})_2$, $-OS(O)R^{12}$, $-OS(O)_2R^{12}$, $-OS(O)OR^{12}$, $-OS(O)_2OR^{12}$, $-P(O)(R^{12})(OR^{12})$, $-P(O)(OR^{12})_2$, $-OP(O)(OR^{12})_2$, $-Si(R^{12})_3$, $-XC(X)R^{12}$, $-XC(X)XR^{12}$, $-XC(X)N(R^{12})_2$, $-N(R^{12})C(X)R^{12}$, $-N(R^{12})C(X)XR^{12}$ and $-N(R^{12})C(X)N(R^{12})_2$, wherein X is oxygen or sulphur and wherein $R^{12}$ is independently selected from the group consisting of hydrogen, halogen (F, CL, Br, I), $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups.

In a further aspect the invention provides a compound comprising a compound of formula (I) according to the invention coupled to an optional linking group (L) and a functional group (Q) at atom X, Y and/or at one of the atoms in the thiocycloheptyne ring adjacent to the S atom, preferably Y to yield a compound of Formula (III):

(Formula I)-L-Q          (III), wherein L and Q are as defined herein above.

In a further aspect the invention relates to a method for coupling a compound of formula (I) or (III) with a compound comprising a 1,3-dipole or a 1,3-(hetero)diene, preferably wherein the compound comprising a 1,3-dipole or a 1,3-(hetero)diene is an azide-comprising compound, a nitrone-comprising compound or a nitrile oxide comprising compound, preferably an azide-comprising compound. The coupling of the compounds of the invention with an azide typically leads to a triazole. The compound comprising a 1,3-dipole or a 1,3-(hetero)diene preferably comprises a drug, an antibody, a protein, a peptide, a ligand, an imaging label, a targeting ligand, a delivery agent, a nanoparticle and/or a carrier.

In a further aspect, the invention relates to a compound comprising a compound of formula (III) as defined herein, wherein functional group Q is reacted with a molecule of interest, preferably a molecule of interest selected from the group consisting of a drug, an antibody, a protein, a peptide, a ligand, an imaging label, a targeting ligand, a delivery agent, a nanoparticle and a carrier.

In a further aspect the invention relates to the method for the preparation of a wide variety of systems such as targeted and/or labelled delivery systems like nanoparticles, proteins, hydrogels, liposomes, antibody-drug conjugates, drug polymer conjugates etc. wherein a (functionalised) compound of Formula (I) or (III) is coupled to an azide.

In a further aspect the invention relates to the use of a compound of formula (I) or (III) in a method for the coupling two molecules of interest, more in particular of targeted and/or labelled delivery systems like nanoparticles, proteins, hydrogels, liposomes, antibody-drug conjugates, drug polymer conjugates using a copper free click reaction to one or more of a drug, an antibody, a protein, a peptide, a ligand, a imaging label, a targeting ligand, a delivery agent, a nanoparticle, and a carrier.

Other aspects comprise a method for the preparation of a construct comprising a nanoparticle and an active compound selected from the group of a drug, an antibody, a protein, a peptide, a ligand, a imaging label, a targeting ligand, a delivery agent, a nanoparticle, and a carrier, wherein the coupling on the nanoparticle and the active compounds comprises the coupling of a compound of formula I or III with an azide-containing compound to form a triazole compound.

In a further aspect the invention relates to the use of a compound according to the invention in a method for coupling two molecules of interest wherein optionally, the molecules are independently selected from amongst a drug, an antibody, a protein, a peptide, a ligand, a imaging label, a targeting ligand, a delivery agent, a nanoparticle, and a carrier. Preferably one of the molecules of interest comprises a cycloalkyne according to the invention and the other molecule of interest is a compound comprising a 1,3-dipole or a 1,3-(hetero)diene, preferably an azide, a nitrone-comprising or a nitrile oxide, more preferably an azide. The compound comprising a 1,3-dipole or a 1,3-(hetero)diene preferably comprises a drug, an antibody, a protein, a peptide, a ligand, an imaging label, a targeting ligand, a delivery agent, a nanoparticle and/or a carrier.

In a further aspect, the invention relates to a compound of Formula (I) as defined herein, wherein the alkyne group is coupled to a compound comprising a 1,3-dipole or a 1,3-(hetero)diene wherein preferably the compound comprising a 1,3-dipole or a 1,3-(hetero)diene is an azide-comprising compound, a nitrone-comprising compound or a nitrile oxide comprising compound, more preferably an azide-comprising compound and the azide-alkyne coupling preferably results in the formation of a triazole compound. The compound comprising a 1,3-dipole or a 1,3-(hetero)diene preferably comprises a drug, an antibody, a protein, a peptide, a ligand, an imaging label, a targeting ligand, a delivery agent, a nanoparticle and/or a carrier.

In a further aspect, the invention relates to a compound comprising a compound of Formula (I) as defined herein coupled to a compound comprising a 1,3-dipole or a 1,3-(hetero)diene, wherein the alkyne group of the thiocycloheptyne of Formula (I) is coupled to the compound comprising a 1,3-dipole or a 1,3-(hetero)diene, wherein preferably the compound comprising a 1,3-dipole or a 1,3-(hetero)diene is an azide-comprising compound, a nitrone-comprising compound or a nitrile oxide comprising compound, more preferably an azide-comprising compound and the azide-alkyne coupling preferably results in the formation of a triazole compound. The compound comprising a 1,3-dipole or a 1,3-(hetero)diene preferably comprises a drug, an antibody, a protein, a peptide, a ligand, an imaging label, a targeting ligand, a delivery agent, a nanoparticle and/or a carrier.

In a further aspect the invention relates to the use of a compound according to the invention in a bioorthogonal, optional copper-free, click reaction. Preferably the compound according to the invention is coupled to a compound comprising a 1,3-dipole or a 1,3-(hetero)diene, preferably an azide, a nitrone-comprising or a nitrile oxide, more preferably an azide. The compound comprising a 1,3-dipole or a 1,3-(hetero)diene preferably comprises a drug, an antibody, a protein, a peptide, a ligand, an imaging label, a targeting ligand, a delivery agent, a nanoparticle and/or a carrier.

In a further aspect the invention relates to the use of a compound according to the invention in a method for the coupling of a nanoparticle using a copper free click reaction to one or more of a drug, an antibody, a protein, a peptide, a ligand, a imaging label, a targeting ligand, a delivery agent, a nanoparticle, and a carrier.

Preferably the nanoparticle comprises a cycloalkyne compound according to the invention and the drug, antibody, protein, peptide, ligand, imaging label, targeting ligand, delivery agent, nanoparticle, or carrier comprises a 1,3-dipole or a 1,3-(hetero)diene, preferably an azide, a nitrone-comprising or a nitrile oxide, more preferably an azide. Alternatively the drug, antibody, protein, peptide, ligand, imaging label, targeting ligand, delivery agent, nanoparticle, or carrier comprises cycloalkyne compound according to the invention and the nanoparticle comprises a 1,3-dipole or a 1,3-(hetero)diene, preferably an azide, a nitrone-comprising or a nitrile oxide, more preferably an azide.

DESCRIPTION OF THE DRAWINGS

FIG. 17.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=3.5 min 98% A, t=3 min 98% A. Post time: 1.3 min. Detection: DAD (220-320 nm, 210 and 220 nm) Detection PDA (210-320 nm). Detection: MSD ESI pos/neg (mass range 100-1000).

Figure 19:
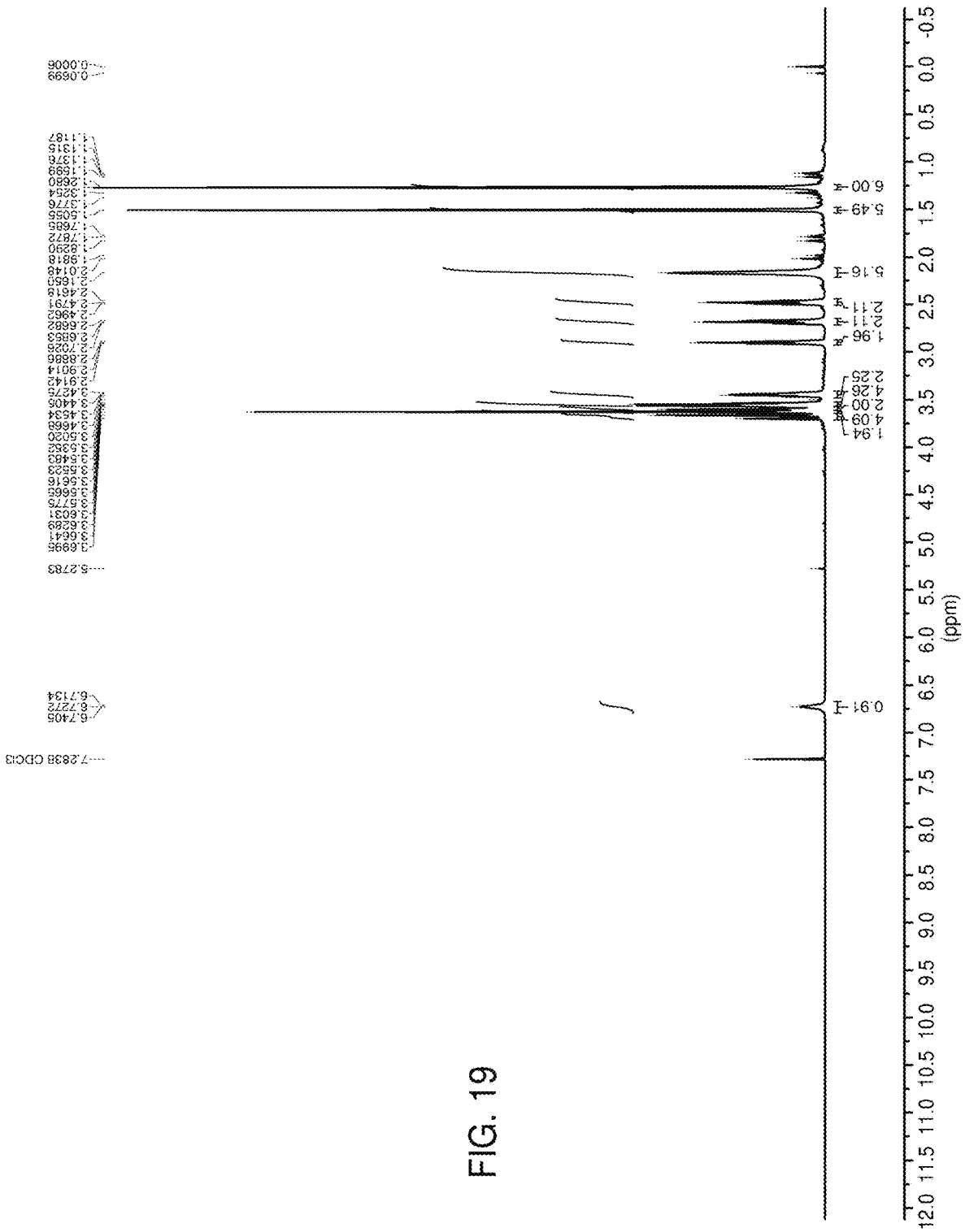

FIG. 19: [Example 11 Compound 11] NMR data of $N^1$-(2-(2-(2-aminoethoxy)ethoxy)ethyl)-$N^4$-(3,3,6,6-tetramethyl-1-oxido-4,5-didehydro-2,3,6,7-tetrahydro-1$\lambda^6$-thiepan-1-ylidene)succinamide.

Bruker BioSpin GmbH; Method Pulse Sequence: zg30. Relaxation Delay: 1 s. Solvent: CDCl$_3$. Temperature: ~298.9557 K. Number of Scans: 16. Frequency 400.132470966543 MHz. Nucleus: 1H.

Figure 20:
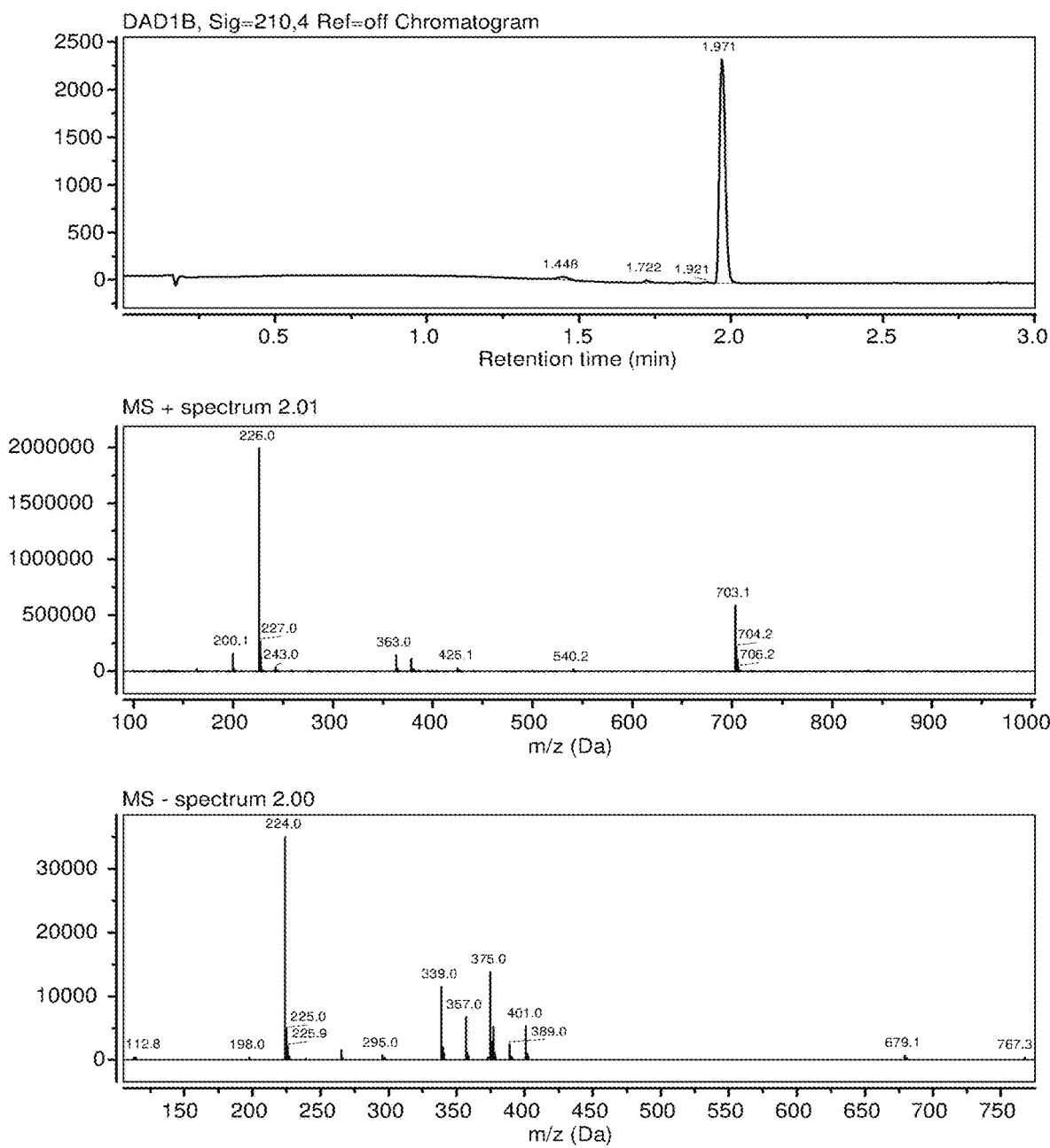

FIG. 20: [Example 12 Compound 12] LCMS and Mass data of 2,5-dioxopyrrolidin-1-yl (3,3,6,6-tetramethyl-1-oxido-4,5-didehydro-2,3,6,7-tetrahydro-1$\lambda^6$-thiepan-1-ylidene)carbamate.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 21:
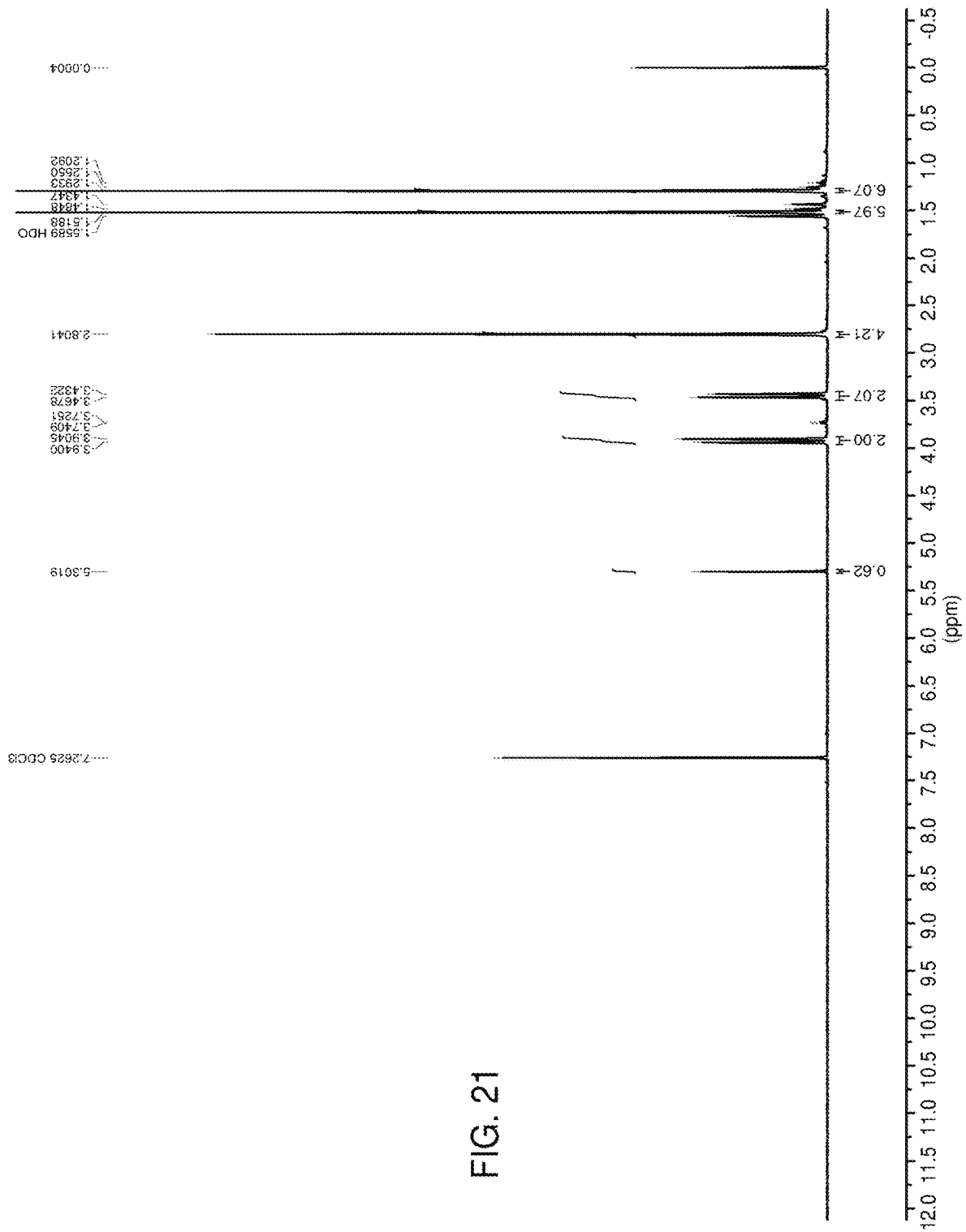

FIG. 21: [Example 12 Compound 12] NMR data of 2,5-dioxopyrrolidin-1-yl (3,3,6,6-tetramethyl-1-oxido-4,5-didehydro-2,3,6,7-tetrahydro-1$\lambda^6$-thiepan-1-ylidene)carbamate.

Bruker BioSpin GmbH; Method Pulse Sequence: zg30. Relaxation Delay: 1 s. Solvent: CDCl$_3$. Temperature: ~298.8484 K. Number of Scans: 16. Frequency: 400.132470966543 MHz. Nucleus: 1H.

Figure 22:
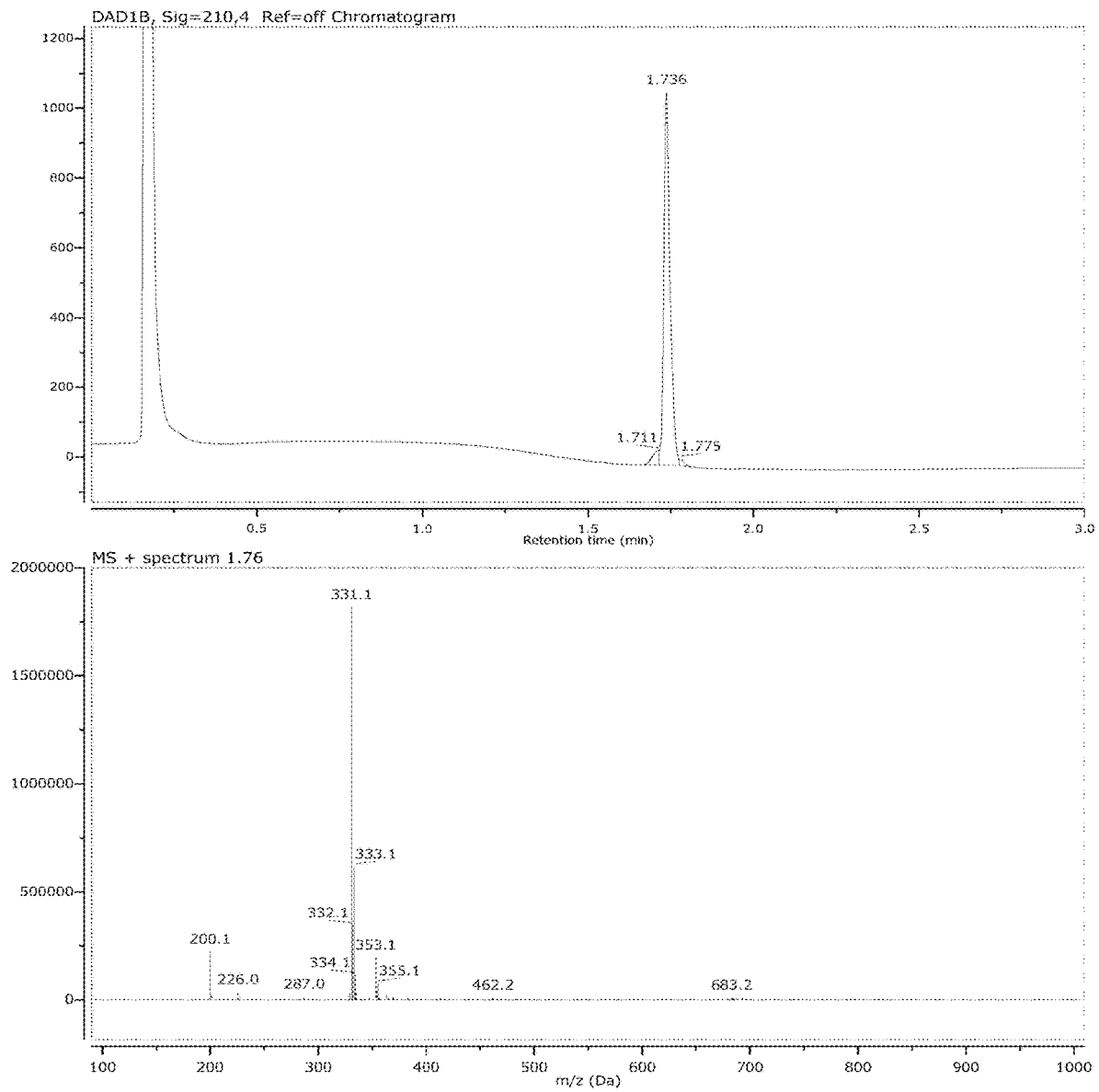

FIG. 22: [Example 14 Compound 14] LCMS and Mass data of 1-(2-(2-hydroxyethoxy)ethyl)-3-(3,3,6,6-tetramethyl-1-oxido-4,5-didehydro-2,3,6,7-tetrahydro-1$\lambda^6$-thiepin-1-ylidene)urea.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 23:
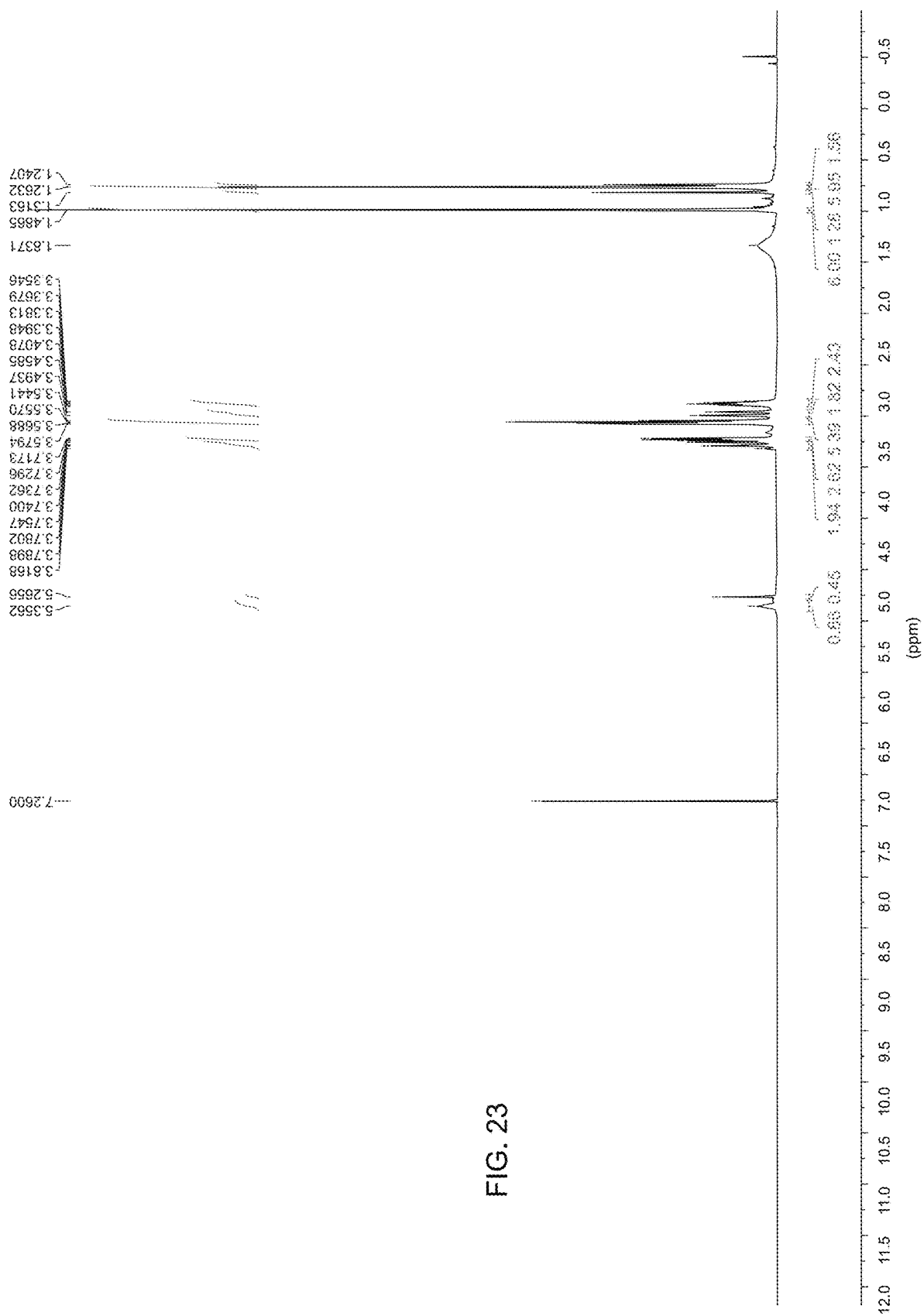

FIG. 23: [Example 14 Compound 14] NMR data of 1-(2-(2-hydroxyethoxy)ethyl)-3-(3,3,6,6-tetramethyl-1-oxido-4,5-didehydro-2,3,6,7-tetrahydro-1$\lambda^6$-thiepin-1-ylidene)urea.

Bruker BioSpin GmbH; Method Pulse Sequence: zg30. Relaxation Delay: 1 s. Solvent: CDCl$_3$. Temperature: ~299.7071 K. Number of Scans: 16. Frequency: 400.132470966543 MHz. Nucleus: 1H.

Figure 24:
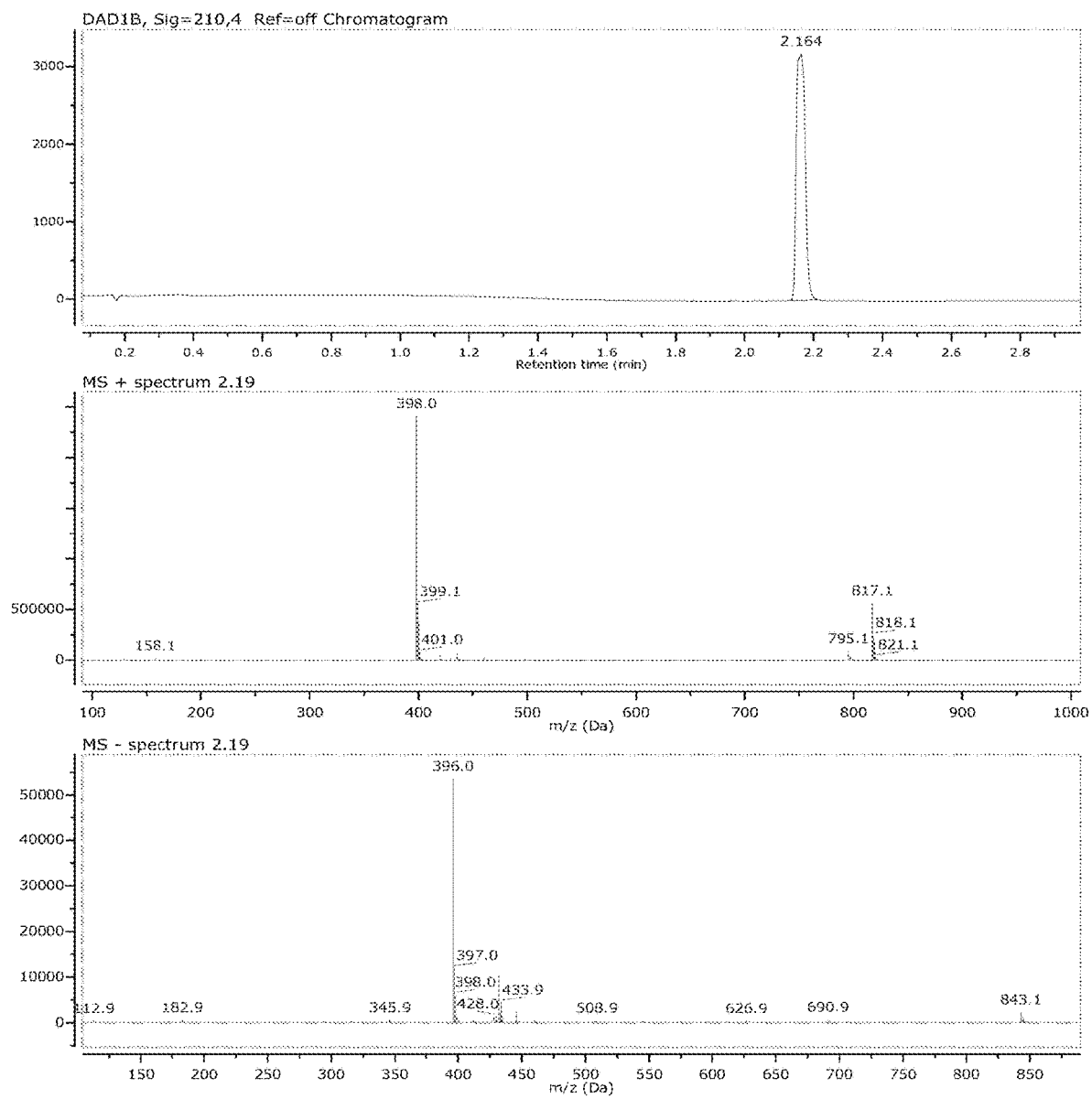

FIG. 24: [Example 15 Compound 15] LCMS and Mass data of methyl 3-(N-(3,3,6,6-tetramethyl-1-oxido-4,5-didehydro-2,3,6,7-tetrahydro-1$\lambda^6$-thiepin-1-ylidene)sulfamoyl)benzoate.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 25:
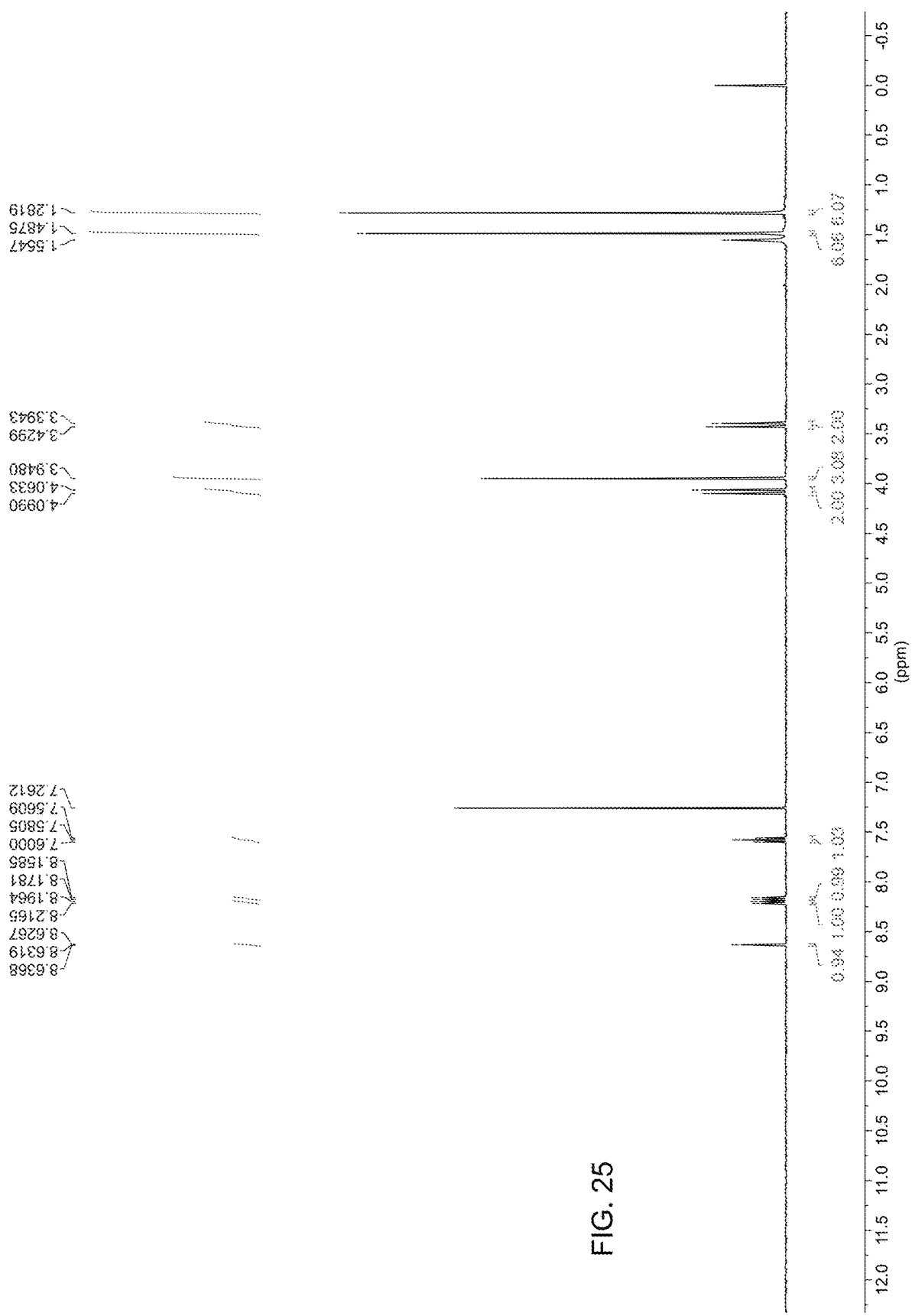

FIG. 25: [Example 15 Compound 15] NMR data of methyl 3-(N-(3,3,6,6-tetramethyl-1-oxido-4,5-didehydro-2,3,6,7-tetrahydro-1$\lambda^6$-thiepin-1-ylidene)sulfamoyl)benzoate.

Bruker BioSpin GmbH; Method Pulse Sequence: zg30. Relaxation Delay: 1 s. Solvent: CDCl$_3$. Temperature: ~299.8145 K. Number of Scans: 16. Frequency: 400.132470966543 MHz. Nucleus: 1H.

Figure 26:
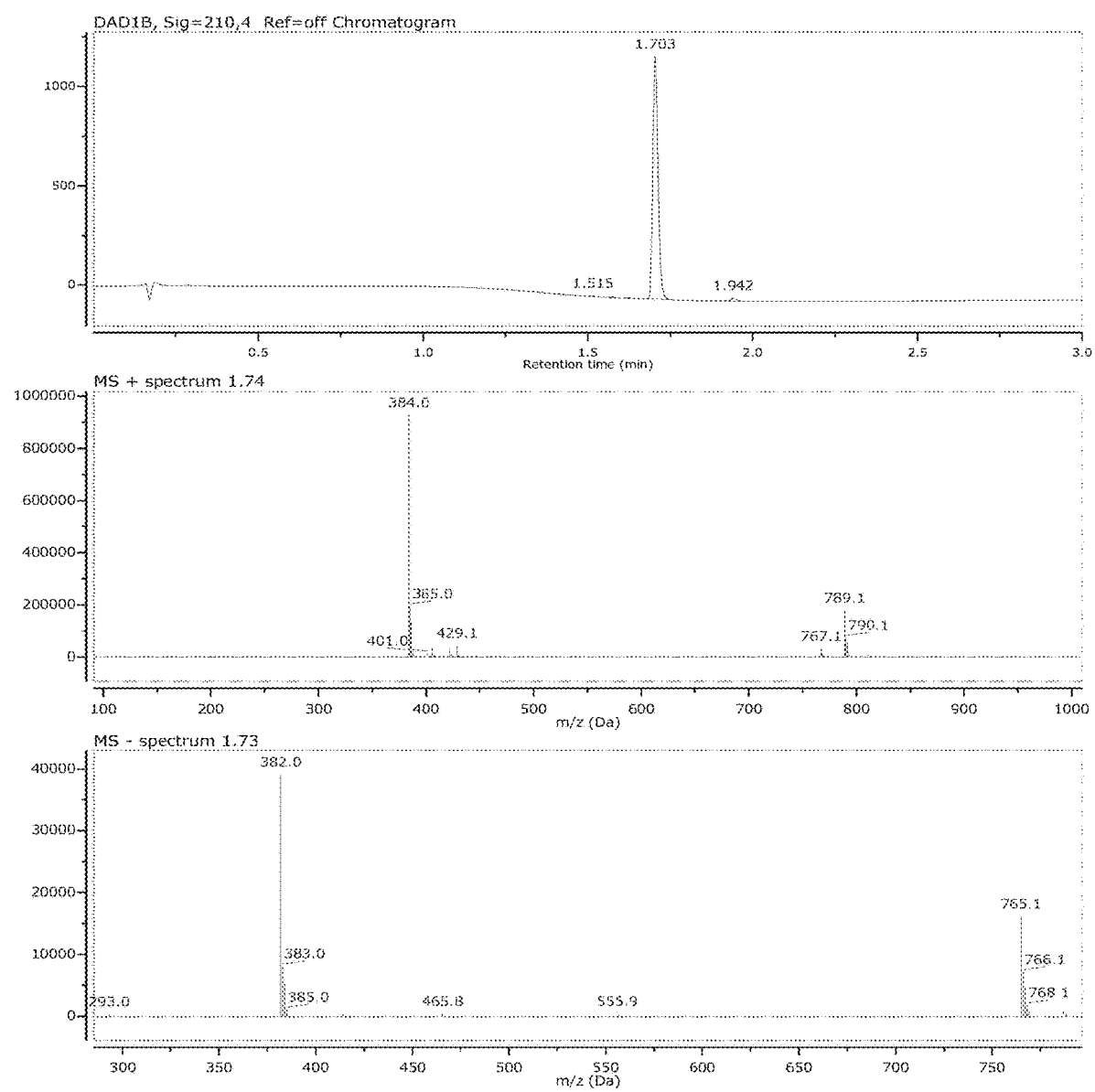

FIG. 26: [Example 16 Compound 16] LCMS and Mass data of 3-(N-(3,3,6,6-tetramethyl-1-oxido-4,5-didehydro-2,3,6,7-tetrahydro-1$\lambda^6$-thiepin-1-ylidene)sulfamoyl)benzoic acid.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 27:
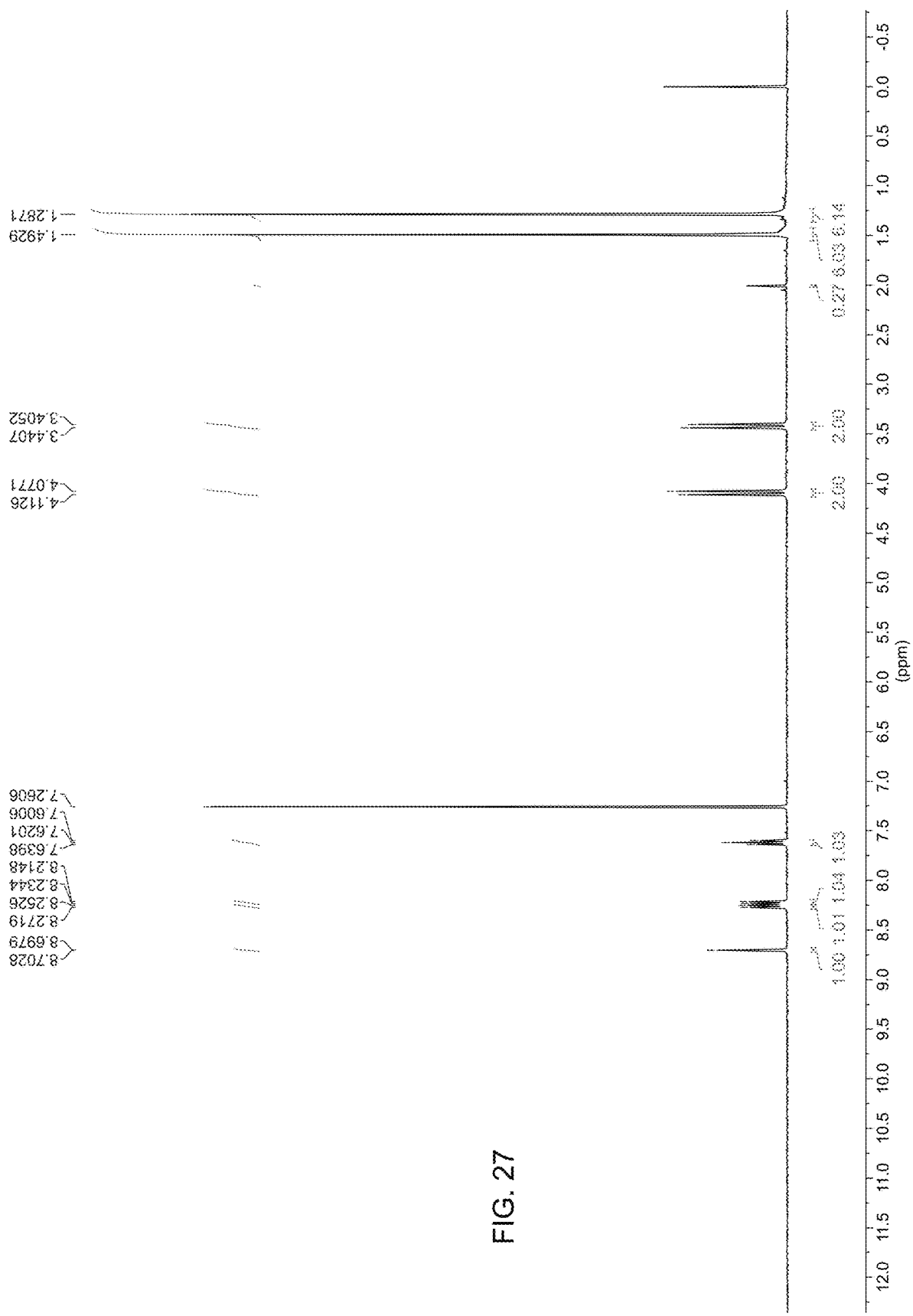

FIG. 27: [Example 16 Compound 16] NMR data of 3-(N-(3,3,6,6-tetramethyl-1-oxido-4,5-didehydro-2,3,6,7-tetrahydro-1$\lambda^6$-thiepin-1-ylidene)sulfamoyl)benzoic acid.

Bruker BioSpin GmbH; Method Pulse Sequence: zg30. Relaxation Delay: 1 s. Solvent: CDCl$_3$. Temperature: ~300.1365 K. Number of Scans: 16. Frequency: 400.132470966543 MHz. Nucleus: 1H.

Figure 28:
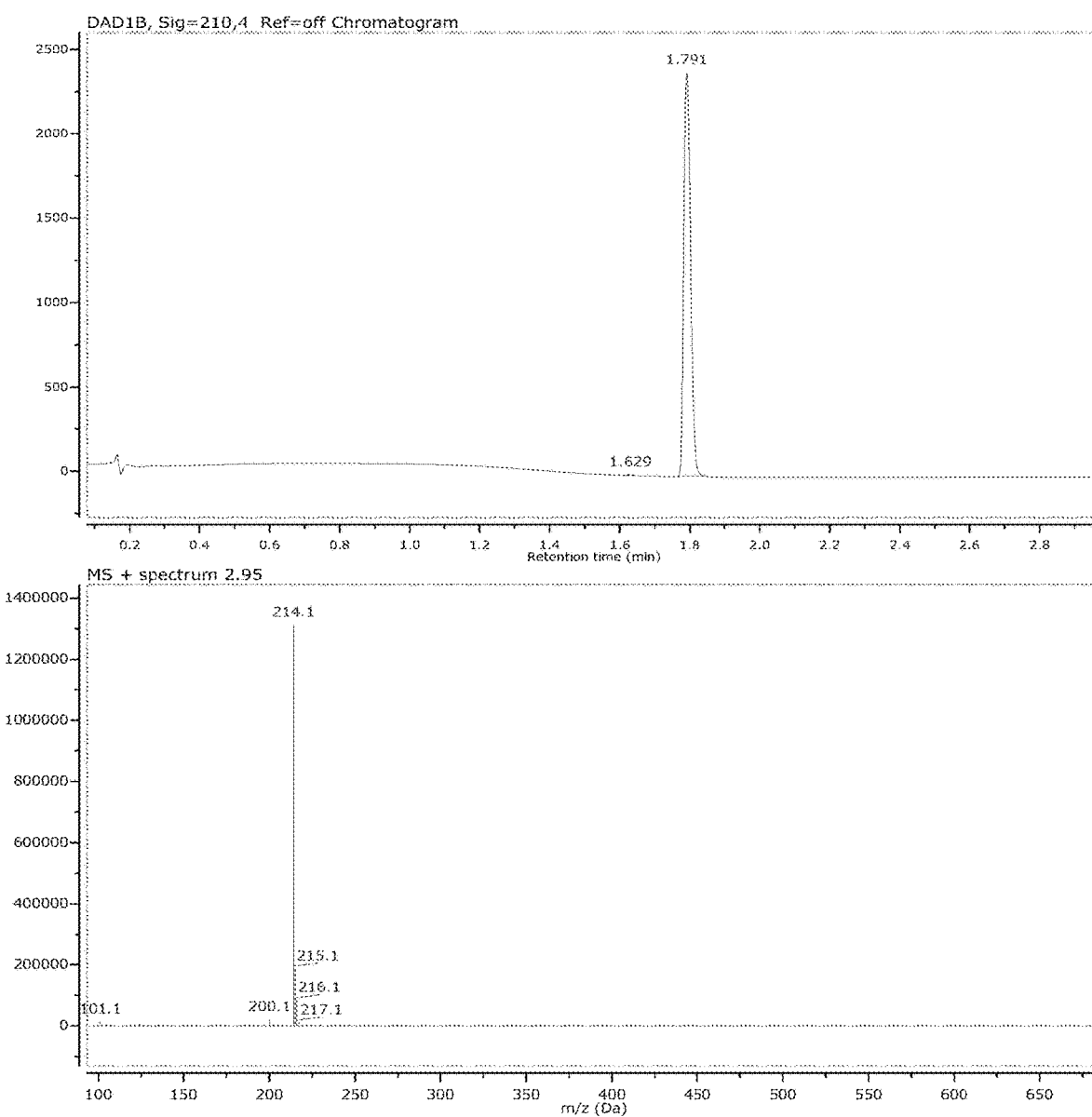

FIG. 28: [Example 17 Compound 17] LCMS and Mass data of 3,3,6,6-tetramethyl-1-(methylimino)-4,5-didehydro-2,3,6,7-tetrahydro-1H-1$\lambda^6$-thiepine 1-oxide.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 29:
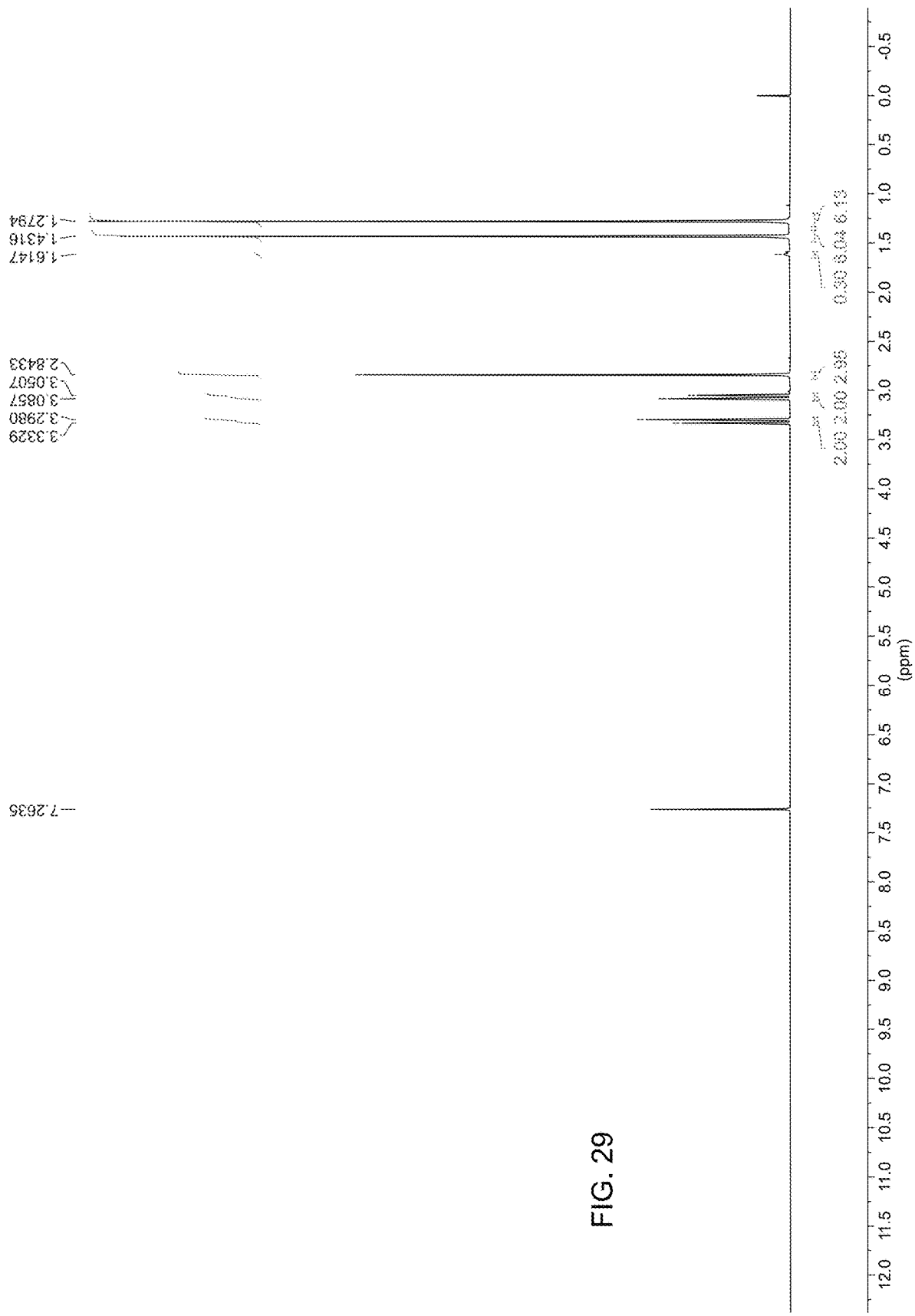

FIG. 29: [Example 17 Compound 17] NMR data of 3,3,6,6-tetramethyl-1-(methylimino)-4,5-didehydro-2,3,6,7-tetrahydro-1H-1$\lambda^6$-thiepine 1-oxide.

Bruker BioSpin GmbH; Method Pulse Sequence: zg30. Relaxation Delay: 1 s. Solvent: CDCl$_3$. Temperature: ~300.1365 K. Number of Scans: 16. Frequency: 400.132470966543 MHz. Nucleus: 1H.

Figure 30:
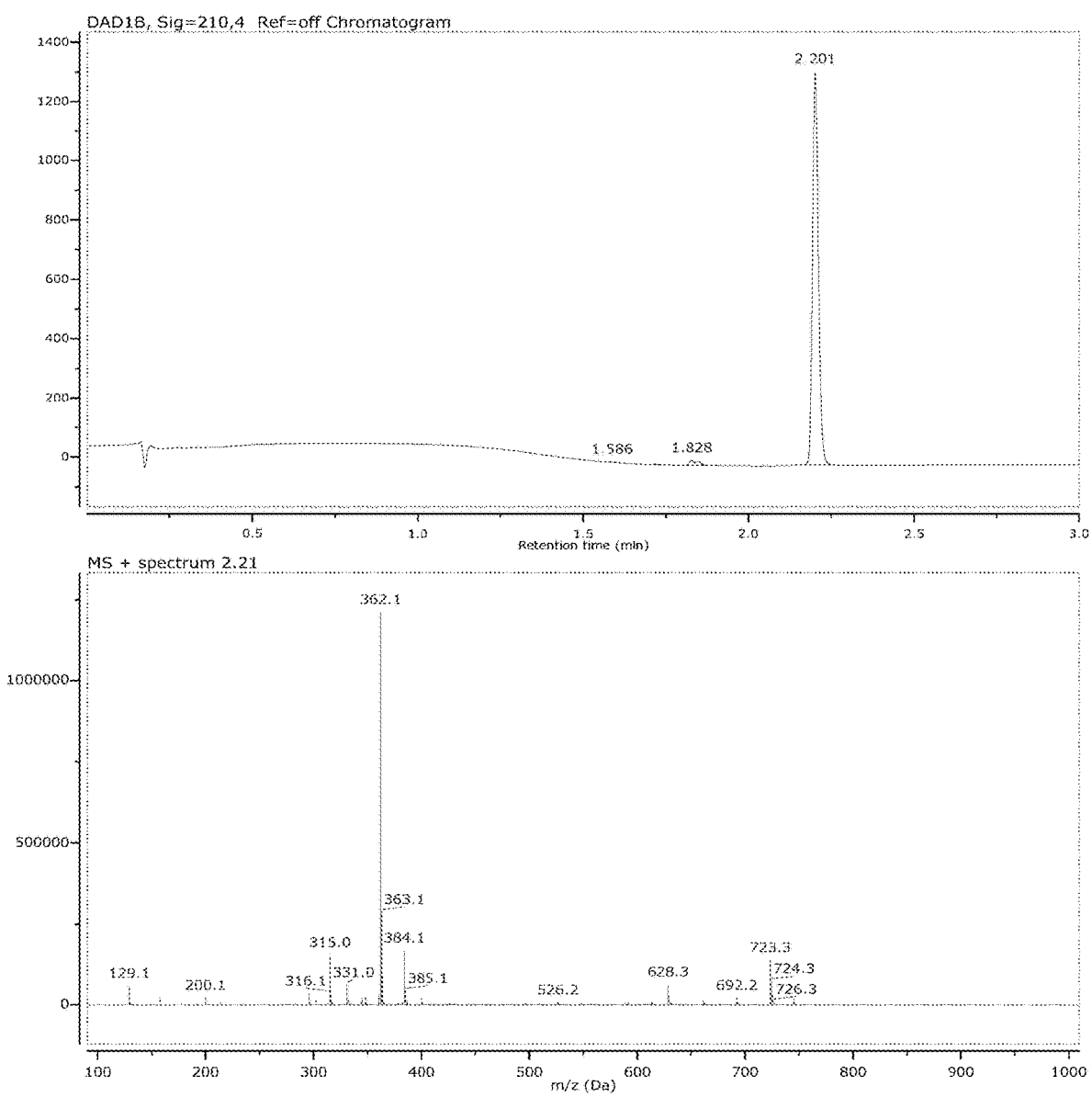

FIG. 30: [Example 18 Compound 18] LCMS and Mass data of methyl 4-((3,3,6,6-tetramethyl-1-(methylimino)-1-oxido-4,5-didehydro-2,3,6,7-tetrahydro-1H-1$\lambda^6$-thiepin-2-yl)methyl)benzoate.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 31:
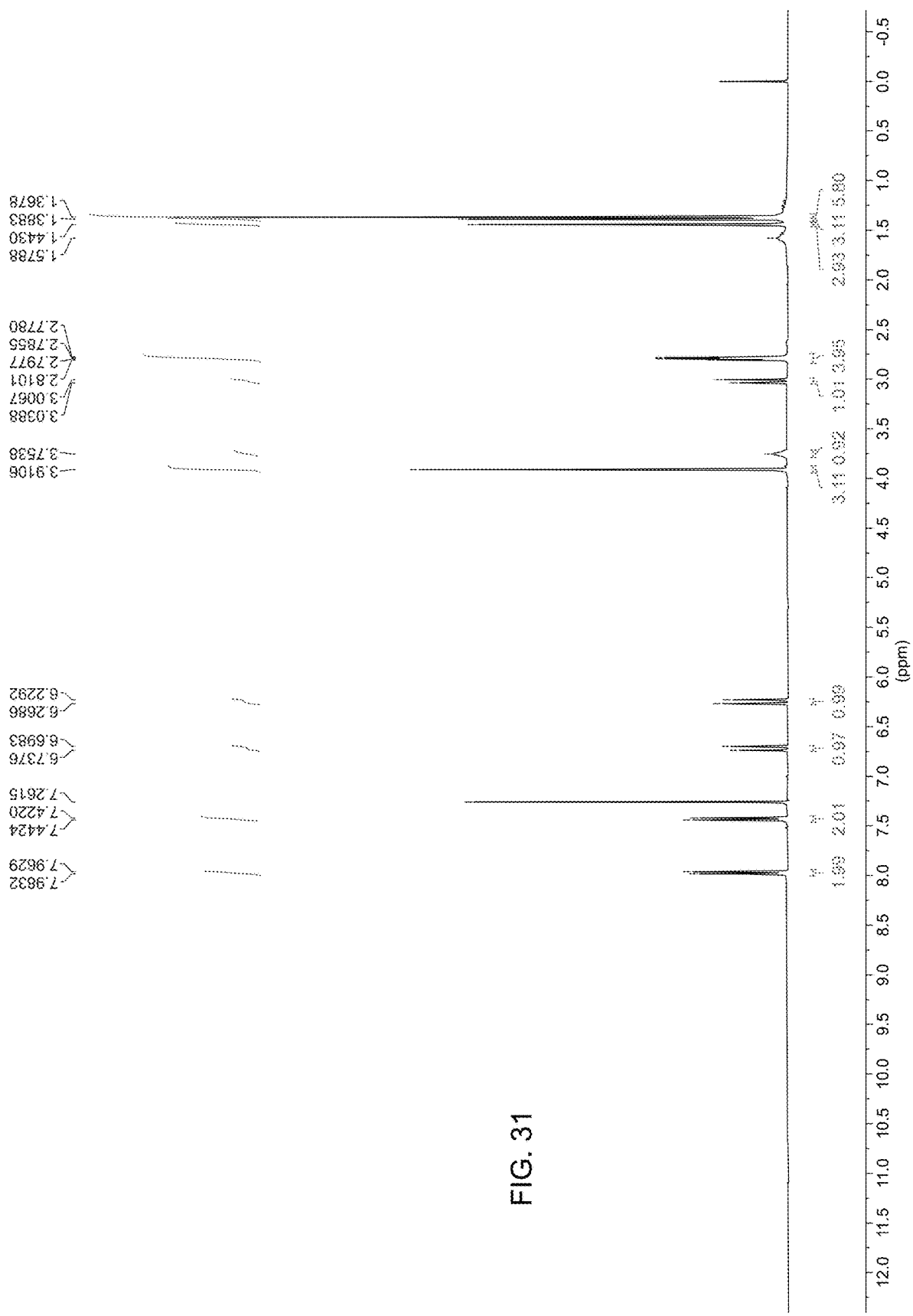

FIG. 31: [Example 18 Compound 18] NMR data of methyl 4-((3,3,6,6-tetramethyl-1-(methylimino)-1-oxido-4,5-didehydro-2,3,6,7-tetrahydro-1H-1λ$^6$-thiepin-2-yl)methyl)benzoate.

Bruker BioSpin GmbH; Method Pulse Sequence: zg30. Relaxation Delay: 1 s. Solvent: CDCl$_3$. Temperature: ~299.9218 K. Number of Scans: 16. Frequency: 400.132470966543 MHz. Nucleus: 1H.

Figure 32:
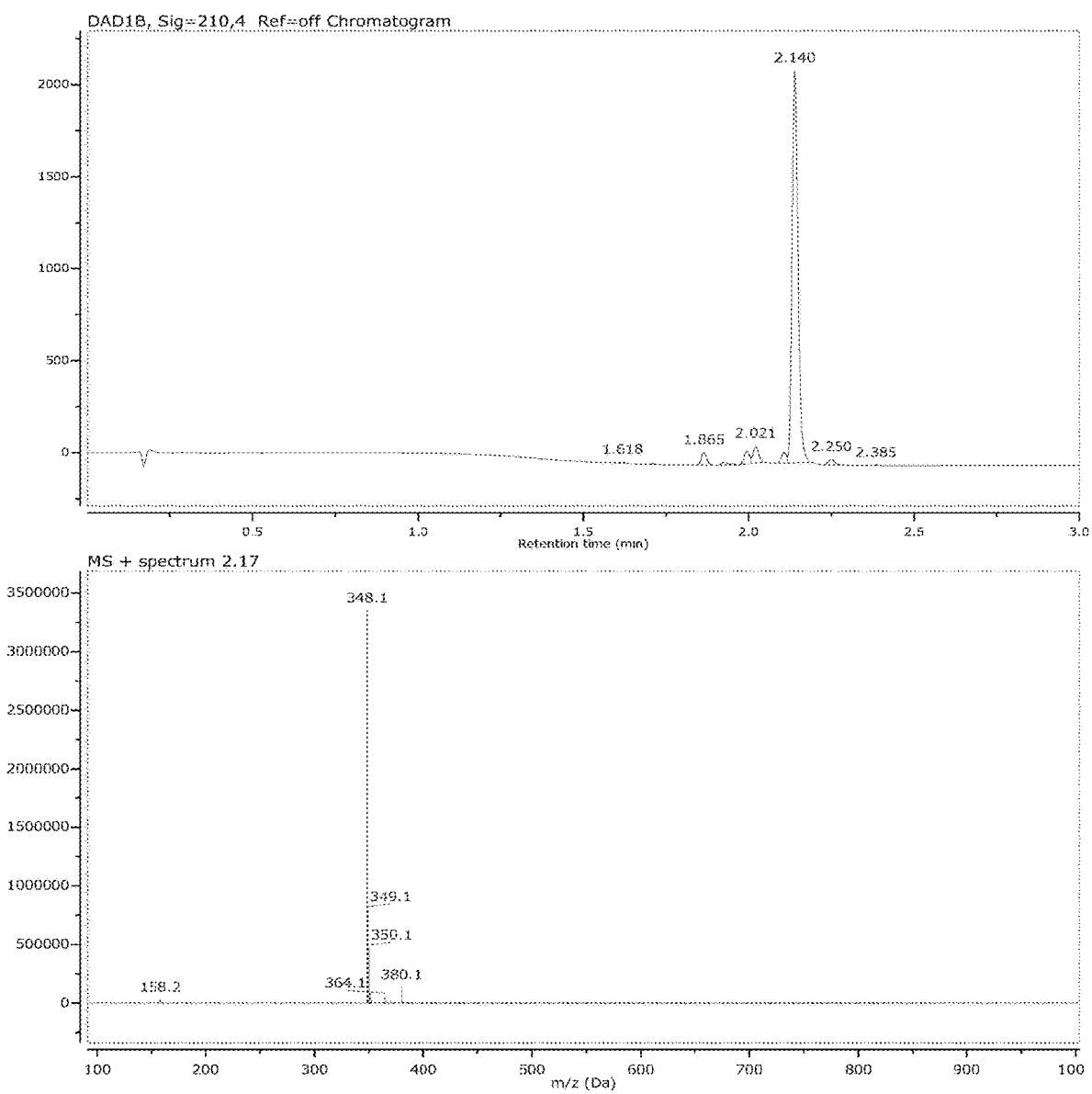

FIG. 32: [Example 19 Compound 19] LCMS and Mass data of methyl 4-(((3,3,6,6-tetramethyl-1-oxido-4,5-didehydro-2,3,6,7-tetrahydro-1λ$^6$-thiepin-1-ylidene)amino)methyl)benzoate.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 33:
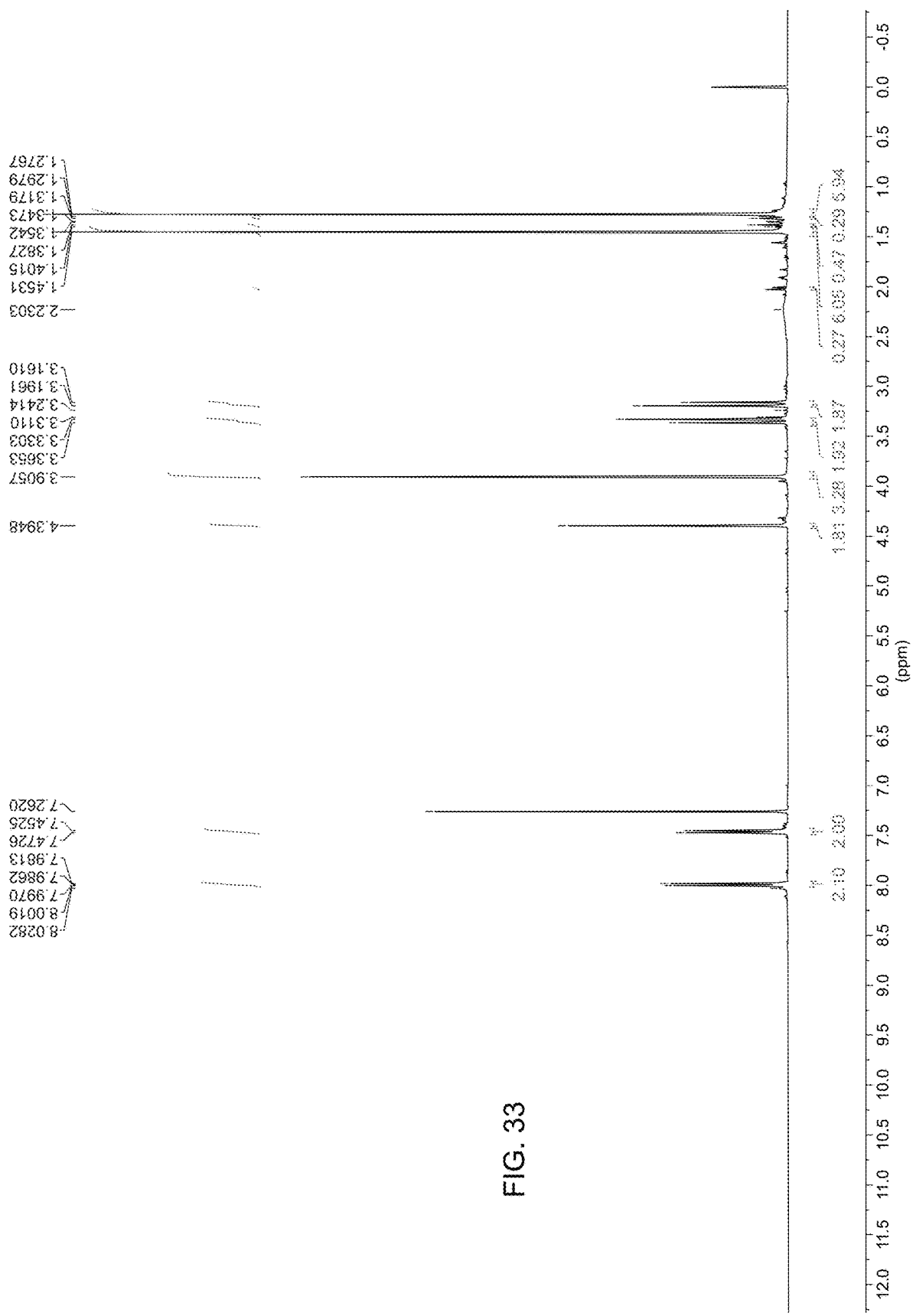

FIG. 33: [Example 19 Compound 19] NMR data of methyl 4-(((3,3,6,6-tetramethyl-1-oxido-4,5-didehydro-2,3,6,7-tetrahydro-1λ$^6$-thiepin-1-ylidene)amino)methyl)benzoate.

Bruker BioSpin GmbH; Method Pulse Sequence: zg30. Relaxation Delay: 1 s. Solvent: CDCl$_3$. Temperature: ~299.9218 K. Number of Scans: 16. Frequency: 400.132470966543 MHz. Nucleus: 1H.

Figure 34:
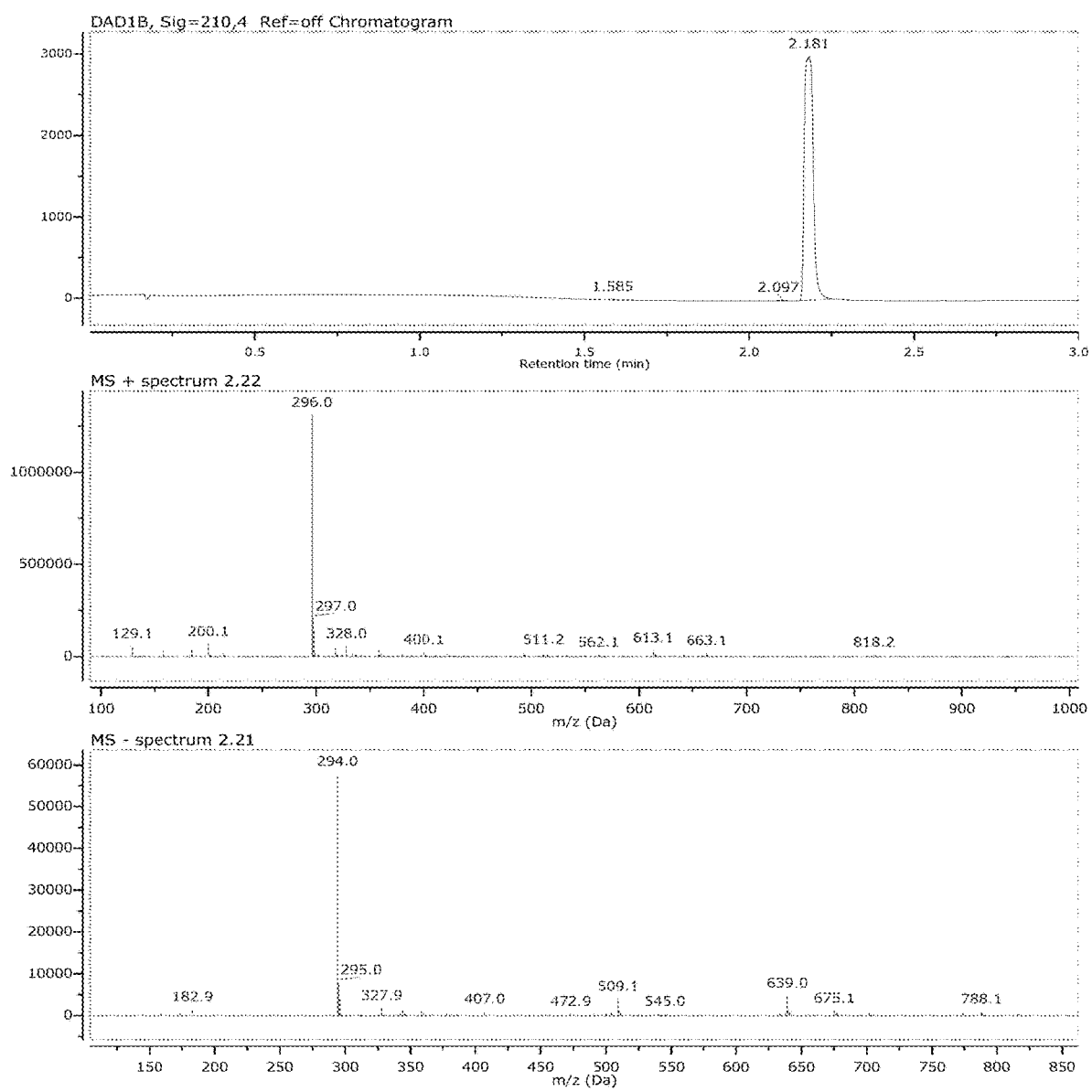

FIG. 34: [Example 13 Compound 13] LCMS and Mass data of 2,2,2-trifluoro-N-(3,3,6,6-tetramethyl-1-oxido-4,5-didehydro-2,3,6,7-tetrahydro-1λ$^6$-thiepin-1-ylidene)acetamide.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 35:
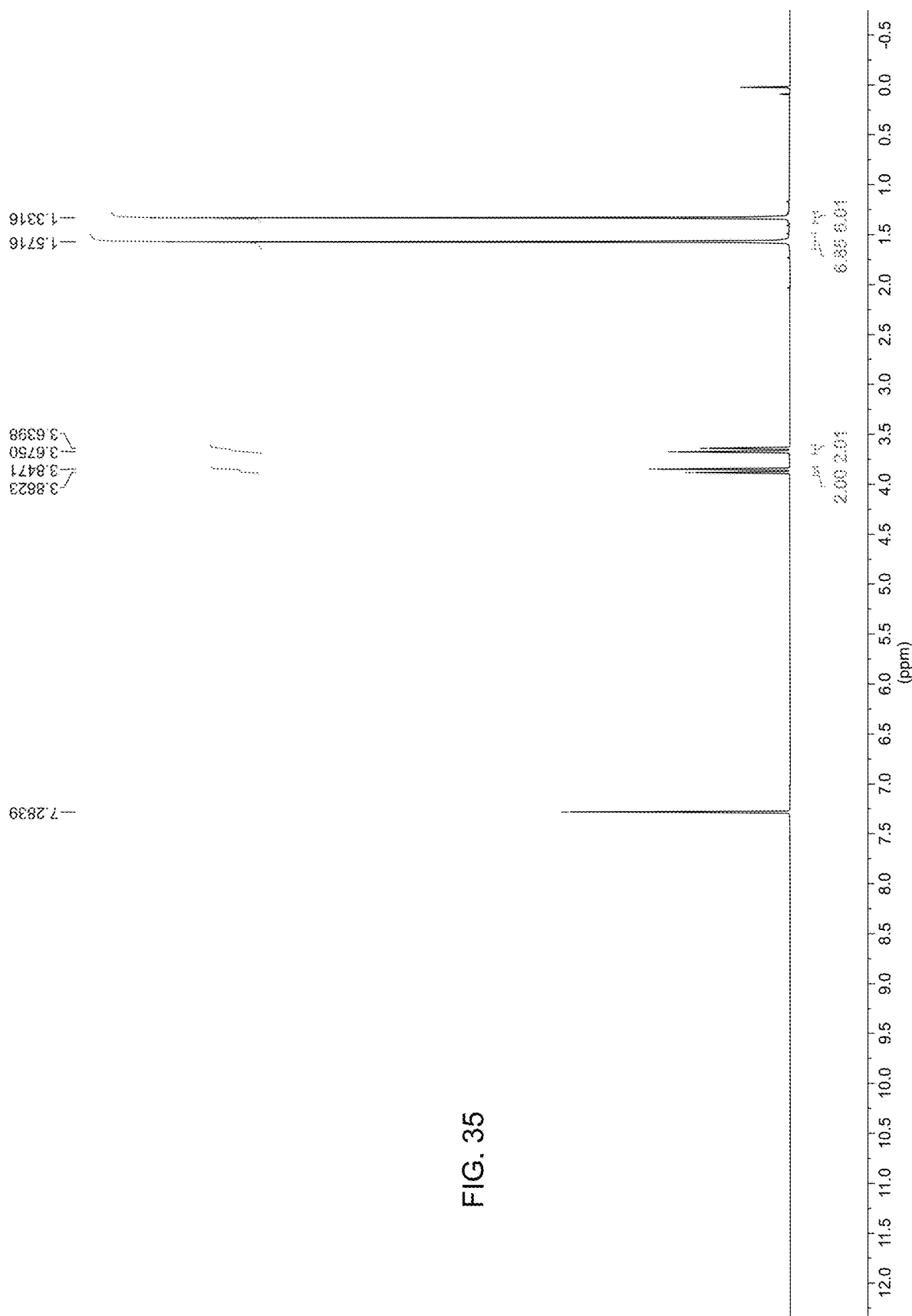

FIG. 35: [Example 13 Compound 13] NMR data of 2,2,2-trifluoro-N-(3,3,6,6-tetramethyl-1-oxido-4,5-didehydro-2,3,6,7-tetrahydro-1λ$^6$-thiepin-1-ylidene)acetamide.

Bruker BioSpin GmbH; Method Pulse Sequence: zg30. Relaxation Delay: 1 s. Solvent: CDCl$_3$. Temperature: ~299.1845 K. Number of Scans: 16. Frequency: 400.132470966543 MHz. Nucleus: 1H.

Figure 36:
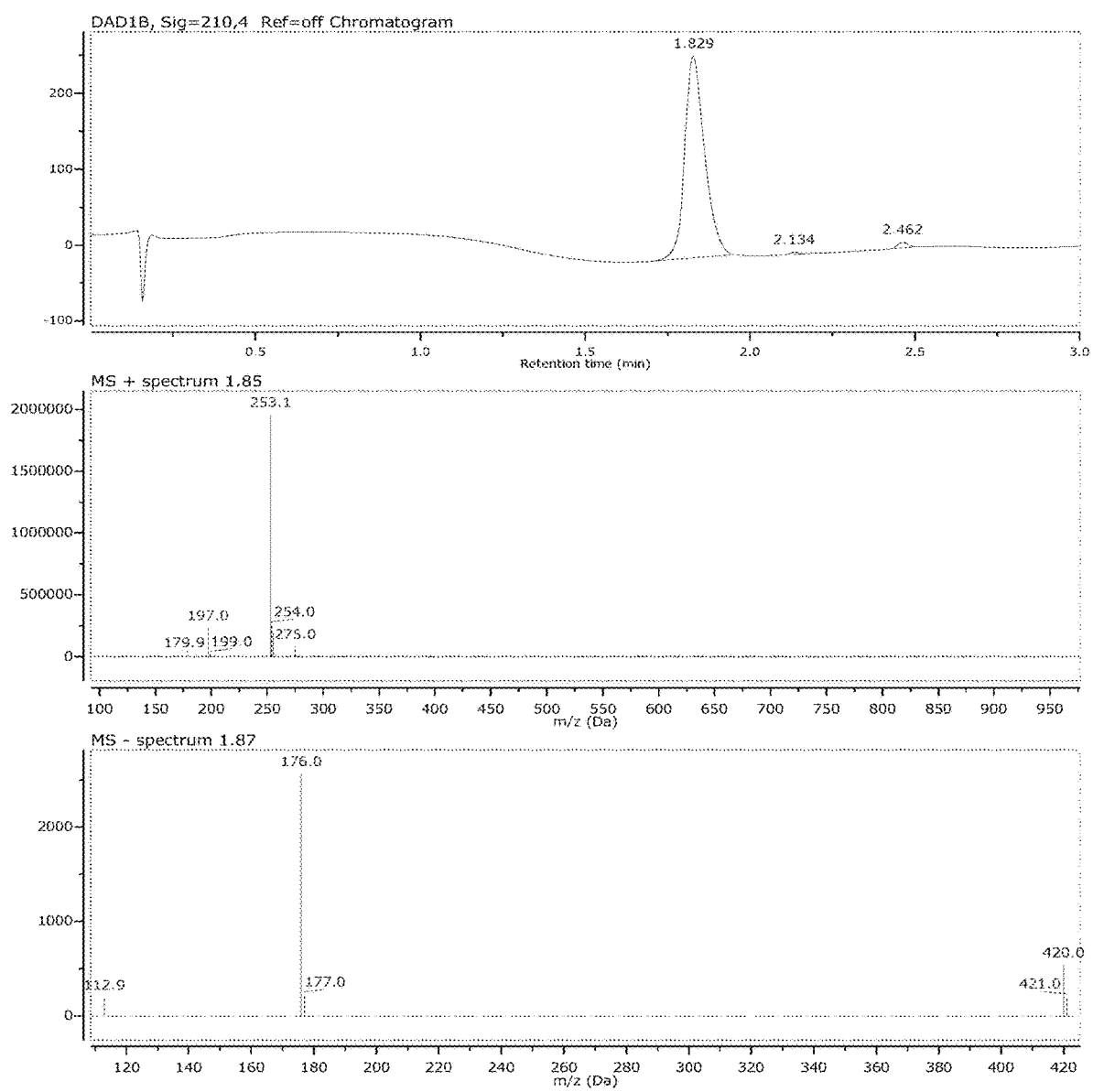

FIG. 36: [Example 20 Compound 21] LCMS and Mass data of tert-butyl (2-((2-aminoethyl)disulfaneyl)ethyl) carbamate.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 37:
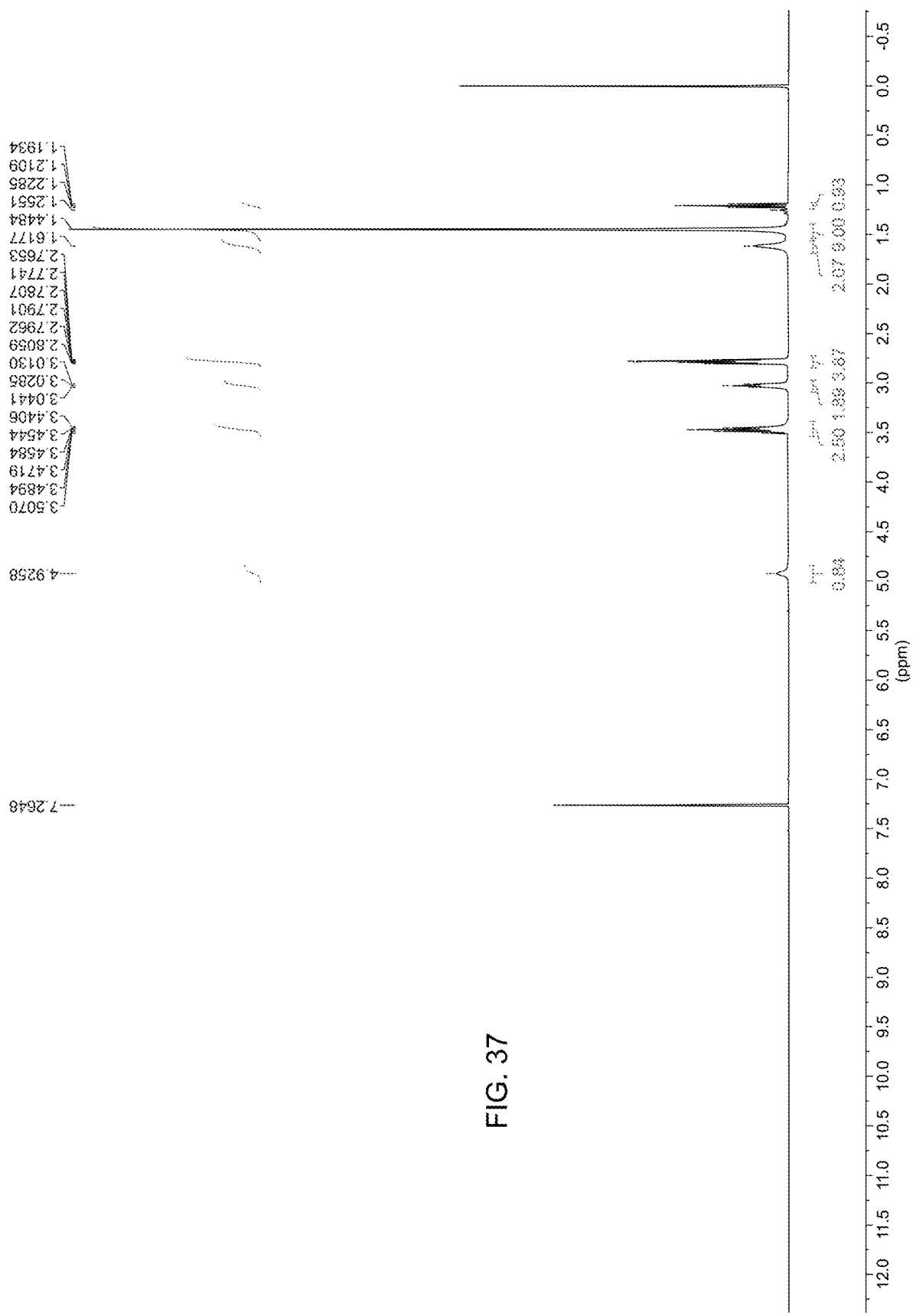

FIG. 37: [Example 20 Compound 21] NMR data of tert-butyl (2-((2-aminoethyl)disulfaneyl)ethyl)carbamate.

Bruker BioSpin GmbH; Method Pulse Sequence: zg30. Relaxation Delay: 1 s. Solvent: CDCl$_3$. Temperature: ~295.7355 K. Number of Scans: 16. Frequency: 400.132470966543 MHz. Nucleus: 1H.

Figure 38:
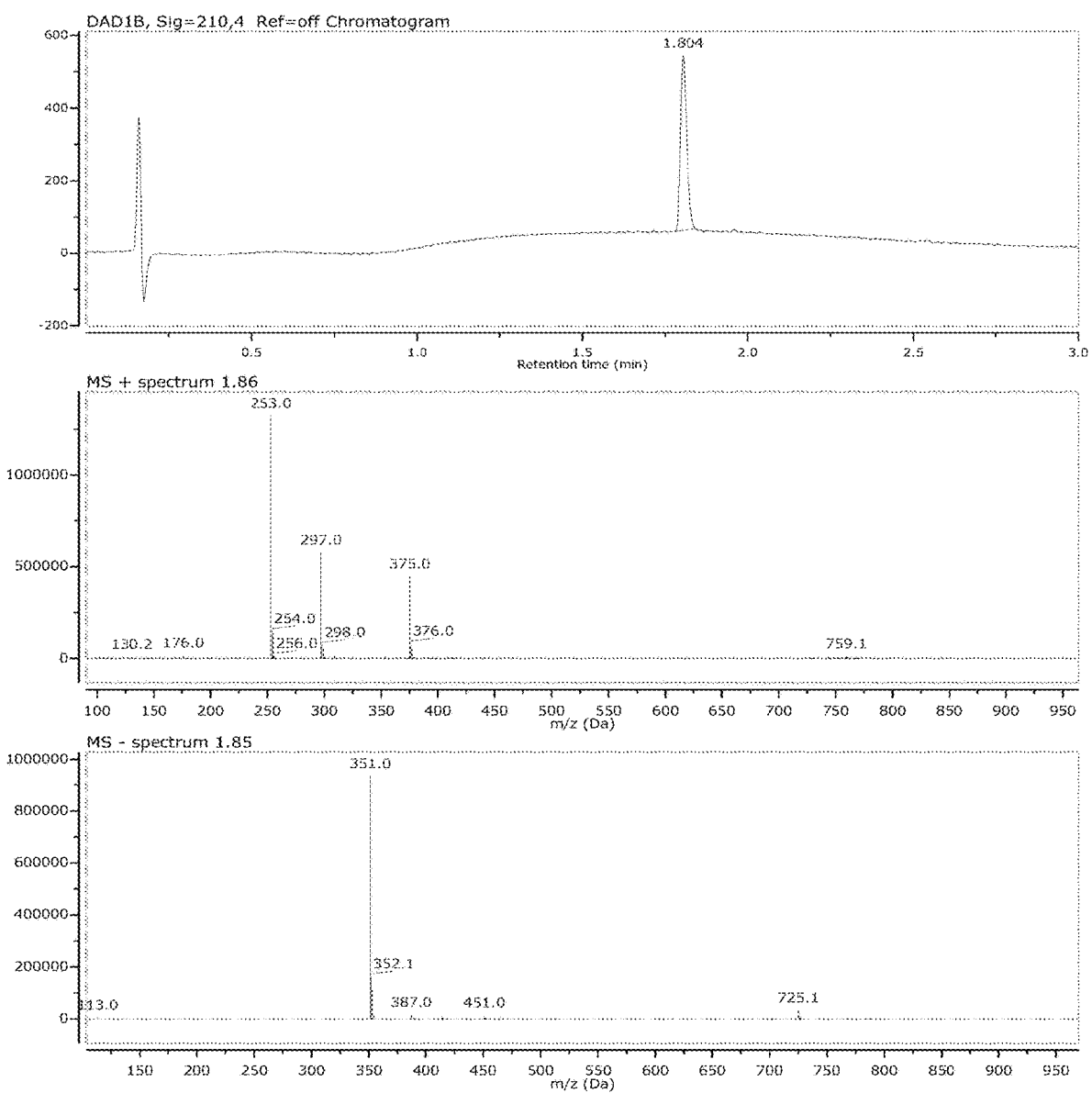

FIG. 38: [Example 21 Compound 22] LCMS and Mass data of 2,2-dimethyl-4,13-dioxo-3-oxa-8,9-dithia-5,12-diazahexadecan-16-oic acid.

Column: Waters XSelect CSH C18 (30×2.1 mm, 3.5μ). Flow: 1 ml/min; Column temp: 35° C. Eluent A: 0.1% Formic acid in acetonitrile. Eluent B: 0.1% Formic acid in water. Lin. Gradient: t=0 min 5% A, t=1.6 min 98% A, t=3 min 98% A. Post time: 1.3 min. Detection DAD (220-320 mu, 210 and 220 nm). Detection: PDA (210-400 nm). Detection: MSD ESI pos/neg (mass range: 100-1000). Detection: ELSD (Alltech 3300): gas flow 1.5 ml/min, gas temp: 40° C.

Figure 39:
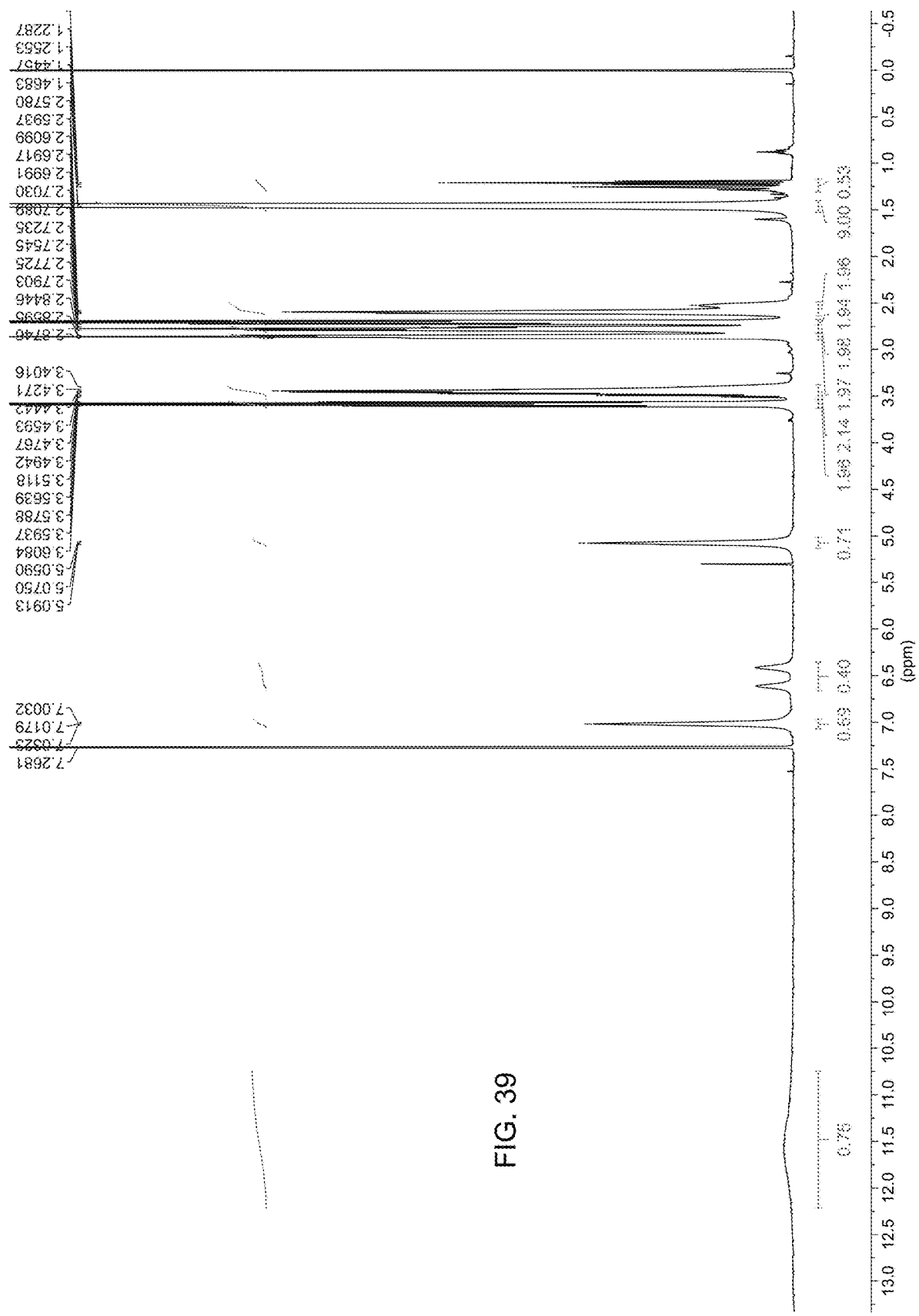

FIG. 39: [Example 21 Compound 22] NMR data of 2,2-dimethyl-4,13-dioxo-3-oxa-8,9-dithia-5,12-diazahexadecan-16-oic acid.

Bruker BioSpin GmbH; Method Pulse Sequence: zg30. Relaxation Delay: 1 s. Solvent: CDCl$_3$. Temperature: ~295.6282 K. Number of Scans: 16. Frequency: 400.132470966543 MHz. Nucleus: 1H.

Figure 40:
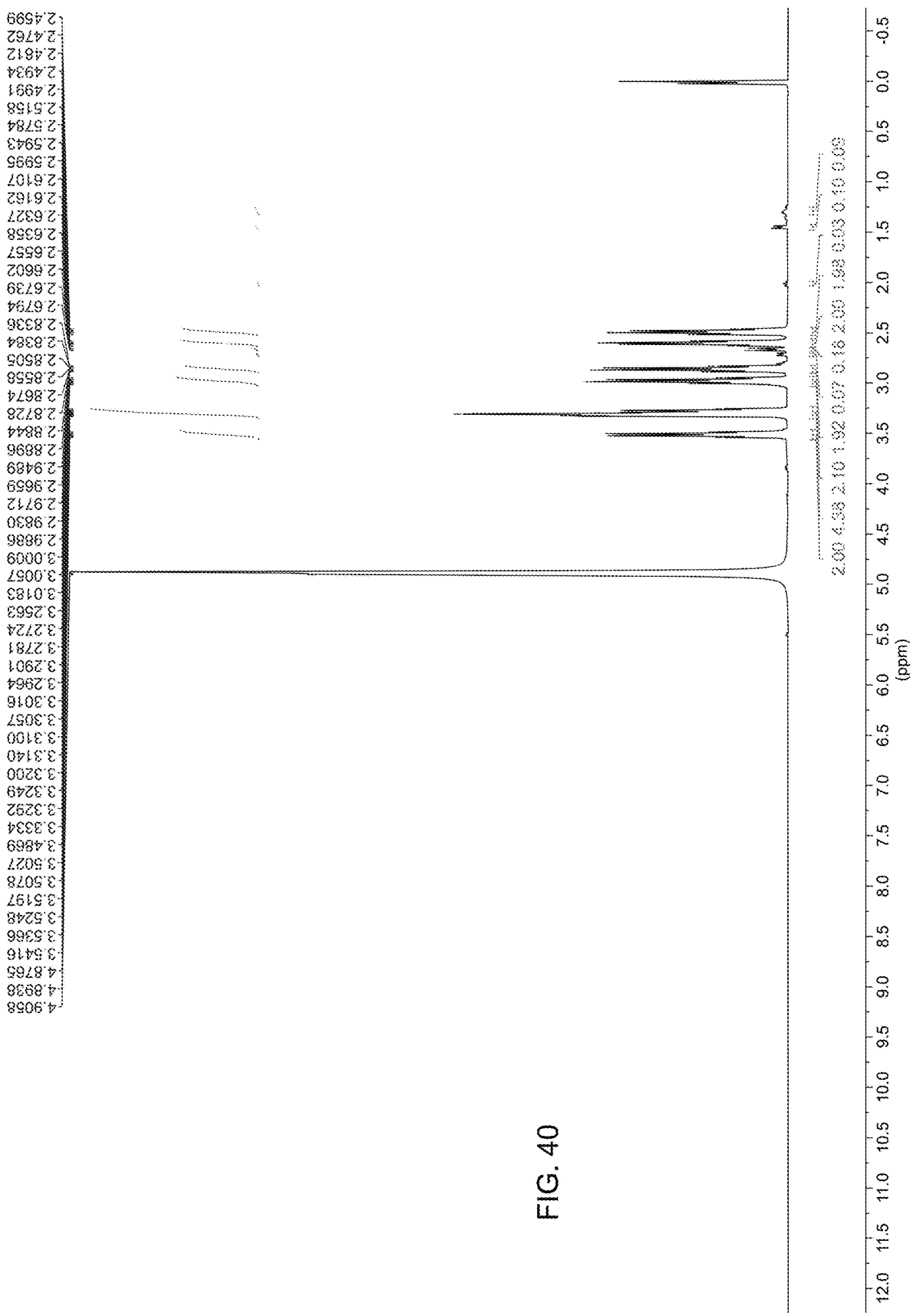

FIG. 40: [Example 22 Compound 23] NMR data of 4-((2-((2-aminoethyl)disulfaneyl)ethyl)amino)-4-oxobutanoic acid trifluoroacetate salt.

Bruker BioSpin GmbH; Method Pulse Sequence: zg30. Relaxation Delay: 1 s. Solvent: MeOD. Temperature: ~298.097 K. Number of Scans: 16. Frequency: 400.132470966543 MHz. Nucleus: 1H.

Figure 41:
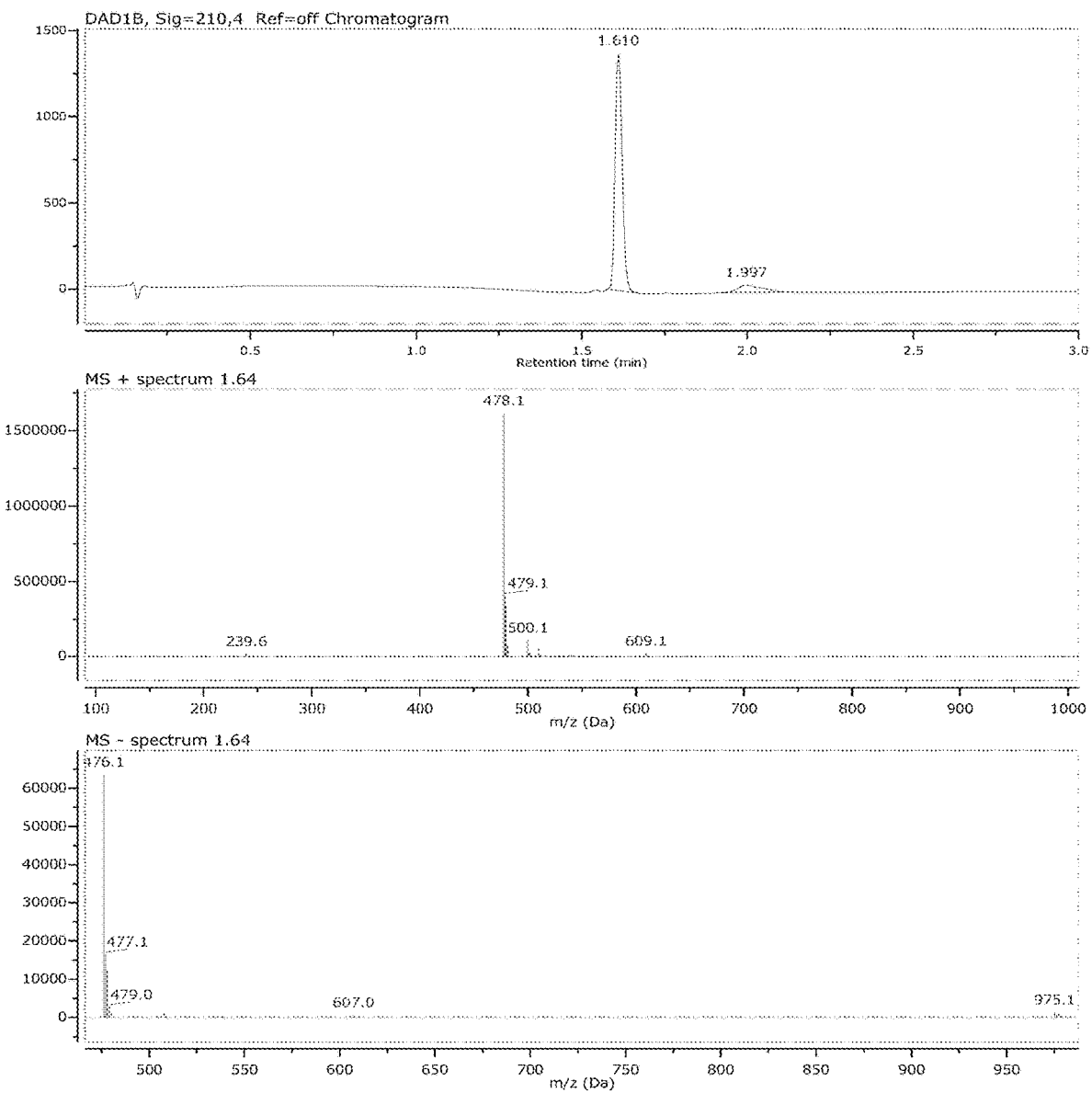

FIG. 41: [Example 23 Compound 24] LCMS and Mass data of 4-oxo-4-((2-((2-(3-(3,3,6,6-tetramethyl-1-oxido-4,5-didehydro-2,3,6,7-tetrahydro-1λ$^6$-thiepin-1-ylidene)ureido)ethyl)disulfaneyl)ethyl)amino) butanoic acid.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 42:
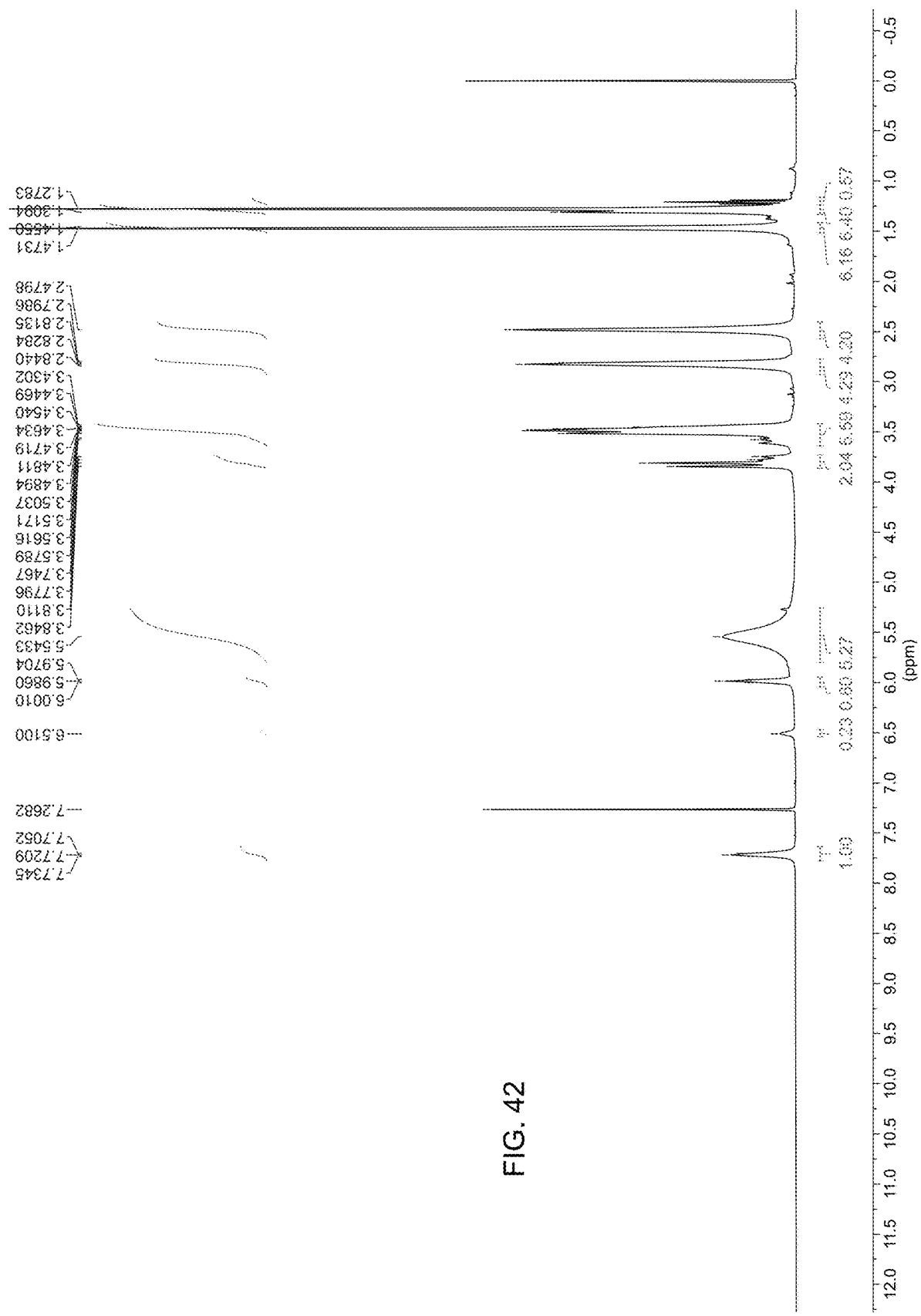

FIG. 42: [Example 23 Compound 24] NMR data of 4-oxo-4-((2-((2-(3-(3,3,6,6-tetramethyl-1-oxido-4,5-didehydro-2,3,6,7-tetrahydro-1λ$^6$-thiepin-1-ylidene)ureido)ethyl)disulfaneyl)ethyl)amino)butanoic acid.

Bruker BioSpin GmbH; Method Pulse Sequence: zg30. Relaxation Delay: 1 s. Solvent: CDCl$_3$. Temperature: ~298.097 K. Number of Scans: 16. Frequency: 400.132470966543 MHz. Nucleus: 1H.

Figure 43:
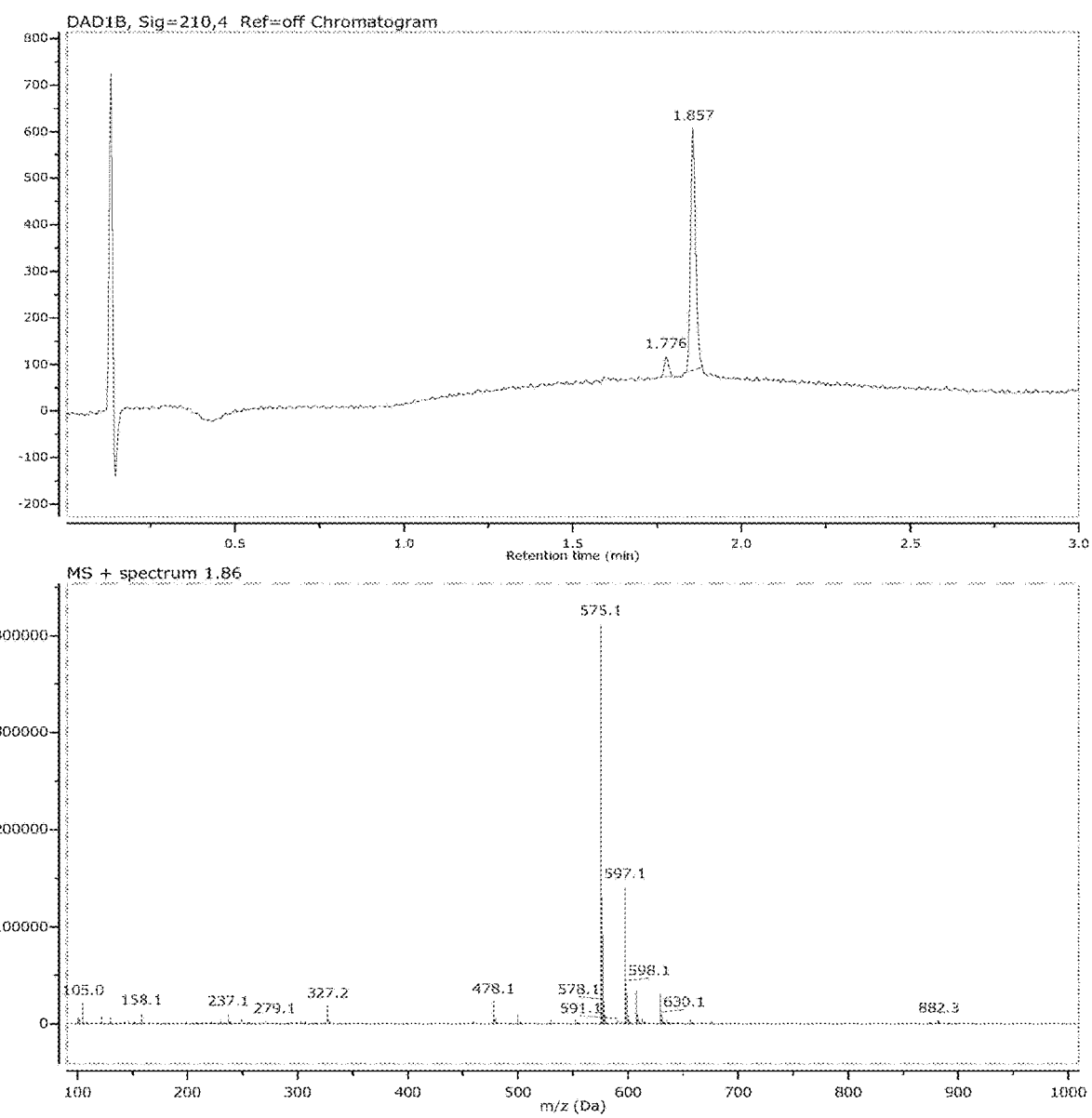

FIG. 43: [Example 24 Compound 25] LCMS and Mass data of 2,5-dioxopyrrolidin-1-yl 4-oxo-4-((2-((2-(3-(3,3,6,6-tetramethyl-1-oxido-4,5-didehydro-2,3,6,7-tetrahydro-1λ$^6$-thiepin-1-ylidene)ureido)ethyl)disulfaneyl)ethyl)amino)butanoate.

Column: Waters XSelect CSH C18 (30×2.1 mm, 3.5μ). Flow: 1 ml/min; Column temp: 35° C. Eluent A: 0.1% Formic acid in acetonitrile. Eluent B: 0.1% Formic acid in water. Lin. Gradient: t=0 min 5% A, t=1.6 min 98% A, t=3 min 98% A. Post time: 1.3 min. Detection DAD (220-320 mu, 210 and 220 nm). Detection: PDA (210-400 nm). Detection: MSD ESI pos/neg (mass range: 100-1000). Detection: ELSD (Alltech 3300): gas flow 1.5 ml/min, gas temp: 40° C.

Figure 44:
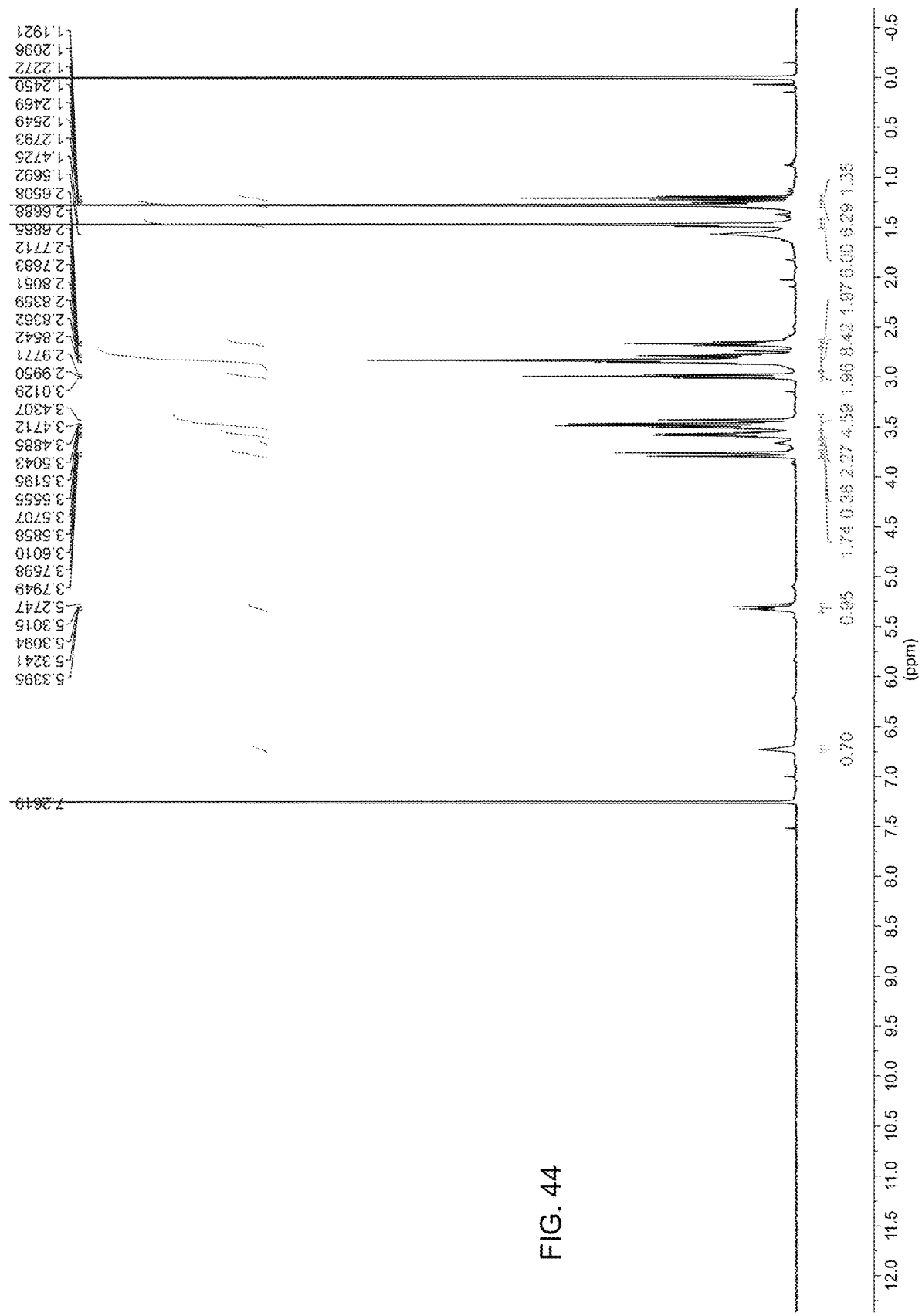

FIG. 44: [Example 24 Compound 25] NMR data of 2,5-dioxopyrrolidin-1-yl 4-oxo-4-((2-((2-(3-(3,3,6,6-tetramethyl-1-oxido-4,5-didehydro-2,3,6,7-tetrahydro-1λ$^6$-thiepin-1-ylidene)ureido)ethyl)disulfaneyl)ethyl)amino)butanoate.

Bruker BioSpin GmbH; Method Pulse Sequence: zg30. Relaxation Delay: 1 s. Solvent: CDCl$_3$. Temperature: ~298.097 K. Number of Scans: 16. Frequency: 400.132470966543 MHz. Nucleus: 1H.

Figure 45:
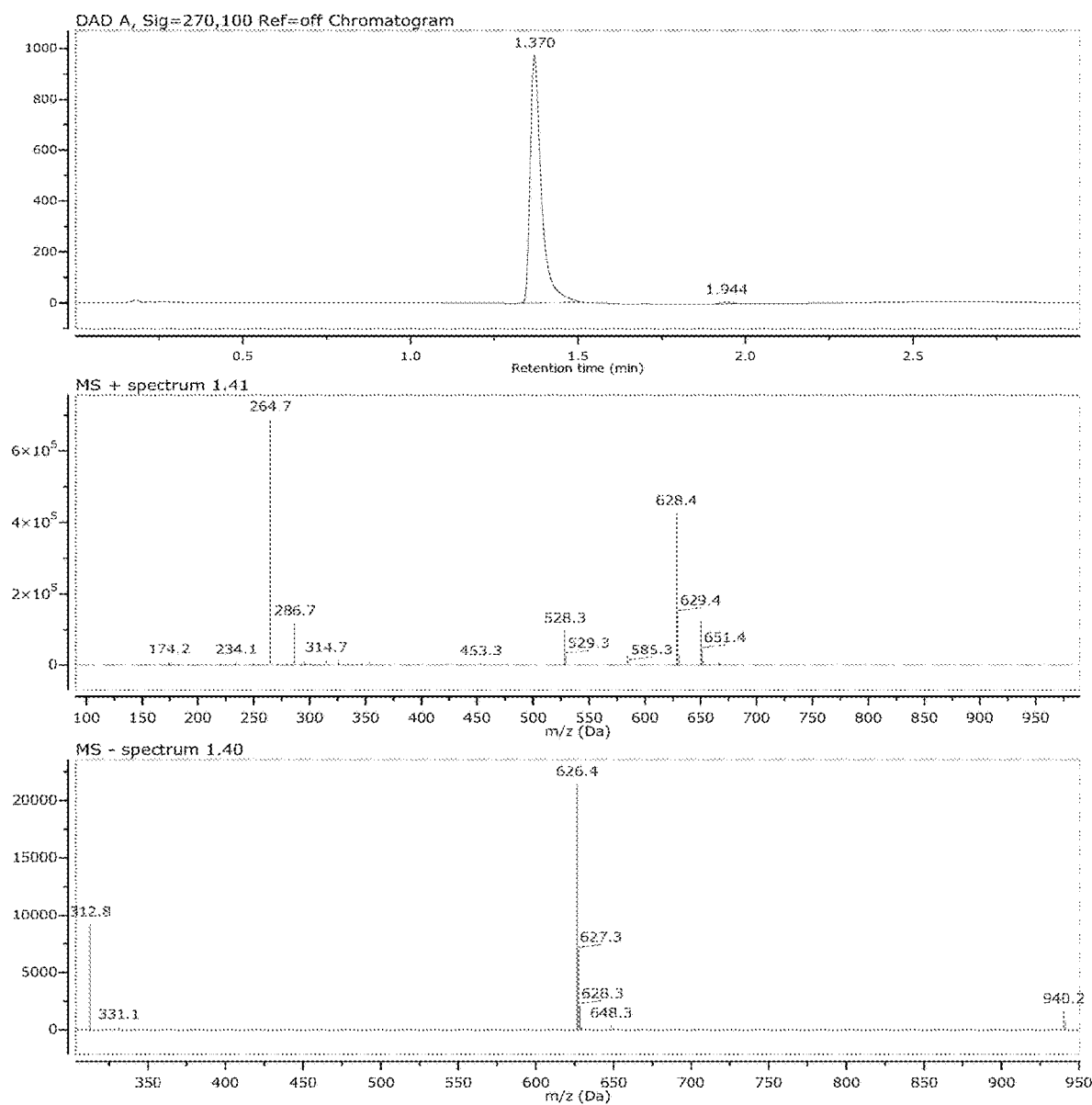

FIG. 45: [Example 29 Compound 30] LCMS and Mass data of (S)-15-(4-(((2-amino-4-oxo-3,4-dihydropteridin-6-yl)methyl)amino)benzamido)-2,2-dimethyl-4,12-dioxo-3,8-dioxa-5,11-diazahexadecan-16-oic acid.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 46:
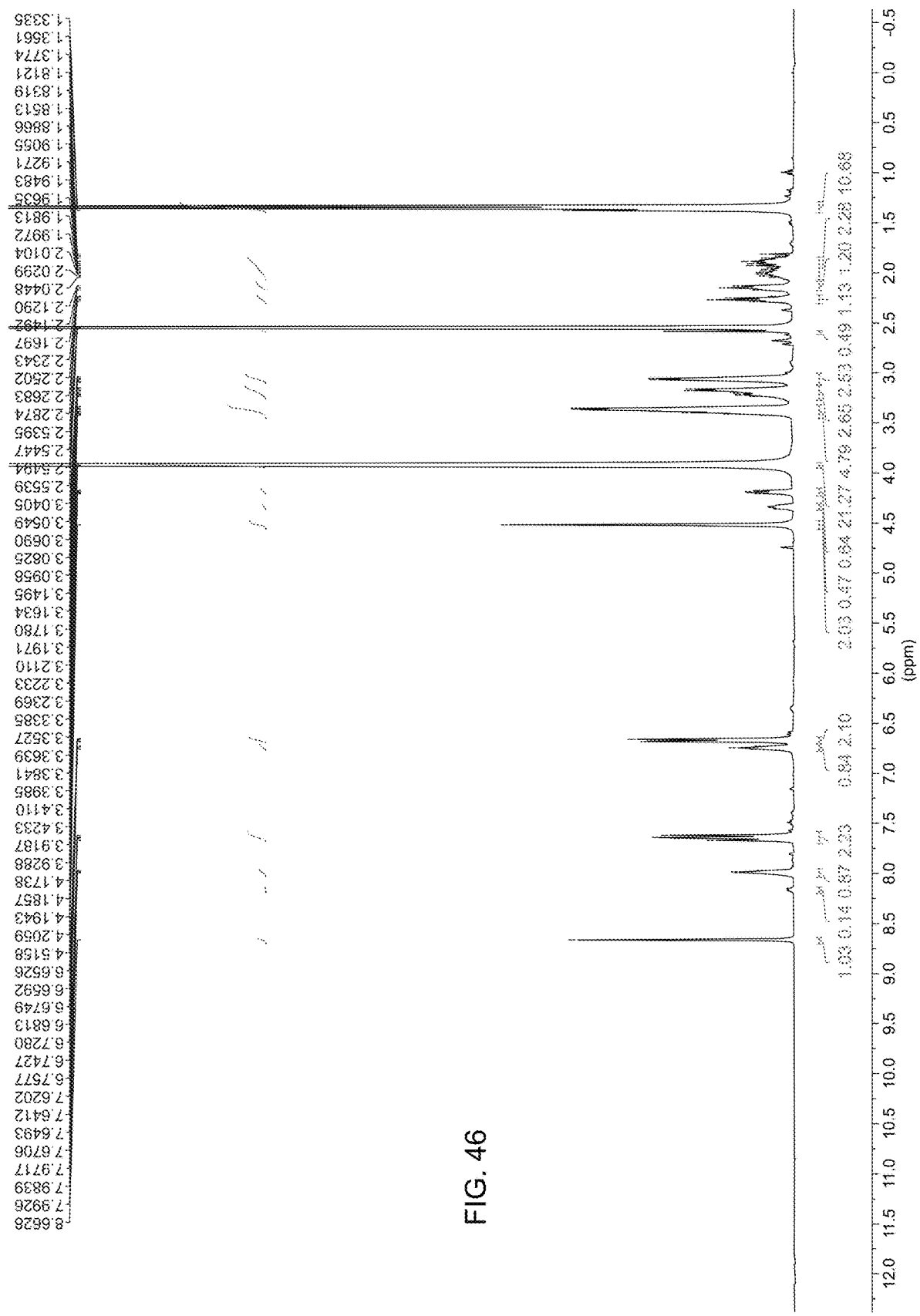

FIG. 46: [Example 29 Compound 30] NMR data of (S)-15-(4-(((2-amino-4-oxo-3,4-dihydropteridin-6-yl)methyl)amino)benzamido)-2,2-dimethyl-4,12-dioxo-3,8-dioxa-5,11-diazahexadecan-16-oic acid.

Bruker BioSpin GmbH; Method Pulse Sequence: zg30. Relaxation Delay: 1 s. Solvent: DMSO-$d_6$. Temperature: ~295.7355 K. Number of Scans: 64. Frequency: 400.132470966543 MHz. Nucleus: 1H.

Figure 47:
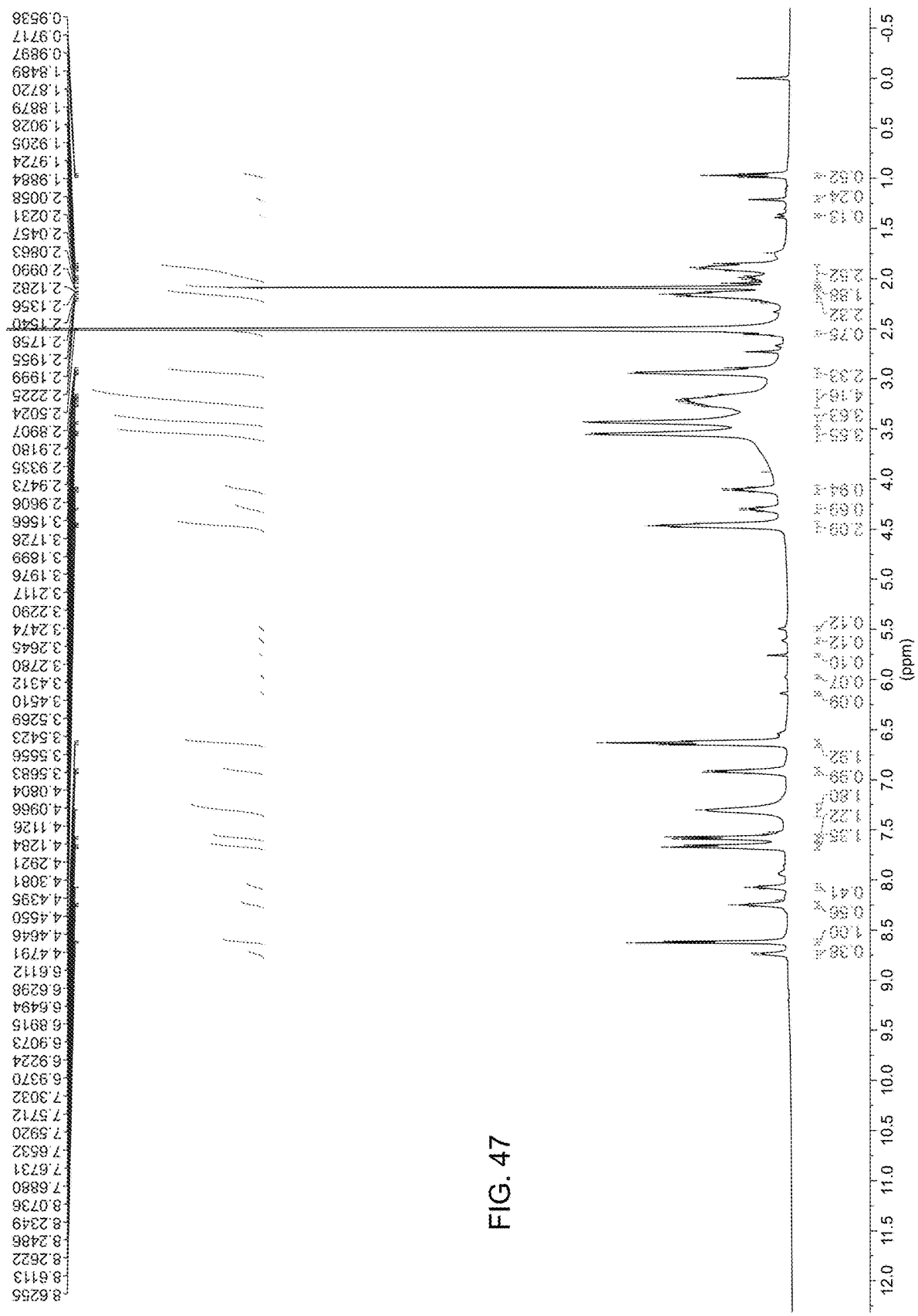

FIG. 47: [Example 30 Compound 31] NMR data of $N^2$-(4-(((2-amino-4-oxo-3,4-dihydropteridin-6-yl)methyl)amino)benzoyl)-$N^5$-(2-(2-aminoethoxy)ethyl)-L-glutamine Bruker BioSpin GmbH; Method Pulse Sequence: zg30. Relaxation Delay: 1 s. Solvent: DMSO-$d_6$. Temperature: ~298.097 K. Number of Scans: 64. Frequency: 400.132470966543 MHz. Nucleus: 1H.

Figure 48:
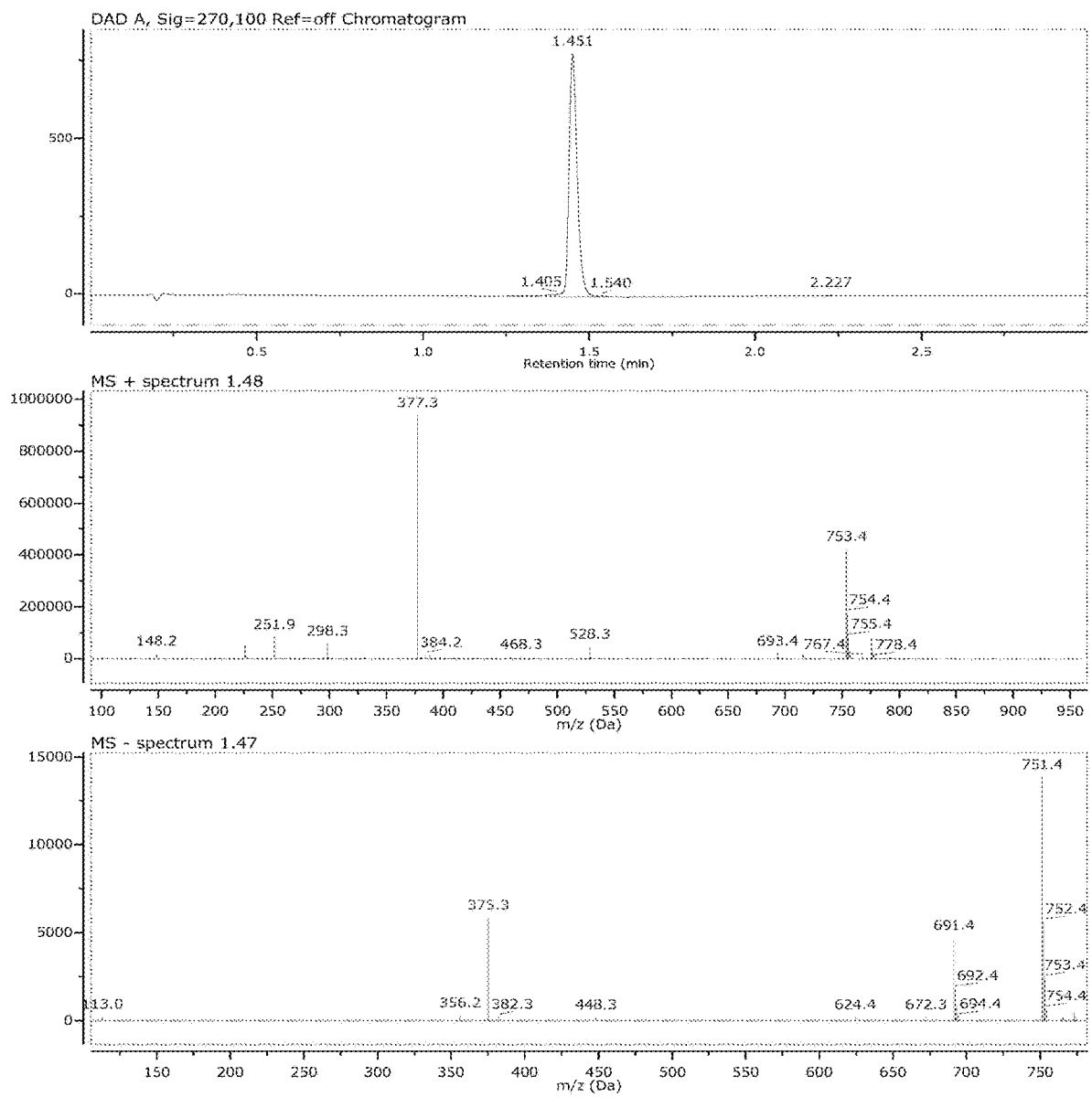

FIG. 48: [Example 31 Compound 32] LCMS and Mass data of $N^2$-(4-(((2-amino-4-oxo-3,4-dihydropteridin-6-yl)methyl)amino)benzoyl)-$N^5$-(2-(2-(3-(3,3,6,6-tetramethyl-1-oxido-4,5-didehydro-2,3,6,7-tetrahydro-1$\lambda^6$-thiepin-1-ylidene)ureido)ethoxy)ethyl)-L-glutamine.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 49:
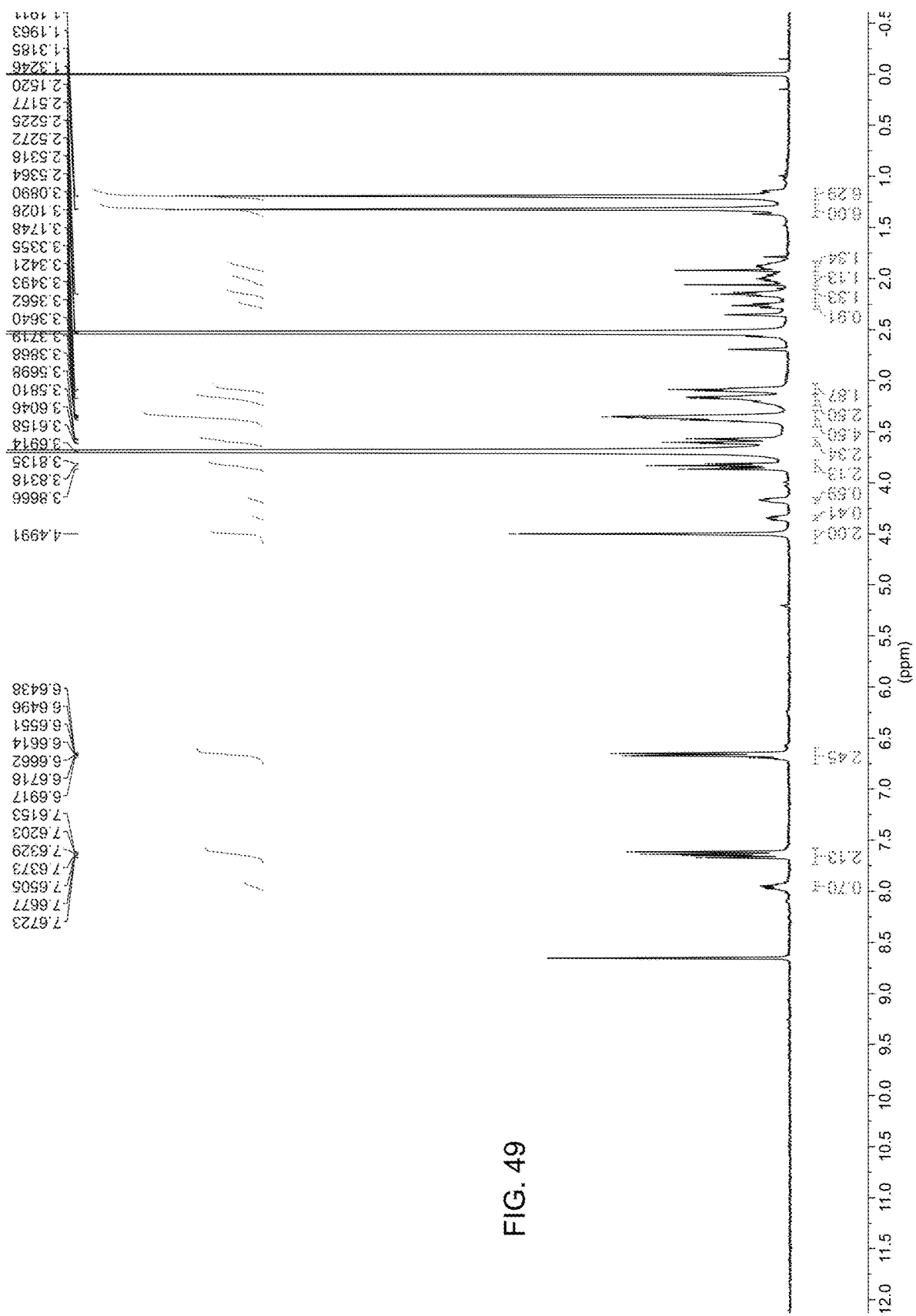

FIG. 49: [Example 31 Compound 32] NMR data of $N^2$-(4-(((2-amino-4-oxo-3,4-dihydropteridin-6-yl)methyl)amino)benzoyl)-$N^5$-(2-(2-(3-(3,3,6,6-tetramethyl-1-oxido-4,5-didehydro-2,3,6,7-tetrahydro-1$\lambda^6$-thiepin-1-ylidene)ureido)ethoxy)ethyl)-L-glutamine.

Bruker BioSpin GmbH; Method Pulse Sequence: zg30. Relaxation Delay: 1 s. Solvent: DMSO-$d_6$. Temperature: ~298.097 K. Number of Scans: 128. Frequency: 400.132470966543 MHz. Nucleus: 1H.

Figure 50:
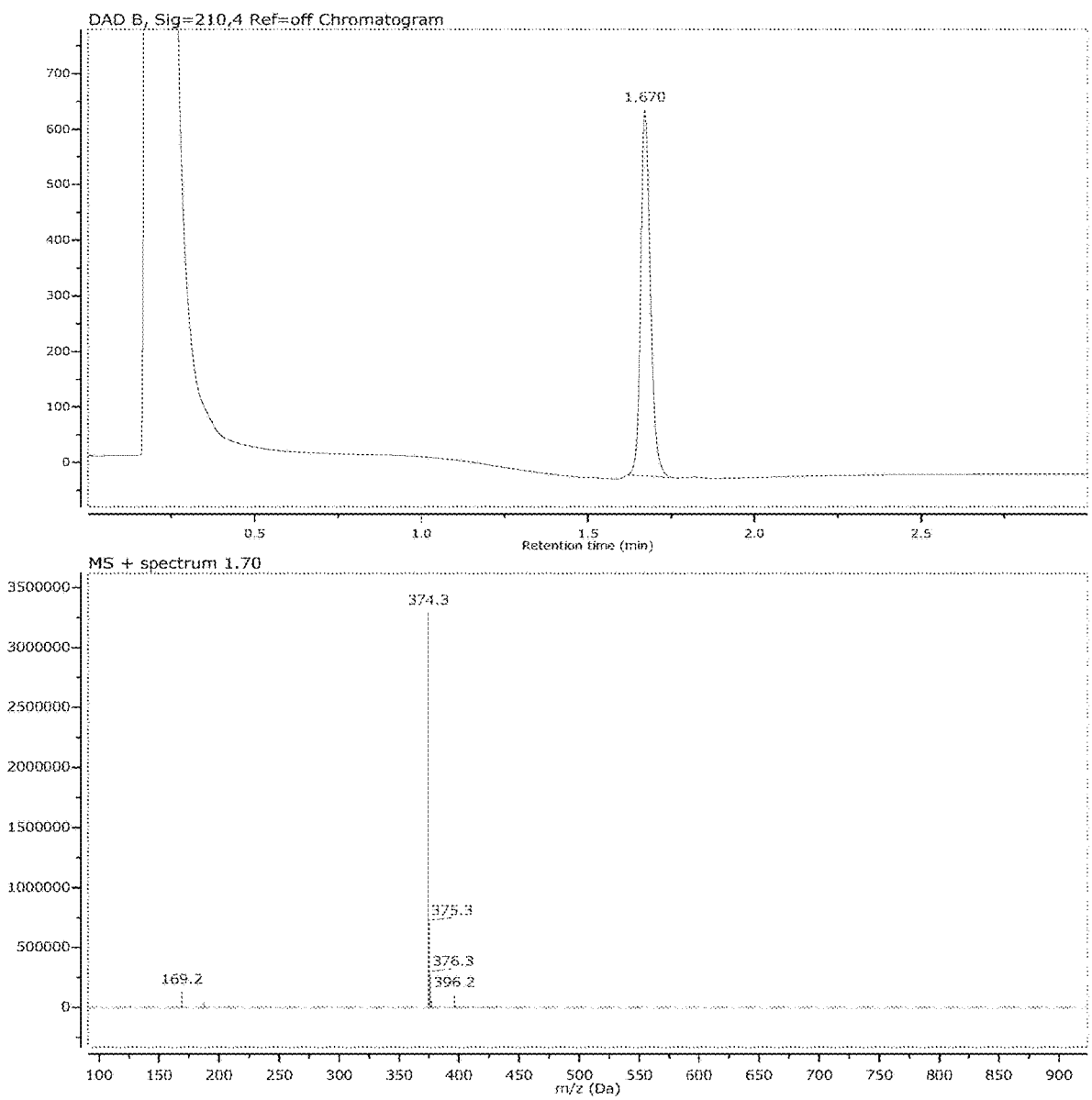

FIG. 50: [Example 33 Compound 34] LCMS and Mass data of 1-(2-(2-(2-aminoethoxy)ethoxy)ethyl)-3-(3,3,6,6-tetramethyl-1-oxido-4,5-didehydro-2,3,6,7-tetrahydro-1$\lambda^6$-thiepin-1-ylidene)urea.

Column: Waters XSelect CSH C18 (50×2.1 mm 3.5μ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).

Figure 51:
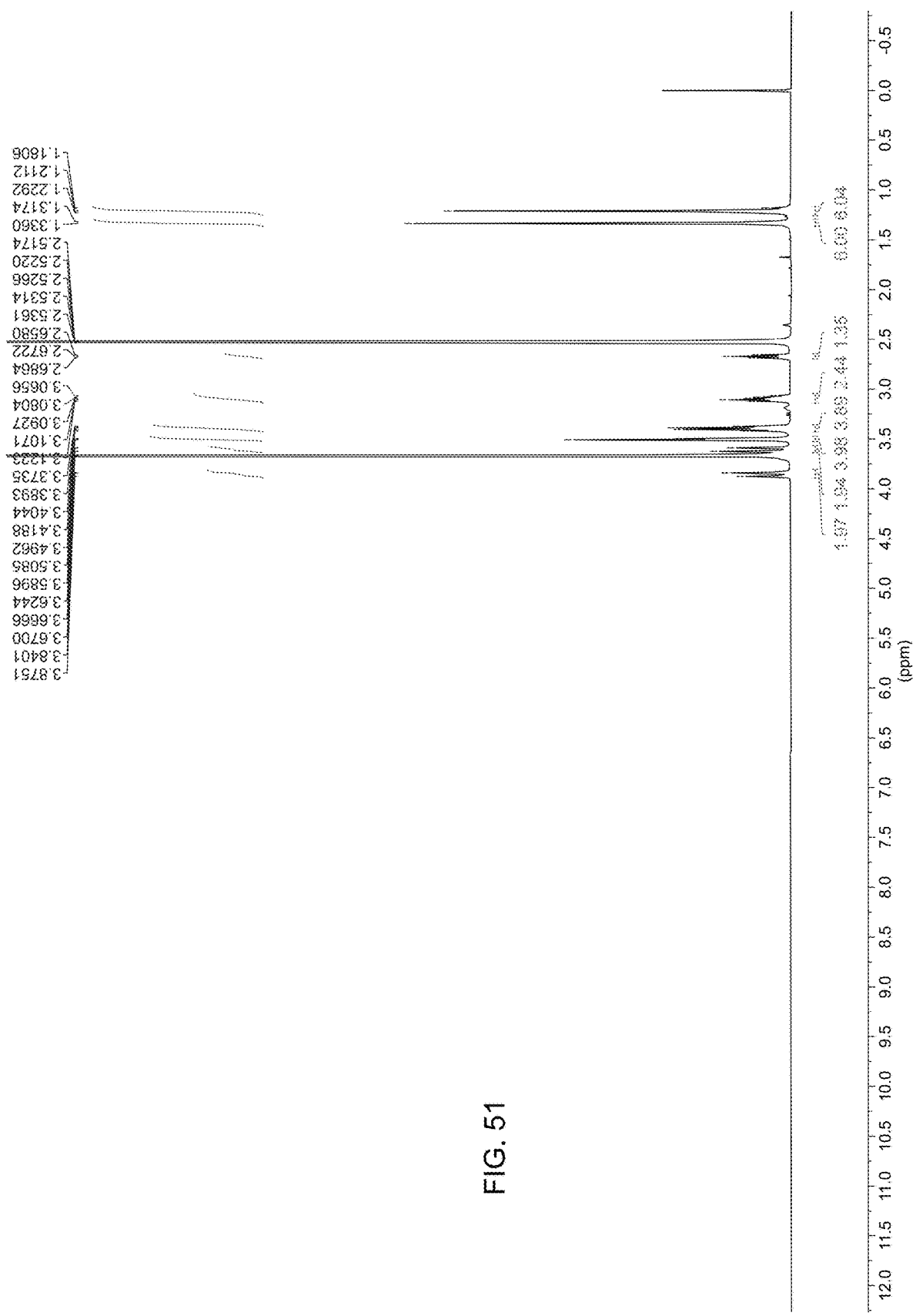

FIG. 51: [Example 33 Compound 34] NMR data of 1-(2-(2-(2-aminoethoxy)ethoxy)ethyl)-3-(3,3,6,6-tetramethyl-1-oxido-4,5-didehydro-2,3,6,7-tetrahydro-1$\lambda^6$-thiepin-1-ylidene)urea.

Bruker BioSpin GmbH; Method Pulse Sequence: zg30. Relaxation Delay: 1 s. Solvent: DMSO-$d_6$. Temperature: ~297.86 K. Number of Scans: 128. Frequency: 400.232471584084 MHz. Nucleus: 1H.

Figure 52:
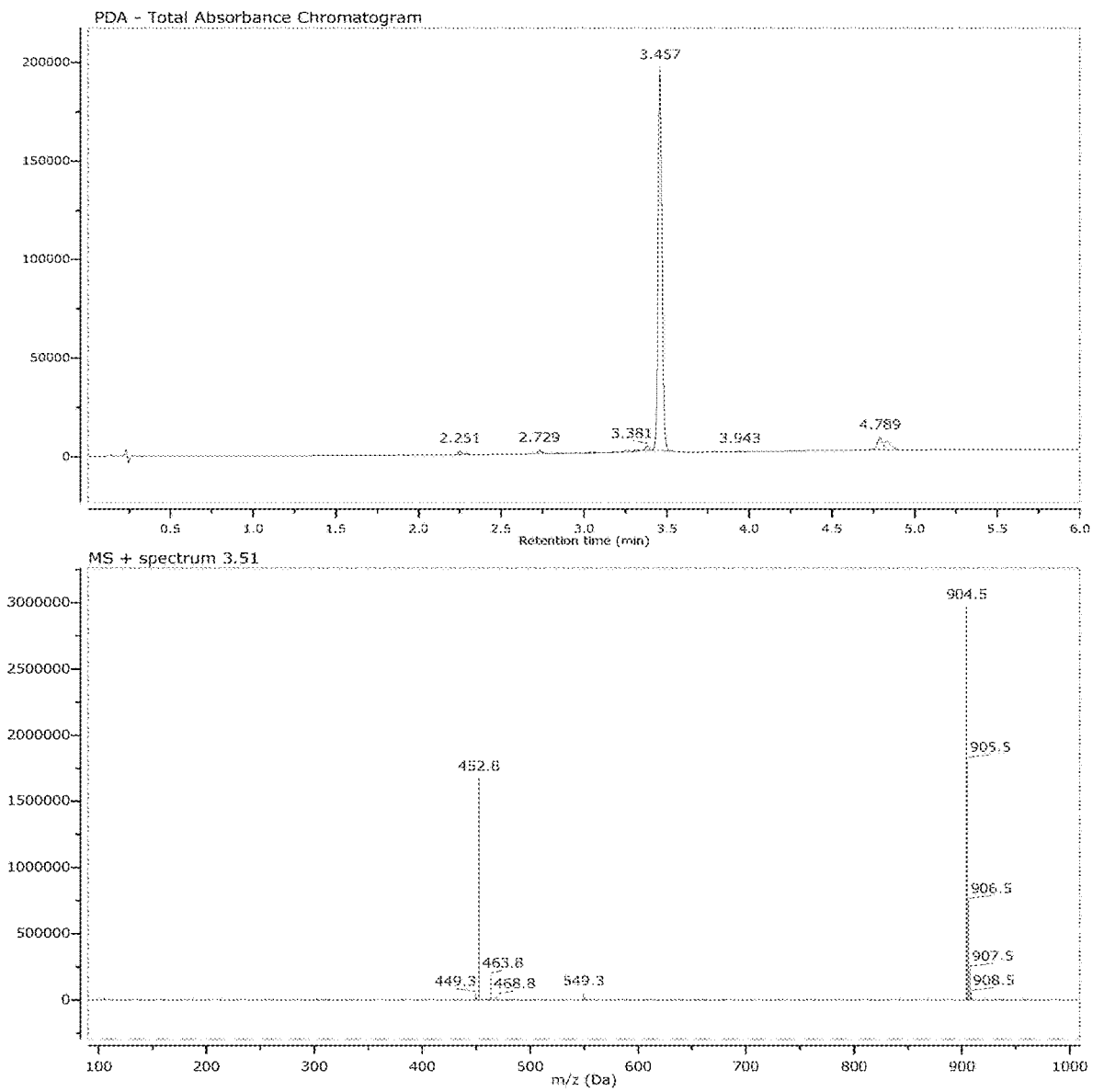

FIG. 52: [Example 34 Compound 35] LCMS and Mass data of 1-(2-(2-(2-aminoethoxy)ethoxy)ethyl)-3-(3,3,6,6-tetramethyl-1-oxido-4,5-didehydro-2,3,6,7-tetrahydro-1$\lambda^6$-thiepin-1-ylidene)urea-Cy7 adduct formate salt.

Column: Waters XSelect CSH C18 (50×2.1 mm, 3.5μ). Flow: 0.8 ml/min; Column temp: 35° C. Eluent A: 0.1% Formic acid in acetonitrile. Eluent B: 0.1% Formic acid in water. Lin. Gradient: t=0 min 5% A, t=3.5 min 98% A, t=6 min 98% A. Post time: 2 min. Detection DAD (220-320 nm, 210 and 220 nm). Detection: PDA (210-800 nm). Detection: MSD ESI pos/neg (mass range: 100-1000). Detection: ELSD (Alltech 3300): gas flow 1.5 ml/min, gas temp: 40° C.

Figure 53:
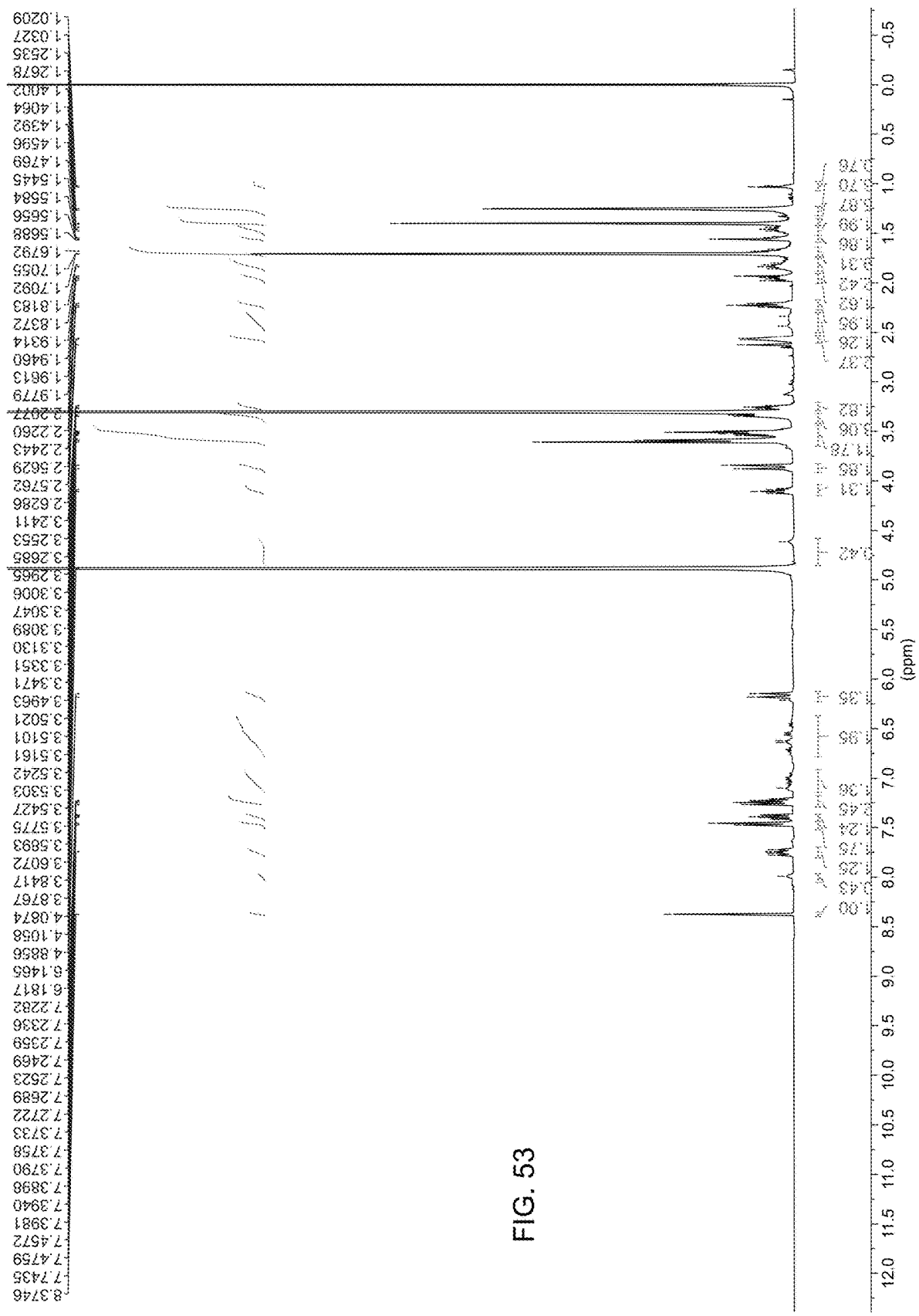

FIG. 53: [Example 34 Compound 35] NMR data of 1-(2-(2-(2-aminoethoxy)ethoxy)ethyl)-3-(3,3,6,6-tetramethyl-1-oxido-4,5-didehydro-2,3,6,7-tetrahydro-1$\lambda^6$-thiepin-1-ylidene)urea-Cy7 adduct formate salt.

Bruker BioSpin GmbH; Method Pulse Sequence: zg30. Relaxation Delay: 1 s. Solvent: MeOD. Temperature: ~296.1649 K. Number of Scans: 64. Frequency: 400.132470966543 MHz. Nucleus: 1H.

Figure 54:
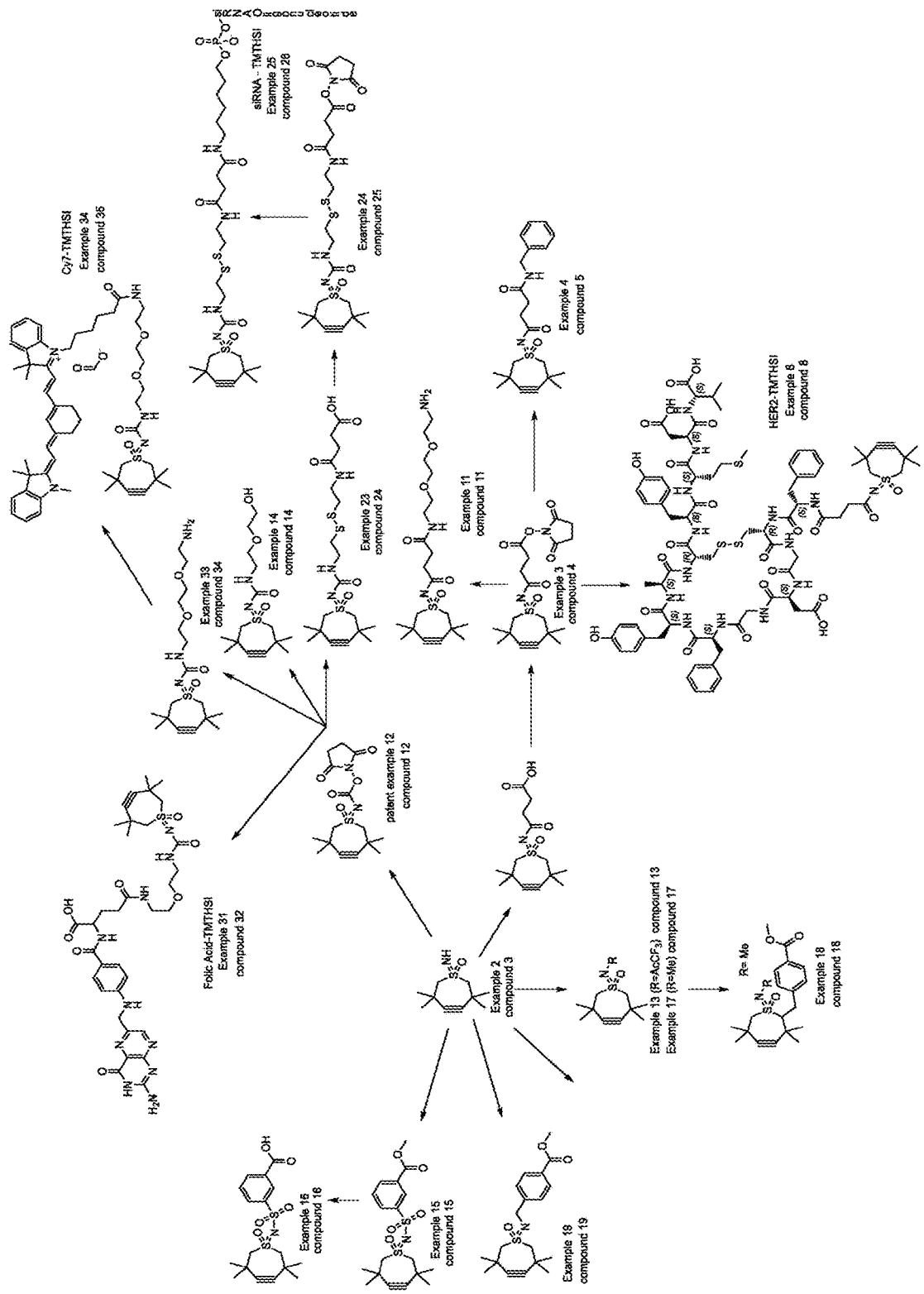
Figure 55:
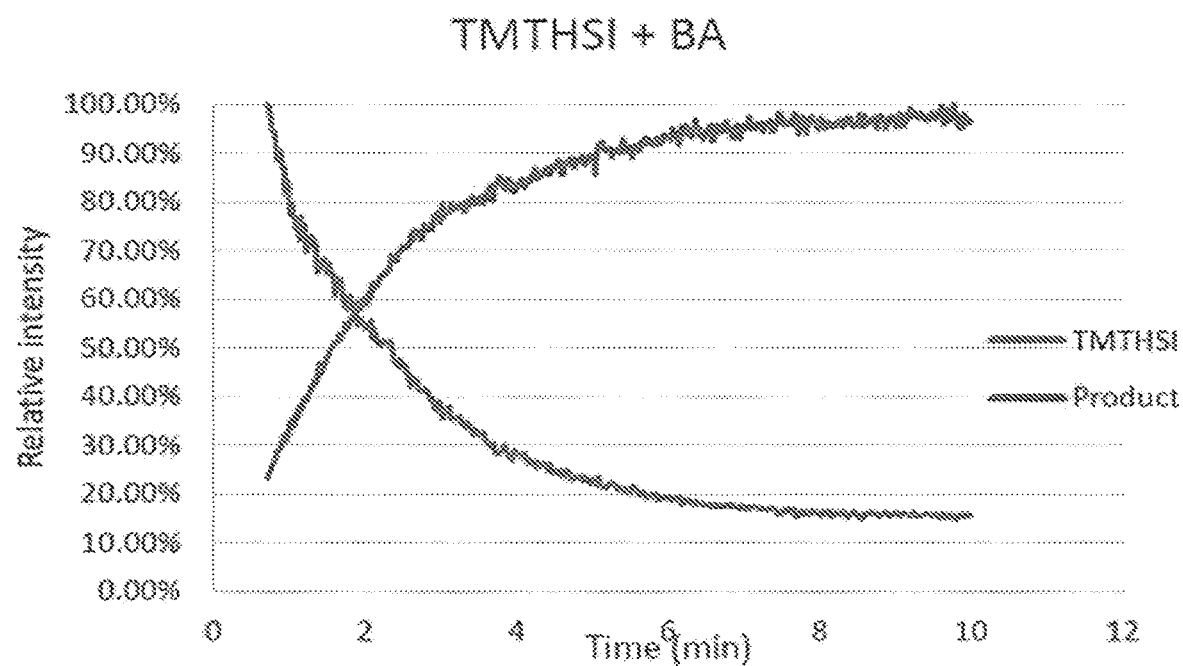

FIG. 54: Overview of generated 1-imino-3,3,6,6-tetramethyl-4,5-didehydro-2,3,6,7-tetrahydro-1H-1$\lambda^6$-thiepine 1-oxide (TMTHSI) derivatives according to the invention FIG. 55: Reaction kinetics of TMTHSI with Benzyl azide to determine reaction rate constant value kt.

FIG. 56: UPLC Chromatograms of:
A) siRNA PLK1 oligonucleotide reference
B) Complete conversion of amino modified siRNA PLK1 to TMTHSI functionalised siRNA PLK1 oligonucleotide, Example 25, Compound 26
C) Complete conversion of TMTHSI-functionalised siRNA oligonucleotide in a reaction with azide functionalised CPP1 peptide, yielding CPP1-siRNA PLK1 conjugate, Example 26, Compound 27
D) complete conversion of acid labile linker NHS ester in a reaction with amine-CPP1-siRNA conjugate, yielding L7-CPP1-siRNA PLK1 conjugate, Example 27, Compound 28

DETAILED DESCRIPTION OF THE INVENTION

Definitions

The verb "to comprise" as is used in this description and in the claims and its conjugations is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there is one and only one of the elements. The indefinite article "a" or "an" thus usually means "at least one".

The compounds disclosed in this description and in the claims may be described as thiocycloheptyne compounds, i.e. cycloheptyne compounds wherein a combination of a sulfur and a triple bond is present in the ring structure. The triple bond of the cycloheptyne moiety may be located on either one of the three possible locations, relative to the sulfur (numbering according to "IUPAC Nomenclature of Organic Chemistry", Rule A31.2). The description of any cycloheptyne compound in this description and in the claims is meant to include all three individual regioisomers of the cycloheptyne moiety.

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise.

The compounds disclosed in this description and in the claims may further exist as exo and endo regioisomers. Unless stated otherwise, the description of any compound in the description and in the claims is meant to include both the individual exo and the individual endo regioisomer of a compound, as well as mixtures thereof.

Furthermore, the compounds disclosed in this description and in the claims may exist as cis and trans isomers. Unless stated otherwise, the description of any compound in the description and in the claims is meant to include both the individual cis and the individual trans isomer of a compound, as well as mixtures thereof. As an example, when the structure of a compound is depicted as a cis isomer, it is to be understood that the corresponding trans isomer or mixtures of the cis and trans isomer are not excluded from the invention of the present application.

Unsubstituted alkyl groups have the general formula $C_nH2_{n+1}$ and may be linear or branched. Unsubstituted alkyl groups may also contain a cyclic moiety, and thus have the concomitant general formula $C_nH2_{n-1}$. Optionally, the alkyl groups are substituted by one or more substituents further specified in this document. Examples of suitable alkyl groups include, but are not limited to, methyl, ethyl, propyl, 2-propyl, t-butyl, 1-hexyl, 1-dodecyl and the like.

Unsubstituted alkenyl groups have the general formula $C_nH2_{n-1}$, and may be linear or branched. Examples of suitable alkenyl groups include, but are not limited to, ethenyl, propenyl, isopropenyl, butenyl, pentenyl, decenyl, octadecenyl, and eicosenyl and the like. Unsubstituted alkenyl groups may also contain a cyclic moiety, and thus have the concomitant general formula $C_nH2_{n-3}$.

Unsubstituted alkenes have the general formula $C_nH2_n$ whereas unsubstituted alkynes have the general formula $C_nH2_{n-2}$ Aryl groups comprise at least six carbon atoms and may include monocyclic, bicyclic and polycyclic structures. Optionally, the aryl groups may be substituted by one or more substituents further specified in this document. Examples of aryl groups include groups such as for example phenyl, naphthyl, anthracyl and the like.

Arylalkyl groups and alkylaryl groups comprise at least seven carbon atoms and may include monocyclic and bicyclic structures. Optionally, the aryl groups may be substituted by one or more substituents further specified in this document. An arylalkyl group is for example benzyl and the like. An alkylaryl group is for example 4-t-butylphenyl and the like.

Where an aryl group is denoted as a (hetero)aryl group, the notation is meant to include an aryl group and a heteroaryl group. Similarly, an alkyl(hetero) aryl group is meant to include an alkylaryl group and a alkylheteroaryl group, and (hetero) arylalkyl is meant to include an arylalkyl group and a heteroarylalkyl group.

A heteroaryl group comprises one to four heteroatoms selected from the group consisting of oxygen, phosphor, nitrogen and sulphur.

Compounds

With the thiocycloheptyne compounds of de Almeida as a starting point, the present inventors set out to find improved compounds that could be used in copper free click reactions. TMTH itself was found not suitable for practical use due to an inherent instability (Dommerholt et al. Nature Communications 5, Article number: 5378 (2014)). Derivatisation of the sulphur in the TMTH ring structure via direct alkylation has been described in King et al. (Chem.Comm., 2012, 9308-9309). Other derivatisations are described as not being straightforward due to the observation already made by King that the ring strain should not stretched beyond its limit to impede the reactivity of the alkyne bond. Furthermore, any derivatisation should provide a compound that is suitable for reactions under aqueous conditions (a high reactivity) and tolerate biological media in subsequent applications to yield a suitable bioorthogonal reagent.

The present inventors have now surprisingly found that other derivatisations at the sulphur are possible. The resulting compounds combine a high reactivity in cycloadditions with a good relative stability. The sulfonimines (>S(=O) (=NH) and/or sulfonediimines (>S(=NR)2) of the invention are a novel class of compounds that can be used as bioorthogonal labelling or conjugation agents. The sulfonimines and/or sulfonediimines of the present invention can be easily derivatised with other functional groups and linkers using known chemistries and can be further functionalised, for instance for bioorthogonal labelling, imaging or modification such as surface modification of target molecules. The compounds of the invention can be conjugated to a wide variety of bioactive compounds and/or drug delivery systems.

TMTH and TMTH derivatives published in King et al. (Chem.Comm., 2012, 9308-9309) have shown poor stability and could not been used as such in further synthesis (Li, Molecules, 2016, 21, 1393, Krebs, Tet. Lett., 1970, 761-764). TMTHSI compounds and derivatives according to the present invention however can be synthesized and isolated and are stable to both basic, and acidic purification and as such can be used for further synthesis. TMTHSI and TMTHSI derivatives thereof according to the invention have proven prolonged shelve life over a year, as is demonstrated in the examples. TMTHSI and TMTHSI derivatives can be reacted with azides in acidic/neutral/basic aqueous environment and combinations thereof with organic solvents.

In a first aspect, the in invention therefore relates to a compound of Formula (I)

(I)

wherein:
n and m are independently 0, 1, or 2 and n+m is 2;
X is O or NR$^9$,
Y is NR$^{10}$,
R$^1$, R$^2$, R$^3$, R$^4$ are independently selected from the group consisting of hydrogen, halogen (F, CL, Br, I), O, N, P and S, C$_1$-C$_{24}$ alkyl groups, C$_6$-C$_{24}$ (hetero)aryl groups, C$_7$-C$_{24}$ alkyl(hetero)aryl groups and C$_7$-C$_{24}$ (hetero)arylalkyl groups, wherein the O, N, P, and S are further independently coupled to hydrogen, halogen (F, CL, Br, I), $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, the alkyl groups optionally being interrupted by one of more hetero-atoms selected from the group consisting of O, N, P and S, wherein the alkyl groups, (hetero)aryl groups, alkyl(hetero)aryl groups and (hetero)arylalkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, CL, Br, I), amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S, wherein the silyl groups are represented by the formula $(R^{11})_3Si—$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S;

$R^5$, $R^6$, $R^7$, $R^8$ are independently selected from the group consisting of hydrogen, halogen (F, CL, Br, I), O, N, P and S, $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups, wherein the O, N, P, and S are further independently coupled to hydrogen, halogen (F, CL, Br, I), $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, the alkyl groups optionally being interrupted by one of more hetero-atoms selected from the group consisting of O, N, P and S, wherein the alkyl groups, (hetero)aryl groups, alkyl(hetero)aryl groups and (hetero)arylalkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, CL, Br, I), amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S, wherein the silyl groups are represented by the formula $(R^{11})_3Si—$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S;

wherein, optionally, R1 and R7, R1 with R8, R2 with R7, R2 with R8, R3 with R5, R3 with R6, R4 with R5, and/or R4 with R6 independently form fused ring systems such as cycloalkyl-, cyclo(hetero)aryl-, cycloalkyl(hetero)aryl, -cyclo(hetero)arylalkyl systems, wherein the alkyl groups of the fused ring systems optionally being interrupted by one of more hetero-atoms selected from the group consisting of O, N, P and S, wherein the alkyl groups, (hetero)aryl groups, alkyl(hetero)aryl groups and (hetero)arylalkyl groups of the fused systems are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S, wherein the silyl groups are represented by the formula $(R^{11})_3Si—$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the alkyl groups, alkenyl groups, alkynyl groups, cycloalkyl groups, alkoxy groups, alkenyloxy groups, alkynyloxy groups and cycloalkyloxy groups are optionally substituted, the alkyl groups, the alkoxy groups, the cycloalkyl groups and the cycloalkoxy groups being optionally interrupted by one of more hetero-atoms selected from the group consisting of O, N, P and S;

$R^9$, $R^{10}$ are independently selected from the group consisting of hydrogen, halogen (F, CL, Br, I), $R^{12}$, —CH=C$(R^{12})_2$, —C≡C$R^{12}$, —[C$(R^{12})_2$C$(R^{12})_2$O]$_q$—$R^{12}$, wherein q is in the range of 1 to 200, —CN, —$N_3$, —NCX, —XCN, —X$R^{12}$, —N$(R^{12})_2$, —$^+$N$(R^{12})_3$, —C(X)N$(R^{12})_2$, —C$(R^{12})_2$X$R^{12}$, —C(X)$R^{12}$, —C(X)X$R^{12}$, —S(O)$R^{12}$, —S(O)$_2R^{12}$, —S(O)O$R^{12}$, —S(O)$_2$O$R^{12}$, —S(O)N$(R^{12})_2$, —S(O)$_2$N$(R^{12})_2$, —OS(O)$R^{12}$, —OS(O)$_2R^{12}$, —OS(O)O$R^{12}$, —OS(O)$_2$O$R^{12}$, —P(O)$(R^{12})$(O$R^{12}$), —P(O)(O$R^{12})_2$, —OP(O)(O$R^{12})_2$, —Si$(R^{12})_3$, —XC(X)$R^{12}$, —XC(X)X$R^{12}$, —XC(X)N$(R^{12})_2$, —N$(R^{12})$C(X)$R^{12}$, —N$(R^{12})$C(X)X$R^{12}$ and —N$(R^{12})$C(X)N$(R^{12})_2$, wherein X is oxygen or sulphur and wherein $R^{12}$ is independently selected from the group consisting of hydrogen, halogen (F, CL, Br, I), $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups.

In a preferred embodiment, the integers n and in are both 1 and the compound is of Formula (II):

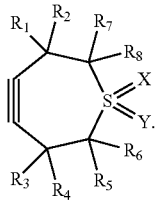
(II)

R¹-R⁸, X, Y are as defined herein elsewhere. Preferably the alkyne is located at the 4-5 position relative to the sulphur (1-position). The resulting thiocycloheptyne is a symmetric compound with a symmetry axis through the sulphur and the alkyne bond. Compared to the known BCN compound that contains both cis-trans isomerism and is chiral (E/Z), the current TMTHSI-compound expresses only E/Z isomerism, but further remains identical. Using symmetric thiocycloheptynes in the application as a click reaction reagents avoids having mixtures of isomeric compounds with potentially physicochemical or biological variable behaviour.

In a preferred embodiment, X is O. The resulting sulfonimides, have been successfully prepared with good stability and have been successfully derivatised as shown in the examples.

In a preferred embodiment, $R^{10}$ is H or comprises a functional group selected from the group consisting of an alcohol, amine, ester, C1-4 alkyl, carboxylic acid, trifluoroacetyl and a n-hydroxysuccinimide (NHS) ester.

In a preferred embodiment, $R^{10}$ is H. The resulting S(=O)NH functionality is stable and has a good reactivity at the NH position for further derivatisation.

In a preferred embodiment, $R^1$, $R^2$, $R^3$, $R^4$ are independently selected from the group consisting of H, halogen (F, CL, Br, I) and $C_1$-$C_4$ alkyl, preferably methyl or ethyl, or $R^1$ with $R^2$ and/or $R^3$ with $R^1$ form a $C_3$-$C_6$-cycloalkyl, preferably a cyclopropyl. In a further preferred embodiment, $R^1$, $R^2$, $R^3$, $R^4$ are independently selected from the group consisting of $C_1$-$C_4$ alkyl, preferably methyl or ethyl.

In a further preferred embodiment $R^1$, $R^2$, $R^3$, $R^4$ are identical and selected from the group consisting of H, halogen and $C_1$-$C_4$ alkyl, or $R^1$ with $R^2$ and $R^3$ with $R^4$ form a $C_3$-$C_6$-cycloalkyl, preferably a cyclopropyl. In a further preferred embodiment, $R^1$, $R^2$, $R^3$, $R^4$ are identical and selected from the group consisting of H, $C_1$-$C_4$ alkyl, preferably methyl or ethyl (preferably methyl), or $R^1$ with $R^2$ and $R^3$ with $R^4$ form a cyclopropyl. In a further preferred embodiment, $R^1$, $R^2$, $R^3$, $R^4$ are identical and selected from the group consisting of $C_1$-$C_4$ alkyl, preferably methyl or ethyl, most preferably methyl.

In one embodiment, $R^1$, $R^2$, $R^3$, $R^4$, $R^5$, $R^6$, $R^7$, $R^8$ are independently H, halogen (F, CL, Br, I) or $C_1$-$C_{24}$ alkyl, and preferably independently H or lower alkyl, i.e. $C_1$-$C_4$ alkyl, i.e. methyl, ethyl, propyl isopropyl, n-butyl, isobutyl or tert-butyl. In a particularly preferred embodiment, $R^1$-$R^4$ are the same lower alkyl. In a more preferred embodiment, $R^1$-$R^4$ are all methyl.

In a preferred embodiment, $R^5$, $R^6$, $R^7$, $R^8$ are independently selected from the group consisting of H, halogen (F, CL, Br, I) and $C_1$-$C_4$ alkyl. More preferably, $R^5$, $R^6$, $R^7$, $R^8$ are identical and selected from the group consisting of H, halogen (F, CL, Br, I) and $C_1$-$C_4$ alkyl, preferably methyl or ethyl. More preferably, $R^5$, $R^6$, $R^7$, $R^8$ are identical and selected from the group consisting of H and $C_1$-$C_4$ alkyl, preferably methyl or ethyl. In one embodiment, $R^5$-$R^8$ are all H.

In a particularly preferred embodiment, the compound of formula (I) is 1-imino-3,3,6,6-tetramethyl-4,5-didehydro-2,3,6,7-tetrahydro-1H-1λ6-thiepine 1-oxide of Formula (III):

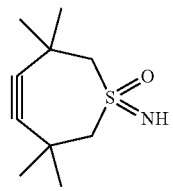

3

Synthesis

In another aspect, the invention pertains to the synthesis of the compounds of the invention and in particular to a method for the preparation of a compound of Formula (I), the method comprising the steps of:

a. converting bishydrazone (2) to an iminodidehydrosulfonimino (3);

b. isolating the resulting an iminodidehydrosulfonimino (3).

The synthesis is based partly on the synthesis of TMTH by Almeida et al., with as an intermediate product in the TMTH synthesis a thiopanedione 1 that in the present invention is followed by a one-step conversion of the bishydrazone 2 to the sulfonimide 3.

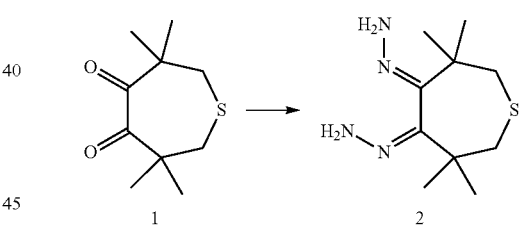

The synthesis of the diketone 1 and bishydrazone 2 has been well described in literature [Almeida at al]. This synthesis starts with the conversion of diketone 1 towards bishydrazone 2. The reaction is in the presence of one or more hydrazines, preferably hydrazine sulfate and/or hydrazine monohydrate and preferably under pressure.

The resulting bishydrazine 2 is converted into the target compound 3 in a two step oxidation reaction. One step is of the conversion comprises an oxidation reaction (addition) wherein the bishydrazone (2) is reacted with an oxidant to oxidise the sulfur (>S) functionality to the sulfonimino (>S(=O)(=NR) functionality. Another step of the conversion is an oxidation reaction (elimination) wherein the bishydrazone (2) is reacted with an oxidant to oxidise the (bis)hydrazine (>C=N—NH2)2 functionality to the alkyne (—C☰C—) functionality. In preferred embodiment, this two step reaction is performed in a one step synthesis, preferably with the same oxidising agent, preferably iodobenzene diacetate:

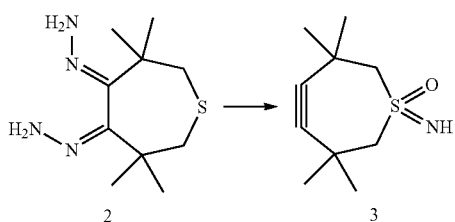

Coupling of Linkers and Functional Groups

In a further aspect of the invention, linkers and/or functional groups are coupled to the functionalised thiocycloheptyne of the invention. Thus, in a further aspect, the invention pertains to a compound wherein X and/or Y and/or one of the atoms in the thiocycloheptyne ring adjacent to the S atom of a compound of Formula (I), independently, are coupled to an optional linking group (L) and a functional group (Q) to yield a compound of Formula (III):

(Formula I)-L-Q;               (III)

wherein the linking group (L) is absent or selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_5$-$C_{24}$ cycloalkynylene groups, $C_7$-$C_{24}$ alkyl(hetero)arylene groups, $C_7$-$C_{24}$ (hetero)arylalkylene groups, $C_5$-$C_{24}$ (hetero)arylalkenylene groups, $C_9$-$C_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkenylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkynyl groups, $C_5$-$C_{12}$ cycloalkynyl groups, $C_8$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogen (F, CL, Br, I) s, amino groups, oxo and silyl groups, wherein the silyl groups can be represented by the formula $(R^{11})_3Si$—, wherein $R^{11}$ is defined as above;

wherein the functional group Q is selected from the group consisting of hydrogen, halogen (F, CL, Br, I), $R^{12}$, —CH=C$(R^{12})_2$, —C≡C$R^{12}$, —[C$(R^{12})_2$C$(R^{12})_2$O]$_q$—$R^{12}$, wherein q is in the range of 1 to 200, —CN, —$N_3$, —NCX, —XCN, —X$R^{12}$, —N$(R^{12})_2$, —$^+$N$(R^{12})_3$, —C(X)N$(R^{12})_2$, —C$(R^{12})_2$X$R^{12}$, —C(X)$R^{12}$, —C(X)X$R^{12}$, —S(O)$R^{12}$, —S(O)$_2R^{12}$, —S(O)O$R^{12}$, —S(O)$_2$O$R^{12}$, —S(O)N$(R^{12})_2$, —S(O)$_2$N$(R^{12})_2$, —OS(O)$R^{12}$, —OS(O)$_2R^{12}$, —OS(O)O$R^{12}$, —OS(O)$_2$O$R^{12}$, —P(O)$(R^{12})$(O$R^{12}$), —P(O)(O$R^{12})_2$, —OP(O)(O$R^{12})_2$, —Si$(R^{12})_3$, —XC(X)$R^{12}$, —XC(X)X$R^{12}$, —XC(X)N$(R^{12})_2$, —N$(R^{12})$C(X)$R^{12}$, —N$(R^{12})$C(X)X$R^{12}$ and —N$(R^{12})$C(X)N$(R^{12})_2$, wherein X is oxygen or sulphur and wherein $R^{12}$ is independently selected from the group consisting of hydrogen, halogen (F, CL, Br, I), $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups. Preferably $R^{12}$ is hydrogen or $C_1$-$C_6$ alkyl.

If the optional linking group (L) and functional group (Q) are attached to one of the atoms in the thiocycloheptyne ring adjacent to the S atom, one of $R^5$, $R^6$, $R^7$ or $R^8$ is replaced by the optional linking group (L) attached to functional group (Q). If the optional linking group (L) and functional group (Q) are attached to X or Y, R9 or R10, respectively, are replaced by the optional linking group (L) attached to functional group (Q).

Preferably optional linking group (L) and functional group (Q) are attached to one of X or Y, preferably to Y, and/or to one of the atoms in the thiocycloheptyne ring adjacent to the S atom. More preferably optional linking group (L) and a functional group (Q) are attached to one of X or Y, preferably to Y.

In one embodiment is provided a compound composed of a compound of formula (I) according to the invention coupled to an optional linking group (L) and a functional group (Q) at atom X or Y, preferably Y, and/or at one of one of the atoms in the thiocycloheptyne ring adjacent to the S atom to yield a compound of Formula (III):

(Formula I)-L-Q               (III), wherein the linking group (L) is absent or selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_5$-$C_{24}$ cycloalkynylene groups, $C_7$-$C_{24}$ alkyl(hetero)arylene groups, $C_7$-$C_{24}$ (hetero)arylalkylene groups, $C_5$-$C_{24}$ (hetero)arylalkenylene groups, $C_9$-$C_{24}$ (hetero)arylalkynylene groups, the alkylene groups, alkenylene groups, alkynylene groups, cycloalkylene groups, cycloalkenylene groups, cycloalkynylene groups, alkyl(hetero)arylene groups, (hetero)arylalkylene groups, (hetero)arylalkenylene groups and (hetero)arylalkynylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_5$-$C_{12}$ cycloalkynyl groups, $C_8$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogen (F, CL, Br, I) s, amino groups, oxo and silyl groups, wherein the silyl groups can be represented by the formula $(R^{11})_3Si$—, wherein $R^{11}$ is defined as above;

wherein the functional group Q is selected from the group consisting of hydrogen, halogen (F, CL, Br, I), $R^{12}$, —CH=C$(R^{12})_2$, —C≡C$R^{12}$, —[C$(R^{12})_2$C$(R^{12})_2$O]$_q$—$R^{12}$, wherein q is in the range of 1 to 200, —CN, —$N_3$, —NCX, —XCN, —X$R^{12}$, —N$(R^{12})_2$, —$^+$N$(R^{12})_3$, —C(X)N$(R^{12})_2$, —C$(R^{12})_2$X$R^{12}$, —C(X)$R^{12}$, —C(X)X$R^{12}$, —S(O)$R^{12}$, —S(O)$_2R^{12}$, —S(O)O$R^{12}$, —S(O)$_2$O$R^2$, —S(O)N$(R^{12})_2$, —S(O)$_2$N$(R^{12})_2$, —OS(O)$R^{12}$, —OS(O)$_2R^{12}$, —OS(O)O$R^{12}$, —OS(O)$_2$O$R^{12}$, —P(O)$(R^{12})$(O$R^{12}$), —P(O)(O$R^{12})_2$, —OP(O)(O$R^{12})_2$, —Si$(R^{12})_3$, —XC(X)$R^{12}$, —XC(X)X$R^{12}$, —XC(X)N$(R^{12})_2$, —N$(R^{12})$C(X)$R^{12}$, —N$(R^{12})$C(X)X$R^{12}$ and —N$(R^{12})$C(X)N$(R^{12})_2$, wherein X is oxygen or sulphur and wherein $R^{12}$ is independently selected from the group consisting of hydrogen, halogen (F, CL, Br, I), $C_1$-$C_{24}$ alkyl groups, $C_6$-$C_{24}$ (hetero)aryl groups, $C_7$-$C_{24}$ alkyl(hetero)aryl groups and $C_7$-$C_{24}$ (hetero)arylalkyl groups.

A wide variety of linkers can be used and the selection of linkers can be based on other criteria, for instance in relation to the final applications essentially as disclosed herein elsewhere.

In a preferred embodiment, L is absent or selected from a —[C$(R^{12})_2$C$(R^{12})_2$O]$_q$—$R^{12}$, wherein q is in the range of 1 to 200, —CN, —NCX, —XCN, —X$R^{12}$, —N$(R^{12})_2$, —$^+$N$(R^{12})_3$, —C(X)N$(R^{12})_2$, —C$(R^{12})_2$X$R^{12}$, —C(X)$R^{12}$, —C(X)X$R^{12}$, —S(O)$R^{12}$, —S(O)$_2R^{12}$, —S(O)O$R^{12}$, —S(O)$_2$O$R^{12}$, —S(O)N$(R^{12})_2$, —S(O)$_2$N$(R^{12})_2$, —OS(O)$R^{12}$, —OS(O)$_2R^{12}$, —OS(O)O$R^{12}$, —OS(O)$_2$O$R^{12}$, —P(O)$(R^{12})$(O$R^{12}$), —P(O)(O$R^{12})_2$, —OP(O)(O$R^{12})_2$, —Si$(R^{12})_3$, —XC(X)$R^{12}$, —XC(X)X$R^{12}$, —XC(X)N$(R^{12})_2$, —N$(R^{12})$ C(X)R$^{12}$, —N(R$^{12}$)C(X)XR$^{12}$ and —N(R$^{12}$)C(X)N(R$^{12}$)$_2$, wherein X is oxygen or sulphur and wherein R$^{12}$ is as defined elsewhere.

In a further preferred embodiment, L is absent or is a chain with a length of 1-25 atoms, preferably 1-15 atoms and comprises one or more, preferably 1-6, moieties independently selected from the group consisting of —S(O)$_2$—, —S—, —S—S—, —C(O)NH—, —NHC(O)—, —C(O)O— and phenylene, whereby said chain length is determined by the number of atoms in the in the longest linear chain of atoms. Said longest linear chain may comprise one or more further heteroatoms such as O, N, S and P. Preferably it may comprise one or more further O atoms. In a preferred embodiment, L comprises 1, 2, 3, 4 or 5 moieties independently selected from the group consisting of —S(O)$_2$—, —S—, —S—S—, —C(O)NH—, —NHC(O)—, —C(O)O— and phenylene. It is further preferred that said chain with a length of 1-25 atoms, preferably 1-15 atoms is not branched, i.e. the chain is linear, optionally with the exception of the heteroatoms in moiety or moieties —S(O)$_2$—, —C(O)NH—, —NHC(O)—, —C(O)O— that are not comprised in the linear chain.

In one embodiment, Q is selected from the group consisting of —OR$^{12}$, —N(R$^{12}$)$_2$, —$^+$N(R$^{12}$)$_3$, —C(O)N(R$^{12}$)$_2$, —C(O)OR$^{12}$, —OC(O)R$^{12}$, —OC(O)OR$^{12}$, —OC(O)N(R$^{12}$)$_2$, —N(R$^{12}$)C(O)R$^{12}$, —N(R$^{12}$)C(O)OR$^{12}$ and —N(R$^{12}$)C(O)N(R$^{12}$)$_2$, wherein R$^{12}$ is as defined herein elsewhere.

In a preferred embodiment, Q comprises an alcohol, amine, thiol, carboxylic ester, carboxylic acid or an activated ester, ketone, aldehyde, nitrile, maleimide, alkene, alkyne, heteroaromate, leaving group and phosphoramidite. In a particularly preferred embodiment, Q is an alcohol, amine, carboxylic ester, carboxylic acid or a N-hydroxysuccinimide (NHS) ester.

In one embodiment, the coupling of linker L and/or functional group Q is at the functionalized sulphur of the thiocycloheptyne, i.e. at the X and/or Y of the S(=X)(=Y) part of the molecule. The coupling is with a functional group, optionally via a linker. The functional group Q can be linked to any molecule of interest.

can be reacted with a compound comprising a 1,3-dipole or a 1,3-(hetero)diene. In certain embodiments, the compound comprising a 1,3-dipole or a 1,3-(hetero)diene is an azide-comprising compound, a nitrone-comprising compound or a nitrile oxide comprising compound. Most preferred is an azide-comprising compound. In embodiments, the azide-comprising compound can be coupled using a copper-free click reaction. The coupling results in a triazole-type structure.

The compound of the invention is a double functional compound having reactive sites at the functionalised sulphur position and at the alkyne functionality. Both functionalities can be independently functionalised, one via the optional linkers (L) and functional groups (Q) and the other functionality via click chemistry. The functionalisation can be independently with a drug (such as a small molecule, genetic material etc.), an antibody, a protein, a peptide, a ligand, an imaging label, a targeting ligand, a delivery agent, a nanoparticle, a carrier.

Thus, in one embodiment, the functional group Q is coupled to one or more of a drug, an antibody, a protein, a peptide, a ligand, an imaging label, a targeting ligand, a delivery agent, a nanoparticle, a carrier, optionally via linker L.

In another embodiment, the alkyne can be coupled to one or more of a drug, an antibody, a protein, a peptide, a ligand, an imaging label, a targeting ligand, a delivery agent, a nanoparticle, a carrier. The coupling of the alkyne is preferably performed via a reaction of the alkyne with a a compound comprising a 1,3-dipole or a 1,3-(hetero)diene. In certain embodiments, the compound comprising a 1,3-dipole or a 1,3-(hetero)diene is an azide-comprising compound, a nitrone-comprising compound or a nitrile oxide comprising compound, more preferably an azide-comprising compound.

Thus the compound of the invention is suitable for creating combinations of two molecules of interest/functional groups via a 1,3-dipole/1,3 (hetero)diene/thiacycloheptyne derivative/(linker)/functional group. Schematically, this general principle of the application of the thiacycloheptyne of the present invention is illustrated in the below table:

| Functional Group/molecule of interest | | | | | Functional Group/molecule of interest |
|---|---|---|---|---|---|
| Drug Antibody Protein peptide Ligand Imaging label Targeting ligand Delivery agent Nanoparticle Carrier | Optional Linker | a 1,3-dipole or a 1,3-(hetero)diene | | Optional Linker | Drug Antibody Protein peptide Ligand Imaging label Targeting ligand Delivery agent Nanoparticle Carrier |

In certain embodiments, Q can be linked to one or more of a drug, an antibody, a protein, a peptide, a ligand, an imaging label, a targeting ligand, delivery agent, a nanoparticle, a carrier, or a combination thereof. The chemistry for such couplings is well developed and the skilled person can select the appropriate coupling chemistry to couple Q to the molecule of interest.

Click Reactions

The alkyne group of the compound of the invention is reactive and can be functionalized using for instance cycloaddition-type reactions. In embodiments, the alkyne group The linkers used may be biodegradable, i.e. are initially stable but over time or under specific circumstances such as physiological circumstances, cleavable.

In certain embodiments, there is a preference for a combination wherein a nanoparticle is coupled via the optional linker/1,3-dipole or 1,3-heterodiene/thiocycloheptyne/optional linker to a functional group/molecule of interest selected from a drug, an antibody, a protein, a peptide, a ligand, an imaging label, a targeting ligand, a delivery agent, a nanoparticle, a carrier. The nanoparticle itself may comprise a drug, an antibody, a protein, a peptide. The preferred 1,3-dipole or 1,3-heterodiene for coupling a nanoparticle to the thiocycloheptyne derivatives of the invention is an azide (N3).

Nanoparticles

Drug delivery systems are increasingly used in pharmaceutical science. Through an elaborate set of derivatisations, drugs can be delivered, targeted, monitored and provided to patients with an increasing effectiveness and efficacy. The use of these drug delivery systems like nanoparticles, proteins, hydrogels, liposomes, antibody-drug conjugates, drug polymer conjugates is developing rapidly in the pharmaceutical sciences.

Pharmaceutical sciences are using these systems to reduce toxicity and side effects of drugs, improve delivery and adding imaging ligand s aids in the monitoring of the effectiveness.

Nanoparticles, typically having diameters of <100 nm have been made from a wide variety of materials and anticipated applications in medicine include drug delivery, both in vitro and in vivo diagnostics, nutraceuticals and production of improved biocompatible material. Nanoparticles can be customised for particular purposes ad a wide variety of materials is available. Most pharmaceutically interesting nanoparticles are based on (bio)polymeric materials that can be in a variety of forms. Source materials may be of biological origin like phospholipids, lipids, lactic acid, dextran, chitosan, or have more "chemical" characteristics like various (co)polymers. These nanoparticles are typically functionalised by connecting, coupling, binding (covalenty) active ingredients (drugs, ligand, imaging ligands etc.). The functionalisation of many of these nanoparticles can be achieved by a wired variety of chemistries such as copper free click chemistry using the thiocycloheptyne derivatives of the present invention.

In certain embodiments, the nanoparticle is a self assembling polymeric micelle, preferably from thermosensitive block copolymers. Particularly, copolymers based on PEG-b-poly(N-hydroxyalkyl methacrylamide-oligolactates) with partially methacrylated oligolactate units are preferred, but also other (meth)acrylamide esters can be used to construct the thermosensitive block, e.g. esters, and optionally (oligo) lactate esters, of HPMAm (hydroxypropyl methacrylamide) and HEMAm (hydroxyethylmethacrylamide), and N-(meth) acryloyl amino acid esters. Also preferred thermo-sensitive block copolymers are derived from monomers containing functional groups which may be modified by derivatised and underivatised methacrylate groups, such as HPMAm-lactate polymers; that is, this modification encompassing the incorporation of linker moieties.

Other types of functional thermosensitive (co)polymers, which can be used, are hydrophobically modified poly(N-hydroxyalkyl) (meth)acrylamides, copolymer compositions of N-isopropylacrylamide (NIPAAm) with monomers containing reactive functional groups (e.g., acidic acrylamides and other moieties such as N-acryloxysuccinimide) or similar copolymers of poly(alkyl) 2-oxazalines, etc. Further preferred thermo-sensitive groups can be based on NIPAAm and/or alkyl-2-oxaxolines, which monomers may be reacted with monomers containing a reactive functional group such as (meth)acrylamides or (meth)acrylates containing hydroxyl, carboxyl, amine or succinimide groups.

Suitable thereto-sensitive polymers are described in U.S. Pat. No. 7,425,581 and in EP-A-1 776 400. Further, in WO 2010/033022 and WO2013/002636.

WO2012/039602 drug-polymer matrix particles are described using such polymers. Moreover, in WO 2012/039602 biodegradable linker molecules are described that may be used in these known polymer matrix particles.

Typically, nanoparticles based on thermosensitive block-copolymers as outlined hereinabove can be linked to the compounds of the invention using azide-alkyne copper-free coupling. Examples thereof are described in WO2017086794

Thus, in certain embodiments of the invention, a nanoparticle is prepared wherein a thiocycloheptyne derivative of the current invention is coupled to an azide-containing nanoparticle. In certain embodiments, the nanoparticle is a self-assembling polymeric micelle, preferably from thermosensitive block copolymers.

The invention also pertains to the use of a thiocycloheptyne derivative of the current invention, in a method for the coupling of for coupling two molecules of interest wherein optionally, the molecules are independently selected from amongst a drug, an antibody, a protein, a peptide, a ligand, a imaging label, a targeting ligand, a delivery agent, a nanoparticle, and a carrier. The invention further relates to the use of the thiocycloheptyne derivative of the current invention in a bioorthogonal, optional copper-free, click reaction and to the use in a method for the coupling of a nanoparticle using a copper free click reaction to one or more of a drug, an antibody, a protein, a peptide, a ligand, a imaging label, a targeting ligand, a delivery agent, a nanoparticle, and a carrier. In particular, the coupling of azide-containing thermosensitive polymers with the compounds of the invention is advantageously since the click chemistry between the alkyne-containing compounds of the invention and azides is faster compared to conventional alkynes used in click chemistry, especially in the preparation of biodegradable nanoparticles and conjugated/entrapped drugs.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

EXAMPLES

FIG. 54 provides an overview of generated 1-imino-3,3, 6,6-tetramethyl-4,5-didehydro-2,3,6,7-tetrahydro-1H-1λ6-thiepine 1-oxide (TMTHSI) derivatives according to the invention, the synthesis of which is described in the examples below.

The core structure of TMTHSI (Example 2) can be functionalised in various ways.

Example 2, X=O, Y=N, core TMTHSI structure, R1-R4=Methyl, R5-R8=Hydrogen

Example 3, X=O, Y=N, is Example 2, with L=succinic linker, Q=an activated NHS ester, R1-R4=Methyl, R5-R8=Hydrogen Example 5, is Example 3 where the NHS ester is displaced in a reaction with benzylamine, R1-R4=Methyl, R5-R8=Hydrogen Example 8, X=O, Y=N, is Example 3 where the NHS ester is displaced in a reaction with HER2 peptide, R1-R4=Methyl, R5-R8=Hydrogen Example 11, X=O, Y=N, is Example 3 where the NHS ester is displaced in a reaction with a di-amino-PEG spacer (=L), Q is amine, R1-R4=Methyl, R5-R8=Hydrogen Example 12, X=O, Y=N,

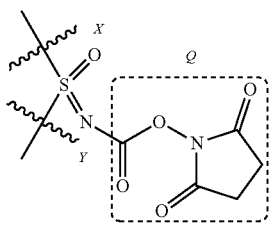

R1-R4=Methyl, R5-R8=Hydrogen

Example 13, X=O, Y=N-Trifluoroacetamide, L=no linker, Q=no functionality. R1-R4=Methyl, R5-R8=Hydrogen. This compound is intended for α-sulfur substitutions Example 14, X=O, Y=N, is Example 12 where the NHS ester is displaced in a reaction with an amino-PEG-hydroxyl spacer (=L), Q is hydroxyl, R1-R4=Methyl, R5-R8=Hydrogen Example 15, X=O, Y=N, is Example 2, with L=—S(O2) Phenyl-, Q=3-methoxycarbonyl, R1-R4=Methyl, R5-R8=Hydrogen Example 16, X=O, Y=N, is Example 2, with L=—S(O2) Phenyl, Q=3-hydroxycarbonyl, R1-R4=Methyl, R5-R8=Hydrogen Example 17 X=O, Y=N-Methyl, L=no linker, Q=no functionality. R1-R4=Methyl, R5-R8=Hydrogen. This compound is intended for α-sulfur substitutions Example 18 X=O, Y=N-Methyl, L=no linker, Q=no functionality. R1-R4=Methyl, R5-R8=One hydrogen has been displaced with L=-methylenephenyl-, Q=4-Methoxycarbonyl. This compound is an α-sulfur substituted variant of TMTHSI Example 19, X=O, Y=N, is Example 2, with L=-methylenephenyl-, Q=4-Methoxycarbonyl, R1-R4=Methyl, R5-R8=Hydrogen Example 23, X=O, Y=N, is Example 12 where the NHS moiety is replaced by a cystamine based amine linker, L=—C(O)NHC2H4SSC2H4NHC(O)C3H6-, Q=COOH,

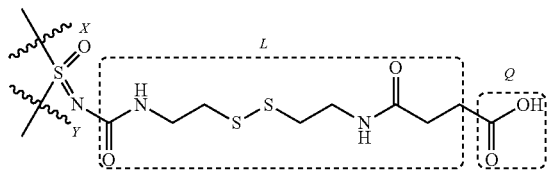

R1-R4=Methyl, R5-R8=Hydrogen

Example 24, X=O, Y=N, is Example 23 activated as NHS ester, L=—C(O)NHC2H4SSC2H4NHC(O)C3H6-, Q=((2,5-dioxopyrrolidin-1-yl)oxy)carbonyl, C(O)OSu.

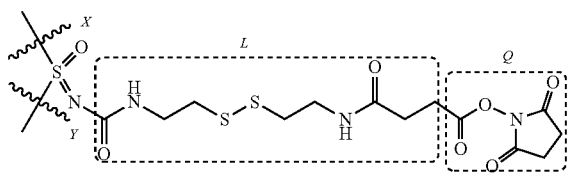

R1-R4=Methyl, R5-R8=Hydrogen

Example 25, X=O, Y=N, is Example 24 where the NHS ester is displaced in a reaction with Amino —C6 functionalised siRNA oligonucleotide, R1-R4=Methyl, R5-R8=Hydrogen Example 31, X=O, Y=N, is Example 12 where the NHS ester is displaced in a reaction with Amino PEG-functionalised Folic acid, R1-R4=Methyl, R5-R8=Hydrogen Example 33, X=O, Y=N, is Example 12 where the NHS ester is displaced in a reaction with a di-amino-PEG spacer (=L), Q is amine, R1-R4=Methyl, R5-R8=Hydrogen Example 34, X=O, Y=N, is Example 33 reacted with a Cy7 NHS label. L=di-amino-PEG spacer, R1-R4=Methyl, R5-R8=Hydrogen A person skilled in the art is well capable of providing further derivatives having further variables for R1-R8, L and/or Q and coupling to further molecules of interest, such as a drug, antibody, protein, peptides, ligand, imaging label, targeting ligand, delivery agent, nanoparticle or carrier using reactions known in the art, in addition to the structures prepared in the examples below and/or shown in FIG. 54.

Example 1: Synthesis of (3,3,6,6-Tetramethylthiepane-4,5-diylidene)bis(hydrazine)

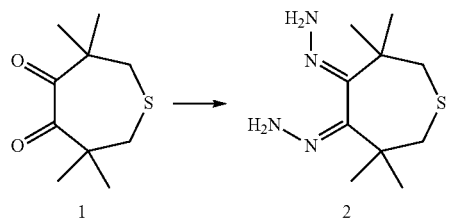

A glass autoclave (300 ml) was charged with 3,3,6,6-tetramethylthiepane-4,5-dione (6.17 g, 30.8 mmol), ethanol (2.4 ml) and ethyleneglycol (60 ml). To the stirred mixture was added hydrazine sulfate (16.03 g, 123 mmol, 4 eq.) and hydrazine monohydrate (3 ml, 61.6 mmol, 2 eq.). The autoclave was closed and heated in an oil bath at 140° C., for 20 hours.

After cooling to room temperature, the mixture was partitioned between water (500 ml) and diethyl ether (200 ml) and transferred to a separatory funnel while filtered over a piece of cotton to remove some white solid residue (likely hydrazine sulfate, as it slowly dissolves in water). The layers were separated and the aqueous layer was extracted with diethyl ether (2×100 ml). The combined ethereous layers were washed with water (2×75 ml) and brine (100 ml), dried over $Na_2SO_4$, and concentrated under reduced pressure to afford 5.75 g of the crude product as a thick yellow oil.

The residue was purified by flash column chromatography (silica 40 g; 30% EtOAc in heptane); the product fractions were combined and concentrated under reduced pressure. The residue was co-evaporated with diethyl ether to afford 0.9 g (12%) of the product as an off-white solid.

GC/MS (Method_A) $t_R$ 4.47 min, $M^+$=228.

*$^1$H NMR (400 MHz, Chloroform-d) δ 5.24 (s, 4H), 2.54 (d, J=14.4 Hz, 2H), 2.48 (d, J=14.4 Hz, 2H), 1.34 (s, 6H), 1.21 (s, 6H).

Example 2: Synthesis of 1-imino-3,3,6,6-tetramethyl-4,5-didehydro-2,3,6,7-tetrahydro-1H-1λ⁶-thiepine 1-oxide (TMTHSI)

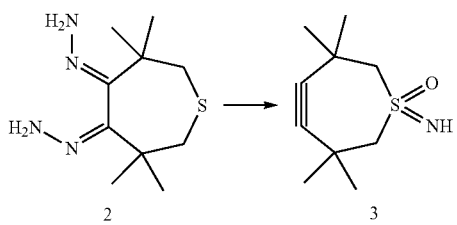

An 8 ml screwcap vial was charged with (3,3,6,6-tetramethylthiepane-4,5-diylidene)bis(hydrazine) (100 mg, 0.44 mmol) and ammonium acetate (270 mg, 3.5 mmol, 8 eq.) and suspended in methanol (0.4 ml). The mixture was cooled in ice/water. A solution of iodobenzene diacetate (494 mg, 1.53 mmol, 3.5 eq.) in a mixture of MeOH (0.4 ml) and dichloromethane (0.6 ml) was added dropwise to control the exotherm and the gas formation (the reaction showed gas evolution upon each drop added). After the addition was complete, the mixture was stirred at room temperature for 1 hour.

The mixture was diluted with dichloromethane (2 ml) and quenched with brine (1 ml). The organic layer was removed by pipette and passed over a phase separator. The aqueous residue was extracted with dichloromethane (2×), each time the organic phase was passed over a phase separator and combined with the previous extract(s). The organic extracts were concentrated under reduced pressure, carefully monitoring the evaporation as the product might be volatile, to afford 427 mg of the crude product as a yellow oil. The residue was purified by preparative RP-MPLC (Reveleris, XSelect; 10-50% MeCN in water, 10 mM NH₄HCO₃, pH=9.5). The product fractions were combined and extracted with dichloromethane (3×), each organic extract passed over a phase separator and concentrated under reduced pressure. The residue was coevaporated with heptane and diethyl ether to afford 33 mg (37%) of a crystalline residue.

LC/MS (SC_BASE) $t_R$ 1.628 min, purity 98.1%, mass found [M+H]⁺ 200.

¹H NMR (400 MHz, Chloroform-d) δ 3.26 (d, J=14.1 Hz, 2H), 3.18 (d, J=14.1 Hz, 2H), 2.76 (s, 1H), 1.46 (s, 6H), 1.30 (s, 6H).

TMTHSI was proven to be stable during storage. Compound 3 was stored as a powder at both light and dark locations under atmospheric pressure. ¹H-NMR en LC/MS (SC_BASE) proved the compound was still in tact after 10 months of storage.

Example 3: Coupling to a Linker. Synthesis of 2,5-dioxopyrrolidin-1-yl 4-oxo-4-((3,3,6,6-tetramethyl-1-oxido-4,5-didehydro-2,3,6,7-tetrahydro-1λ⁶-thiepin-1-ylidene)amino)butanoate

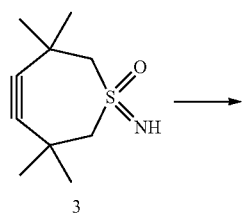

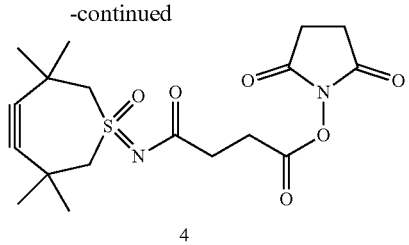

Diisopropylethylamine (266 μl, 1.52 mmol, 2 eq.) was added to a mixture of 1-imino-3,3,6,6-tetramethyl-4,5-didehydro-2,3,6,7-tetrahydro-1H-1λ⁶-thiepine 1-oxide (152 mg, 0.76 mmol) and succinic anhydride (114 mg, 1.14 mmol, 1.5 eq.) in dichloromethane (5 ml) and the resulting mixture was stirred at room temperature for 20 hours.

The reaction mixture was concentrated under reduced pressure and redissolved in dichloromethane and concentrated again under reduced pressure. The residue was redissolved in dichloromethane (5 ml) and N-hydroxysuccinimide (220 mg, 1.91 mmol, 2.5 eq.) was added. The mixture was stirred for 5 minutes, then a suspension of N-(3-dimethylaminopropyl)-N'-ethylcarbodiimide hydrochloride (366 mg, 1.91 mmol, 2.5 eq.) in dichloromethane (0.5 ml) was added via pipette. The resulting solution was stirred at room temperature for 4 hours.

The mixture was quenched with aqueous 2M KHSO₄ soln. and the organic phase was passed through a phase separator. The filtrate was concentrated under reduced pressure to afford 420 mg of the crude mixture as a foam.

The residue was purified by flash column chromatography (silica 12 g, 50-75% EtOAc in heptane), the product fractions were pooled and concentrated under reduced pressure to afford 141 mg (46%) of the product as a white solid.

LC/MS (SC_ACID) $t_R$ 1.84 min, purity 85%, mass found [M+H]⁺ 397.

¹H NMR (400 MHz, Chloroform-d) δ 3.79 (d, J=14.1 Hz, 2H), 3.63 (d, J=14.2 Hz, 2H), 2.97-2.90 (m, 2H), 2.88-2.81 (m, 4H), 2.79-2.71 (m, 2H), 1.55 (s, 6H), 1.28 (s, 6H).

Example 4: Coupling to a Linker. Synthesis of N¹-benzyl-N⁴-(3,3,6,6-tetramethyl-1-oxido-4,5-didehydro-2,3,6,7-tetrahydro-1λ⁶-thiepin-1-ylidene)succinamide

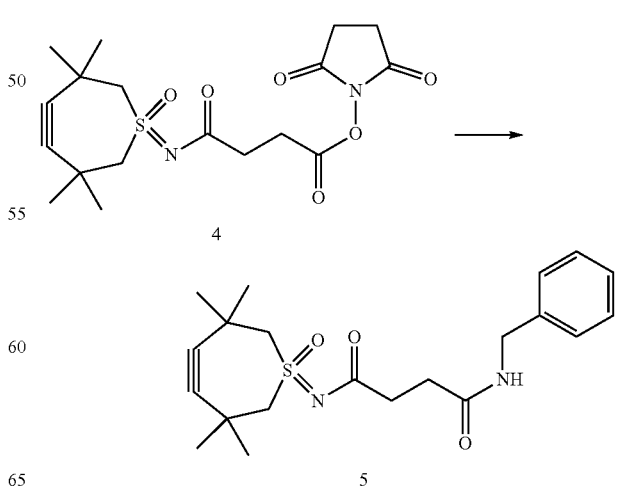

To a solution of 2,5-dioxopyrrolidin-1-yl 4-oxo-4-((3,3,6,6-tetramethyl-1-oxido-4,5-didehydro-2,3,6,7-tetrahydro-1λ⁶-thiepin-1-ylidene)amino)butanoate (15.8 mg, 0.040 mmol) in dichloromethane (1 ml) was added benzylamine (8.71 μl, 0.080 mmol, 2 eq.). The reaction mixture was stirred at room temperature for 4 hours. Then, the reaction mixture was purified by flash column chromatography (silica, 12 g; 70-100% EtOAc in heptane) the product fractions were combined and concentrated under reduced pressure to afford 13.1 mg of product with a purity of ~83% by LC/MS.

The material was purified by preparative RP-MPLC (Reveleris, XSelect; 20-60% MeCN in water, 10 mM $NH_4HCO_3$, pH=9.5) the product fractions were pooled and concentrated under reduced pressure to afford 6.2 mg (40%) of the title compound as a white solid.

LC/MS (SC_BASE) $t_R$ 2.01 min, purity 96.8%, mass found $[M+H]^+$ 389.

¹H NMR (400 MHz, Chloroform-d) δ 7.36-7.22 (m, 5H), 6.25 (s, 1H), 4.44 (d, J=5.7 Hz, 2H), 3.60 (d, J=14.1 Hz, 2H), 3.53 (d, J=14.1 Hz, 2H), 2.73 (dd, J=6.8, 6.2 Hz, 2H), 2.52 (dd, J=6.6, 6.4 Hz, 2H), 1.49 (s, 6H), 1.24 (s, 6H).

Example 5: Click Reaction. Synthesis of 1-benzyl-6-imino-4,4,8,8-tetramethyl-1,4,5,6,7,8-hexahydro-6λ⁴-thiepino[4,5-d][1,2,3]triazole 6-oxide

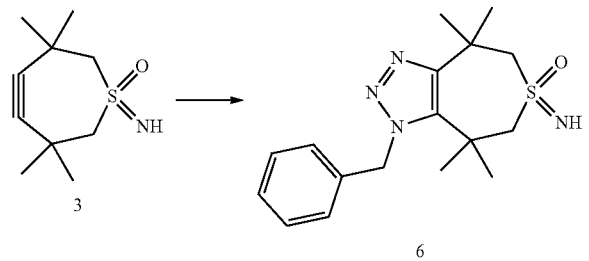 [SMILES: CC1(C)C#CC(C)(C)CS(=N)(=O)C1 ; CC1(C)CS(=N)(=O)CC(C)(C)c2c1nnn2Cc1ccccc1]

LC/MS:

An LC/MS vial was charged with 1-imino-3,3,6,6-tetramethyl-4,5-didehydro-2,3,6,7-tetrahydro-1H-1λ⁶-thiepine 1-oxide (5 mg, 0.025 mmol) and dissolved in MeCN (1 ml), benzylazide was added and the reaction mixture was analysed by LC/MS. LC/MS analysis showed full consumption of starting material and formation of product as a mixture with unreacted benzylazide.

LC/MS (SC_BASE) $t_R$ 1.728 min, purity 64%, mass found $[M+H]^+$ 333.

¹H-NMR:

1-Imino-3,3,6,6-tetramethyl-4,5-didehydro-2,3,6,7-tetrahydro-1H-1λ⁶-thiepine 1-oxide (5 mg, 0.025 mmol) was dissolved in $CDCl_3$ (0.6 ml) and benzylazide was added. ¹H-NMR was recorded after approximately 15 minutes reaction time:

¹H NMR (400 MHz, Chloroform-d) δ 7.40-7.29 (m, 3H), 7.06-7.01 (m, 2H), 5.73 (s, 2H), 3.45 (d, J=8.9 Hz, 4H), 2.69 (s, 1H), 1.70 (d, J=2.1 Hz, 6H), 1.44 (d, J=2.7 Hz, 6H).

Full consumption of starting material, ~35 mol % excess of benzylazide present.

Example 6: Click Reaction. Synthesis of N¹-benzyl-N⁴-(1-benzyl-4,4,8,8-tetramethyl-6-oxido-4,5,7,8-tetrahydro-1H-6λ⁴-thiepino[4,5-d][1,2,3]triazol-6-ylidene)succinamide

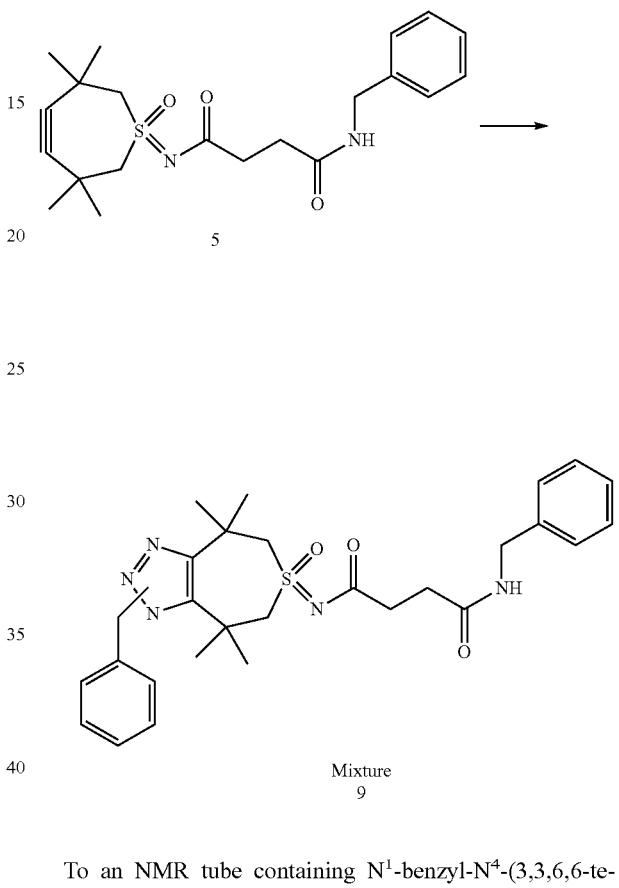

To an NMR tube containing N¹-benzyl-N⁴-(3,3,6,6-tetramethyl-1-oxido-4,5-didehydro-2,3,6,7-tetrahydro-1λ⁶-thiepin-1-ylidene)succinamide (4.6 mg, 12 μmol) dissolved in $CDCl_3$, was added a solution of benzylazide in $CDCl_3$ (10 vol %, 15.5 μl, 1.05 eq.). The mixture was shaken and ¹H-NMR-analysis was performed after approximately 5 minutes reaction time.

¹H NMR (400 MHz, Chloroform-d) δ 7.43-7.27 (m, 8H), 7.06-7.00 (m, 2H), 6.18 (s, 1H), 5.72 (s, 2H), 4.42 (d, J=5.8 Hz, 2H), 3.96 (d, J=15.5 Hz, 1H), 3.82 (d, J=15.0 Hz, 1H), 3.70 (d, J=15.3 Hz, 1H), 3.57 (d, J=15.1 Hz, 1H), 2.74-2.67 (m, 2H), 2.49 (t, J=6.7 Hz, 2H), 1.70 (s, 3H), 1.67 (s, 3H), 1.44 (s, 3H), 1.36 (s, 3H).

The mixture was concentrated to dryness and the residue was analysed by LC/MS:

LC/MS (SC_BASE) showed product peak with target mass ($t_R$ 1.947 min, purity 75%, $[M+H]^+$ 522).

LC/MS (SC_ACID) showed two product peaks [resp. $t_R$ 1.90 (57%) and 1.94 min (23%)] with target mass ($[M+H]^+$ 522).

Example 7: Coupling of TMTHSI-Containing Linker to HER2-Peptide

Preparation of
TMTHSI-Succinyl-Fcycl[CGDGFYAC]YMDV

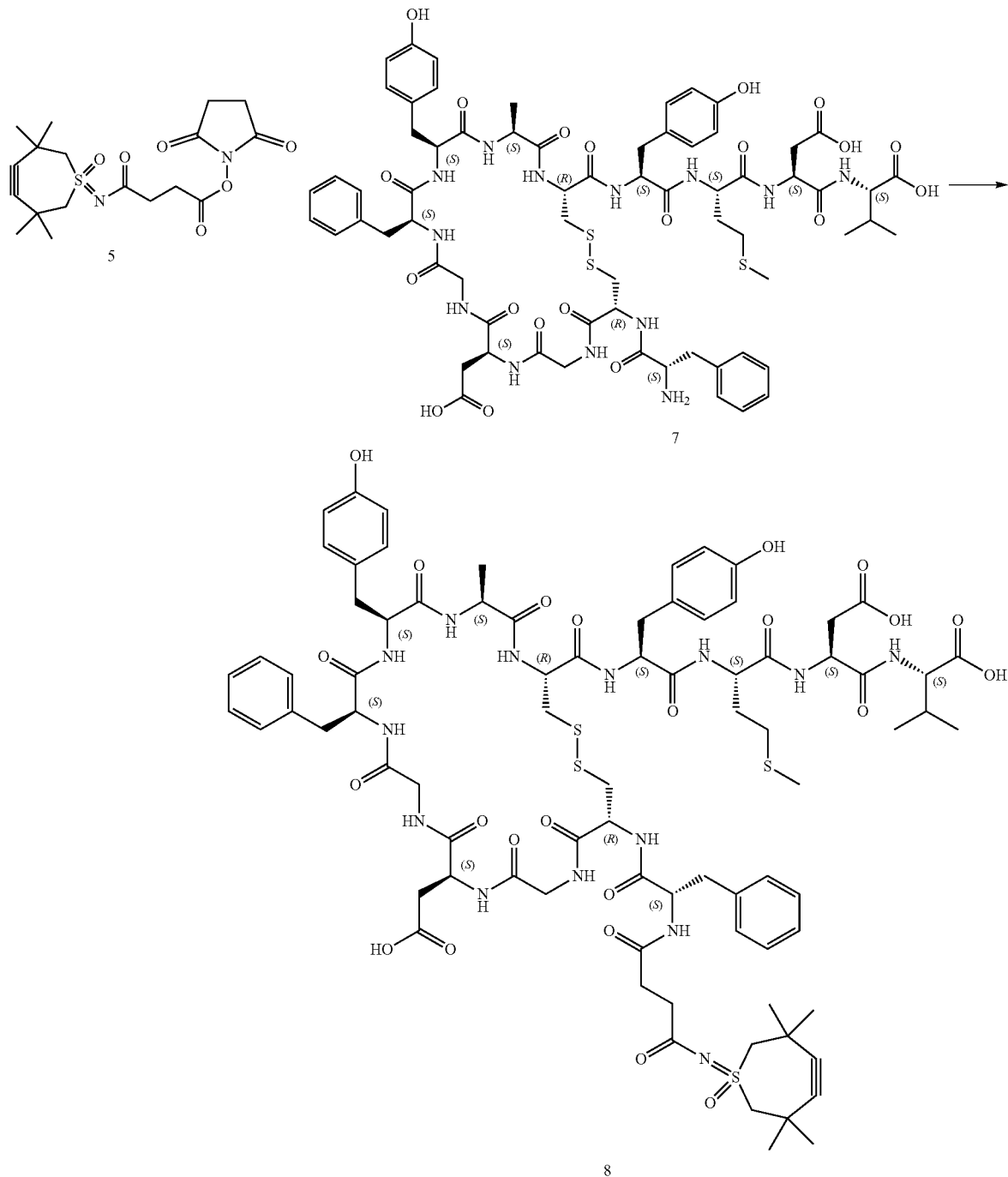

An 8 ml screwcap vial was charged with Fcycl [CGDGFYAC]YMDV (20 mg, 13 μmol) and dissolved in DMSO (1 ml). 2,5-Dioxopyrrolidin-1-yl 4-oxo-4-((3,3,6,6-tetramethyl-1-oxido-4,5-didehydro-2,3,6,7-tetrahydro-1λ⁶-thiepin-1-ylidene)amino)butanoate (6.5 mg, 14 μmol, 1.04 eq.) was added followed by diisopropylethylamine (13 μl, 75 μmol, 5.6 eq.). The mixture was stirred at room temperature for 16 hours. The reaction mixture was purified directly by preparative RP-MPLC (Reveleris, LUNA-C18, 20-60% MeCN in water, 0.1% Formic acid), the product fractions were pooled and lyophilised to afford 16.6 mg (69%) of the product.

LC/MS (AN_BASE_M1800) $t_R$ 2.57 min, purity 96%, mass found [M−H]⁻ 1768, [M−2H]²⁻ 883

Analysis Methods

GC/MS Methods:

Method A, Instrument: GC: Agilent 6890N, FID: Det. temp: 300° C. and MS: 5973 MSD, EI-positive, Det. temp.: 280° C. Mass range: 50-550; Column: RXi-5 MS 20 m, ID 180 μm, df 0.18 μm; Average velocity: 50 cm/s; Injection vol: 1 μl; Injector temp: 250° C.; Split ratio: 20/1; Carrier gas: He; Initial temp: 100° C.; Initial time: 1.5 min; Solvent delay: 1.3 min; Rate 75° C./min; Final temp 250° C.; Final time 2.5 min.

LC/MS Methods:

SC_ACID, Apparatus: Agilent 1260 Bin. Pump: G1312B, degasser; autosampler, ColCom, DAD: Agilent G1315D, 220-320 nm, MSD: Agilent LC/MSD G6130B ESI, pos/neg 100-1000, ELSD Alltech 3300 gas flow 1.5 ml/min, gas temp: 40° C.; column: Waters XSelect™ C18, 30×2.1 mm, 3.5μ, Temp: 35° C., Flow: 1 mL/min, Gradient: $t_0$=5% A, $t_{1.6\ min}$=98% A, $t_{3\ min}$=98% A, Post time: 1.3 min, Eluent A: 0.1% formic acid in acetonitrile, Eluent B: 0.1% formic acid in water).

SC_BASE, Apparatus: Agilent 1260 Bin. Pump: G1312B, degasser; autosampler, ColCom, DAD: Agilent G1315C, 220-320 nm, MSD: Agilent LC/MSD G6130B ESI, pos/neg 100-1000; column: Waters XSelect™ CSH C18, 30×2.1 mm, 3.5μ, Temp: 25° C., Flow: 1 mL/min, Gradient: $t_0$=5% A, $t_{1.6\ min}$=98% A, $t_{3\ min}$=98% A, Post time: 1.3 min, Eluent A: acetonitrile, Eluent B: 10 mM ammonium bicarbonate in water (pH=9.5).

AN_BASE_M1800, Apparatus: Agilent 1260 Bin. Pump: G1312B, degasser; autosampler, ColCom, DAD: Agilent G1315C, 220-320 nm, MSD: Agilent LC/MSD G6130B ESI, pos/neg 800-1800; column: Waters XSelect™ CSH C18, 50×2.1 mm, 3.5μ, Temp: 25° C., Flow: 0.8 mL/min, Gradient: $t_0$=5% A, $t_{3.5\ min}$=98% A, $t_{6\ min}$=98% A, Post time: 2 min, Eluent A: acetonitrile, Eluent B: 10 mM ammonium bicarbonate in water (pH=9.5).

¹H-NMR:

All ¹H-NMR spectra were recorded on a Bruker Avance-400 ultrashield NMR spectrometer, using CDCl₃ or DMSO-d6 as solvent and are reported in ppm using TMS (0.00 ppm) as an internal standard.

Example 8: Coupling of TMTHSI-Containing Linker HER2-Peptide to an Azide Containing Nanoparticle (CriPec)

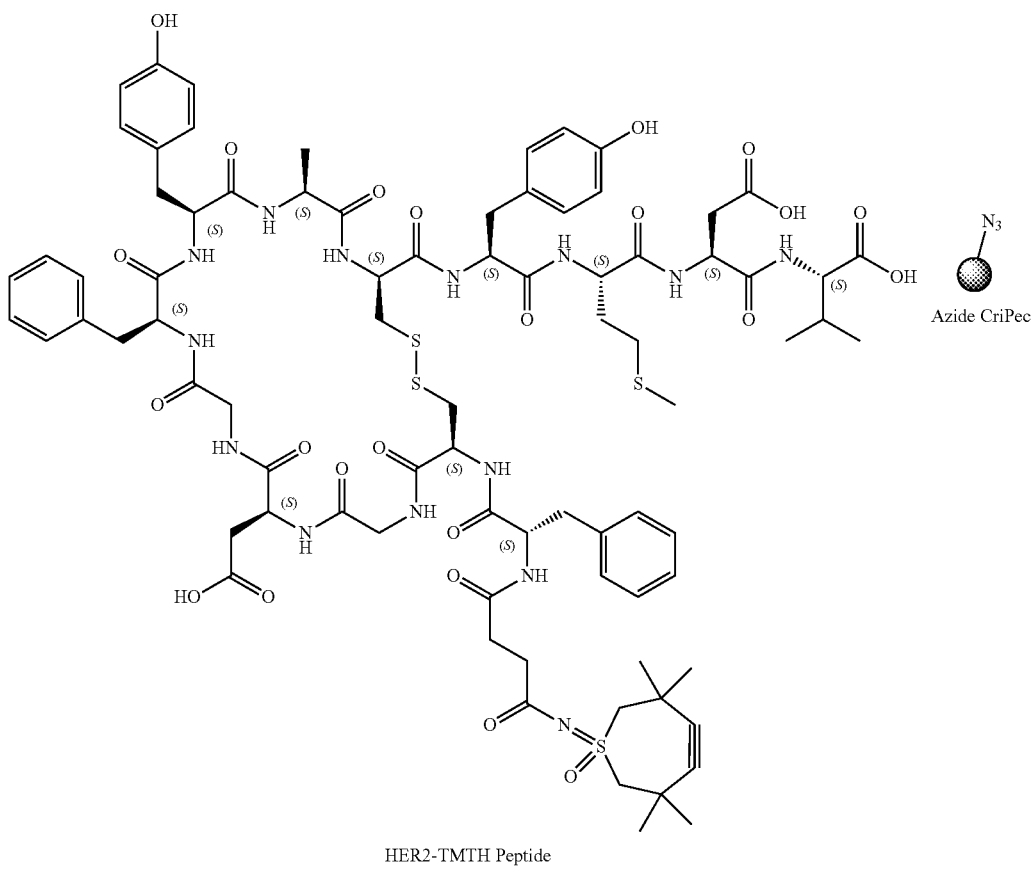

HER2-TMTH Peptide
8

-continued

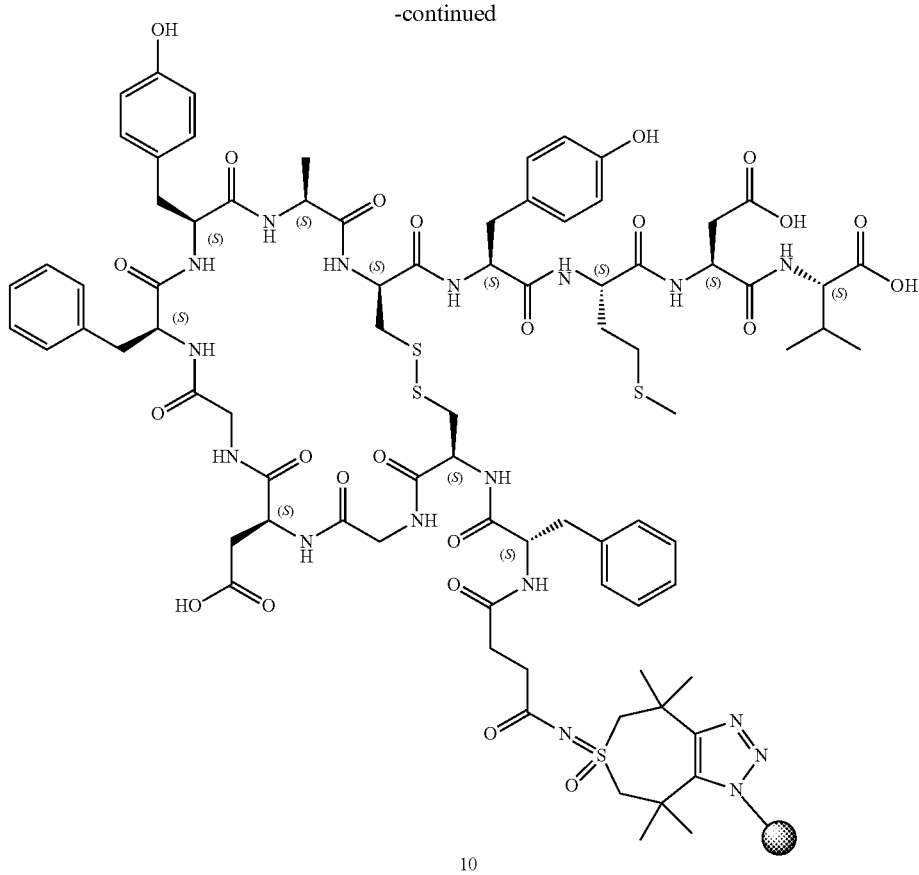

10

HER2 peptide-labelled core-crosslinked polymeric micelles were generated by conjugating HER2 peptide to the surface of the polymeric micelles shell and used for targeting studies. To allow for HER2 peptide conjugation via click chemistry, azide-functionalized polymeric micelles were manufactured essentially following the reported protocol [Hu et al. Biomaterials. 2015; 53:370-8], except that a fraction of azide-functionalized block copolymer (7.5 kDa, derivatized with 10 mol % crosslinker L2 [1], 5 w % of total block copolymer) was added next to the (95 w %) non-functionalized block copolymer (7.5 kDa, derivatized with 10 mol % crosslinker L2 [Biomaterials. 2015; 53:370-8],], 95 w % of total block copolymer). These two block copolymers were synthesized following the same procedures, except that for the former (azide-PEG$_{5000}$)$_2$-ABCPA initiator synthesized from azide-PEG$_{5000}$-OH was used instead. The obtained azide-functionalized polymeric micelles were then purified in 20 mM ammonium acetate pH 5 buffer containing 130 mM NaCl, buffer swapped to 20 mM sodium phosphate pH 7.4 buffer containing 130 mM NaCl and concentrated to approx. 30 mg/mL polymer equiv. using Tangential Flow Filtration (TFF) equipped with a modified Polyethersulfone (mPES) 100 kDa module (Spectrumlabs). Next, HER2 peptide was conjugated to the concentrated azide-functionalized core-crosslinked polymeric micelles via copper-free click chemistry using the following approach:

At RT, ACN (86 µL) was added to 200 µL of azide-functionalized modified core-crosslinked polymeric micelles (0.4 µmol azide equiv.) while stirring (300 rpm) in an amber UPLC vial. Upon dissipation of heat, HER2 peptide (1.0 eq., 0.4 µmol, 86 µL, Mercachem) was added dropwise to the reaction mixture. The progress of the conjugation reaction was monitored by UPLC-UV for 24 hours after which the reaction was stopped. Based on UPLC, conversion of HER2 peptide was determined to be 43%, which translates to 2.2% HER2 peptide labelled core-crosslinked polymeric micelles. After conjugation reaction, HER2 peptide-labelled polymeric micelles were purified by TFF against 10 v % ethanol to remove unreacted HER2 peptide.

Example 9: Coupling of TMTHSI-Containing Linker HER2-Peptide to an Azide Containing Nanoparticle (CriPec) Under Acidic pH To allow for HER2 peptide conjugation via click chemistry, azide-functionalized polymeric micelles were manufactured essentially following the reported protocol [Hu et al. Biomaterials. 2015; 53:370-8], except that a fraction of azide-functionalized block copolymer (7.5 kDa, derivatized with 10 mol % crosslinker L2 [1], 5 w % of total block copolymer) was added next to the (95 w %) non-functionalized block copolymer (7.5 kDa, derivatized with 10 mol % crosslinker L2 [Biomaterials. 2015; 53:370-8],], 95 w % of total block copolymer). These two block copolymers were synthesized following the same procedures, except that for the former (azide-PEG$_{5000}$)$_2$-ABCPA initiator synthesized from azide-PEG$_{5000}$-OH was used instead. The obtained azide-functionalized polymeric micelles were then purified in 20 mM ammonium acetate pH 5 buffer containing 130 mM NaCl and concentrated to approx. 60 mg/mL polymer equiv. using Tangential Flow Filtration (TFF) equipped with a modified Polyethersulfone (mPES) 100 kDa module (Spectrumlabs). Next, HER2 peptide was conjugated to the concentrated azide-functionalized core-crosslinked polymeric micelles via copper-free click chemistry using the following approach:

At RT, 150 mM Ammonium Acetate pH 5 (130 µL) was added to 1500 µL of azide-functionalized modified core-crosslinked polymeric micelles (0.57 µmol azide equiv.) while stirring (300 rpm) in an amber UPLC vial. Upon dissipation of heat, HER2 peptide (5.0 eq., 2.85 µmot 842 µL 2 mg/ml HER2-TMTH stock solution) was added dropwise to the reaction mixture. The progress of the conjugation reaction was monitored by UPLC-UV for 24 hours after which the reaction was stopped. Based on UPLC, conversion of HER2 peptide was determined to be 23%, which translates to 5% HER2 peptide labelled core-crosslinked polymeric micelles. After conjugation reaction, HER2 peptide-labelled polymeric micelles were purified by TFF against 10 v % ethanol to remove unreacted HER2 peptide.

Figure 1:
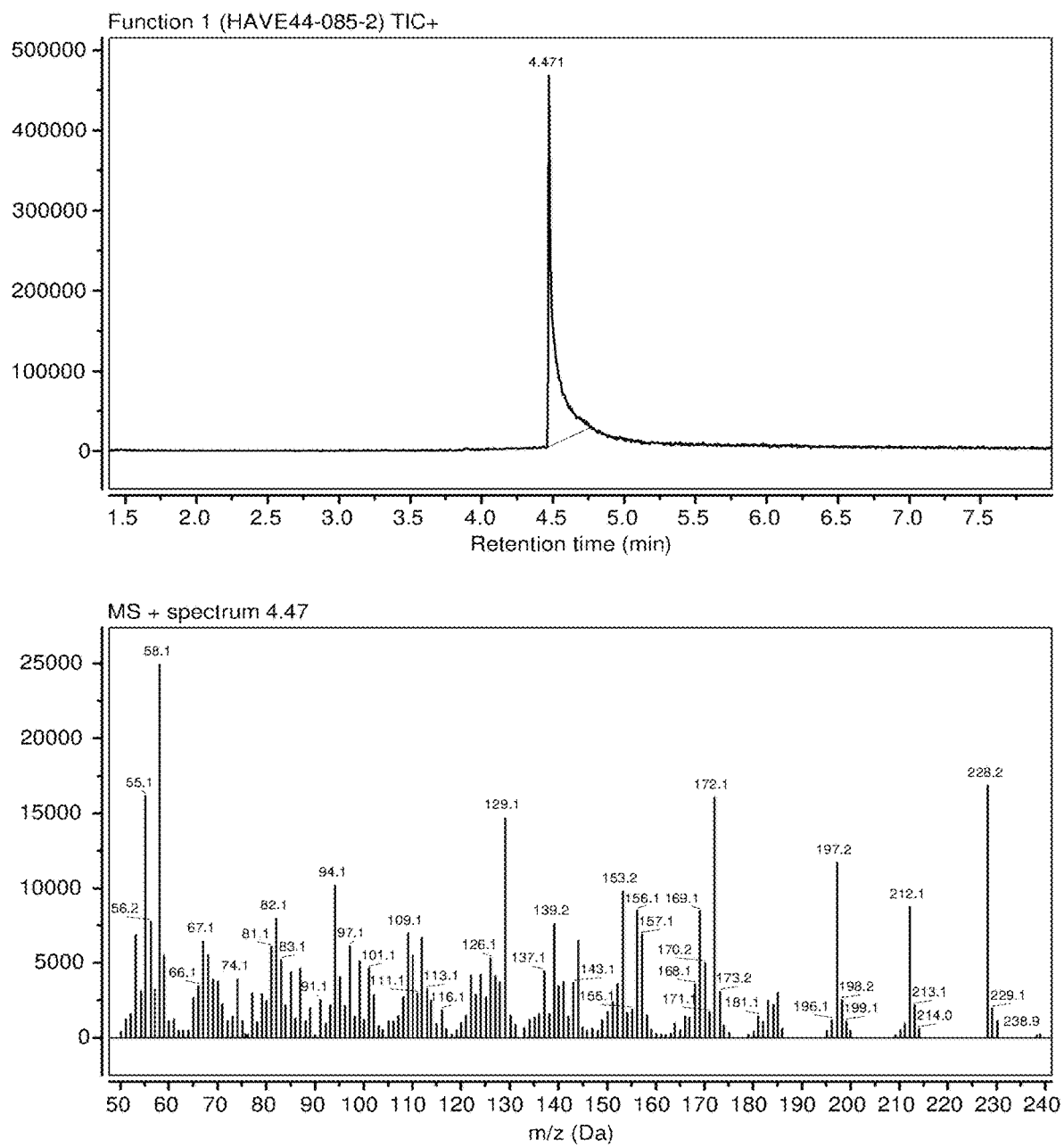
FIG. 1: Bishydrazone 2 analytical data
GCMS: Agilent 6890N/Column: RXi-5MS 20 m, ID 180 µm, df 0.18 µm. Average velocity 50 cm/s/Carrier gas: He. Initial temp 100° C./Initial time: 1.5 min/Solvent delay: 1.3 min. Rate 75° C./min, Final temp: 250° C., Final time: 4.5 min. Split ratio 20:1/Injector temp: 250° C., Injection volume: 1 µl. Detection: MSD (EI-positive)/Det. temp.: 280° C./Mass range: 50-550. Detection: FID/Detector temp: 300° C.
Figure 2:
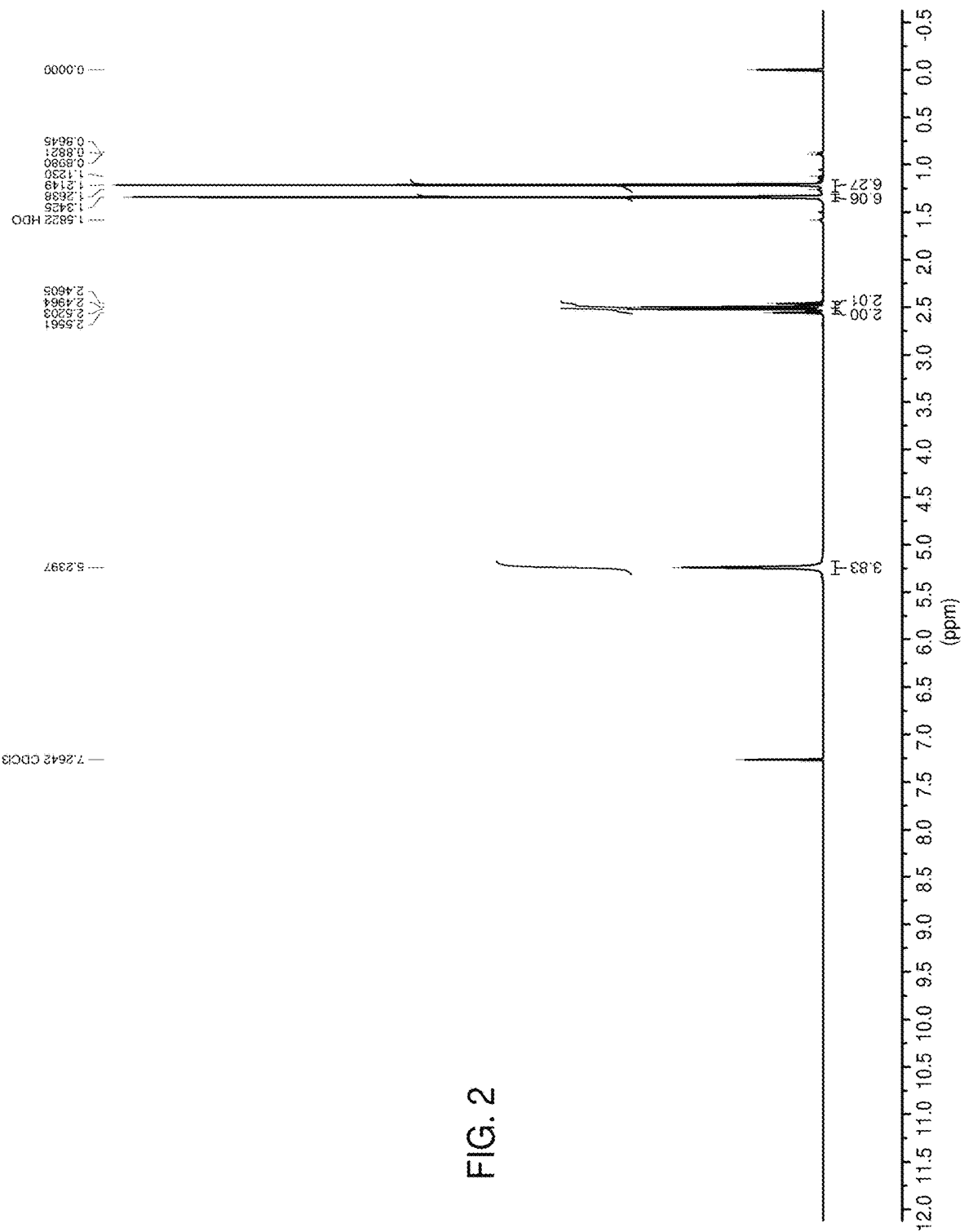
FIG. 2: Bishydrazone 2 analytical data
Bruker BioSpin GmbH; Method Pulse Sequence: zg30. Relaxation Delay: 1 s. Solvent: $CDCl_3$. Temperature: ~298.7411 K. Number of Scans: 16. Frequency: 400.132470966543 MHz. Nucleus: 1H.
Figure 3:
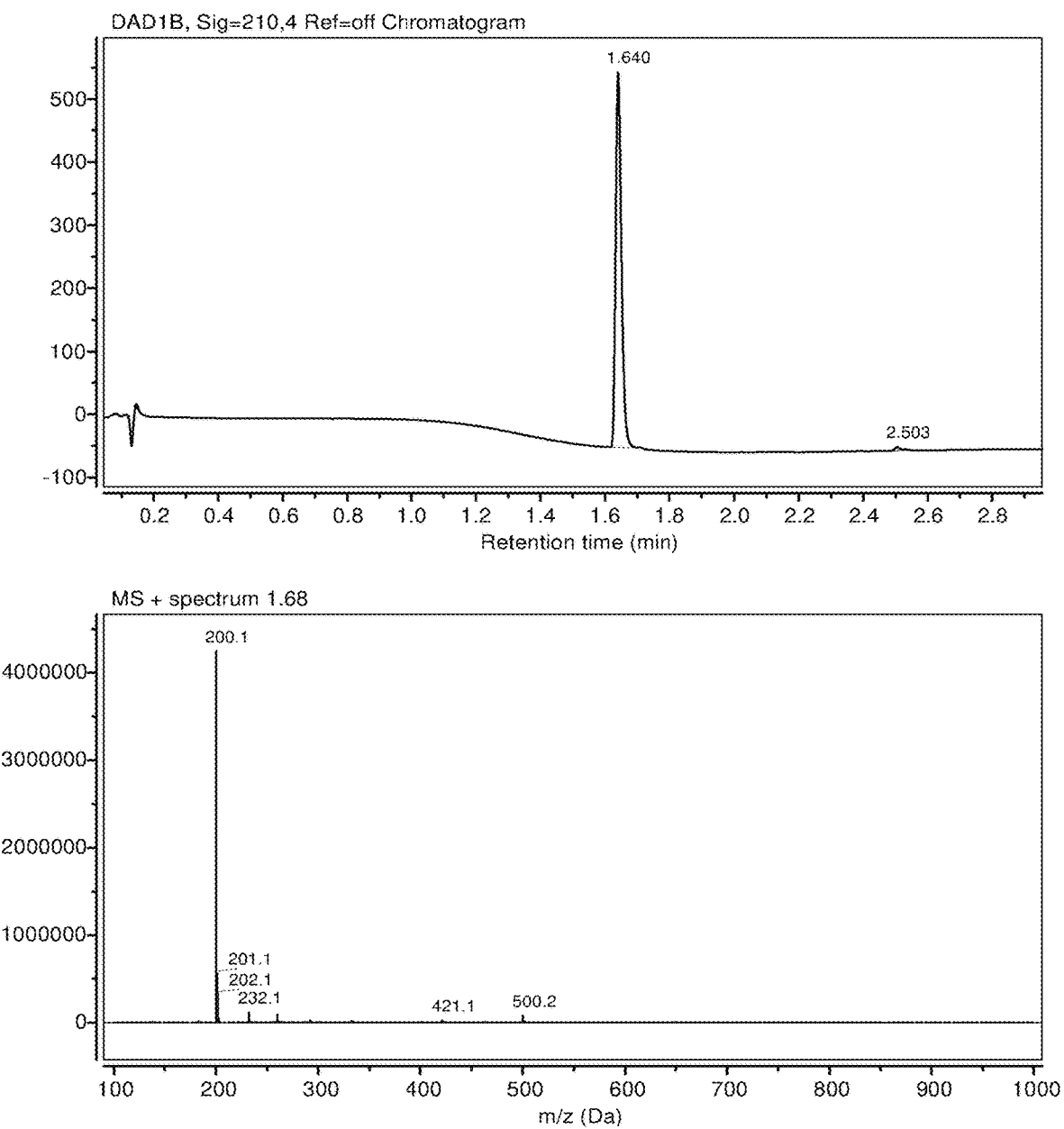
FIG. 3 [Example 2 Compound 3] TMTHSI analytical data
Column: Waters XSelect CSH C18 (30×2.1 mm 3.5µ). Flow: 1 ml/min; Column Temp: 25° C. Eluent A: 95% acetonitrile+5% 10 mM ammonium bicarbonate in water. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).
Figure 4:
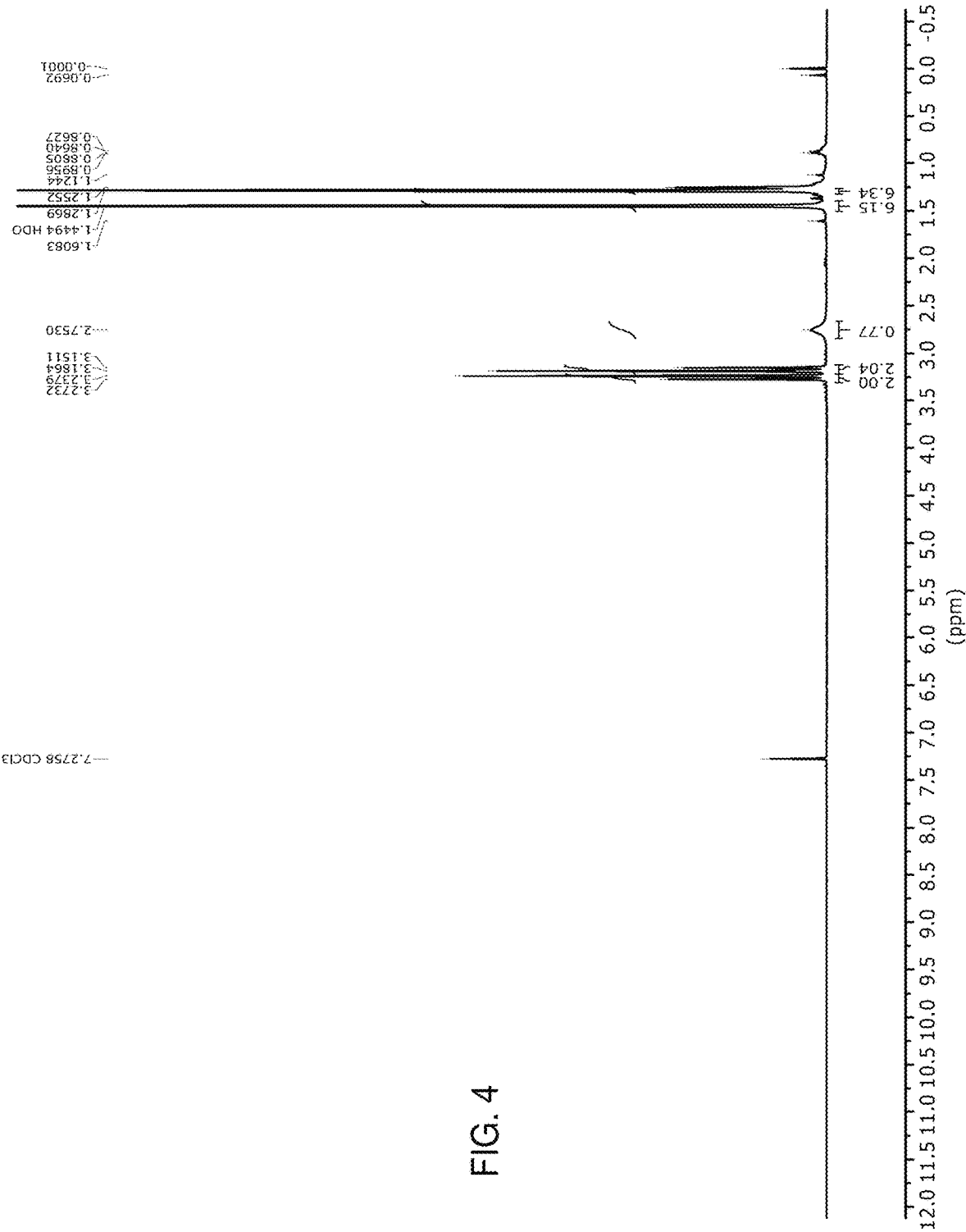
FIG. 4 [Example 2 Compound 3] TMTHSI analytical data
Bruker BioSpin GmbH; Method Pulse Sequence: zg30. Relaxation Delay: 1 s. Solvent: $CDCl_3$. Temperature: ~297.5603 K. Number of Scans: 16. Frequency: 400.132470966543 MHz. Nucleus: 1H.
Figure 5:
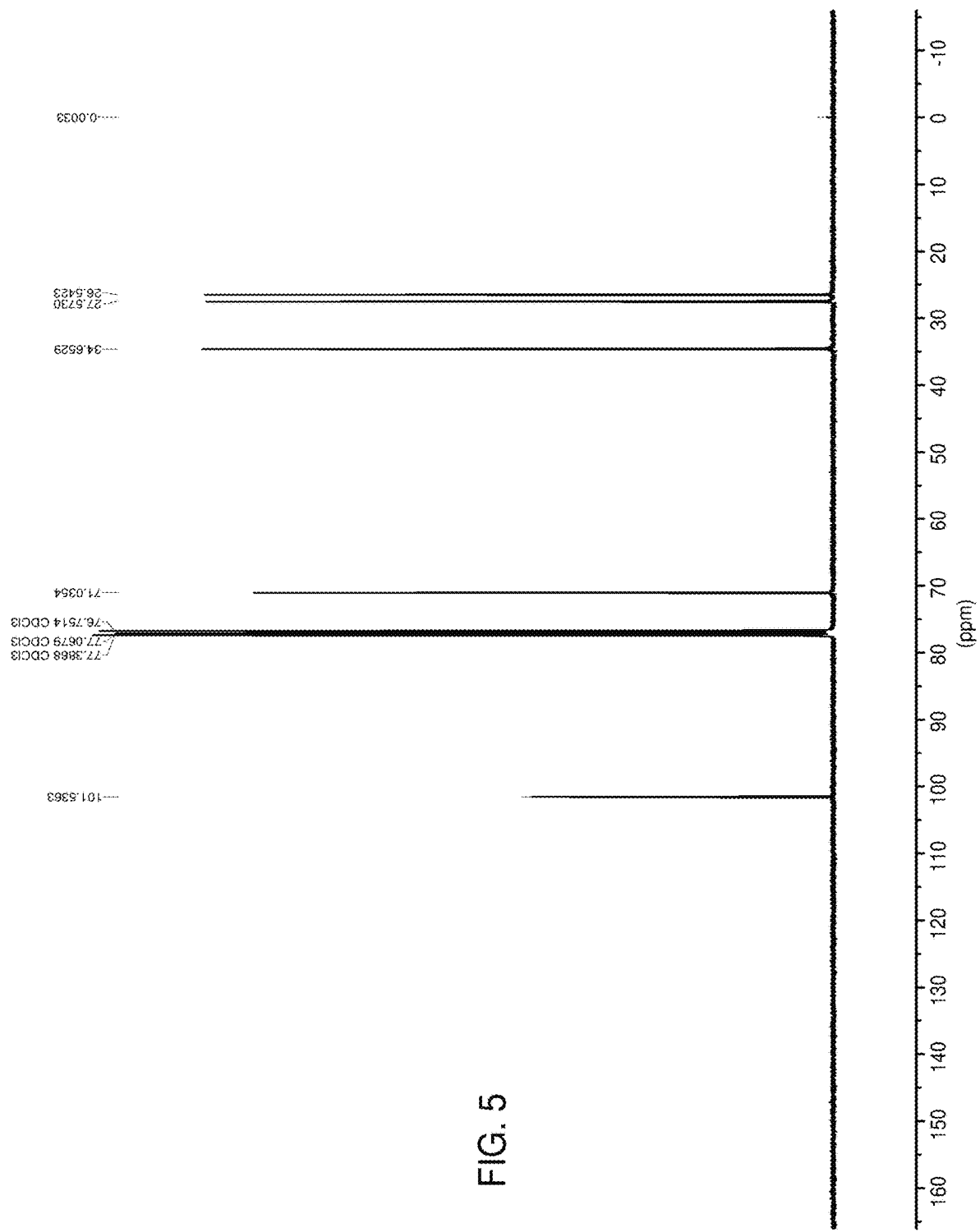
FIG. 5 [Example 2 Compound 3] TMTHSI analytical data
Bruker BioSpin GmbH; Method Pulse Sequence: zgpg30. Relaxation Delay: 8 s. Solvent: $CDCl_3$. Temperature ~300.5658 K. Number of Scans: 1024. Frequency: 100.622829328806 MHz. Nucleus: 13C.
Figure 6:
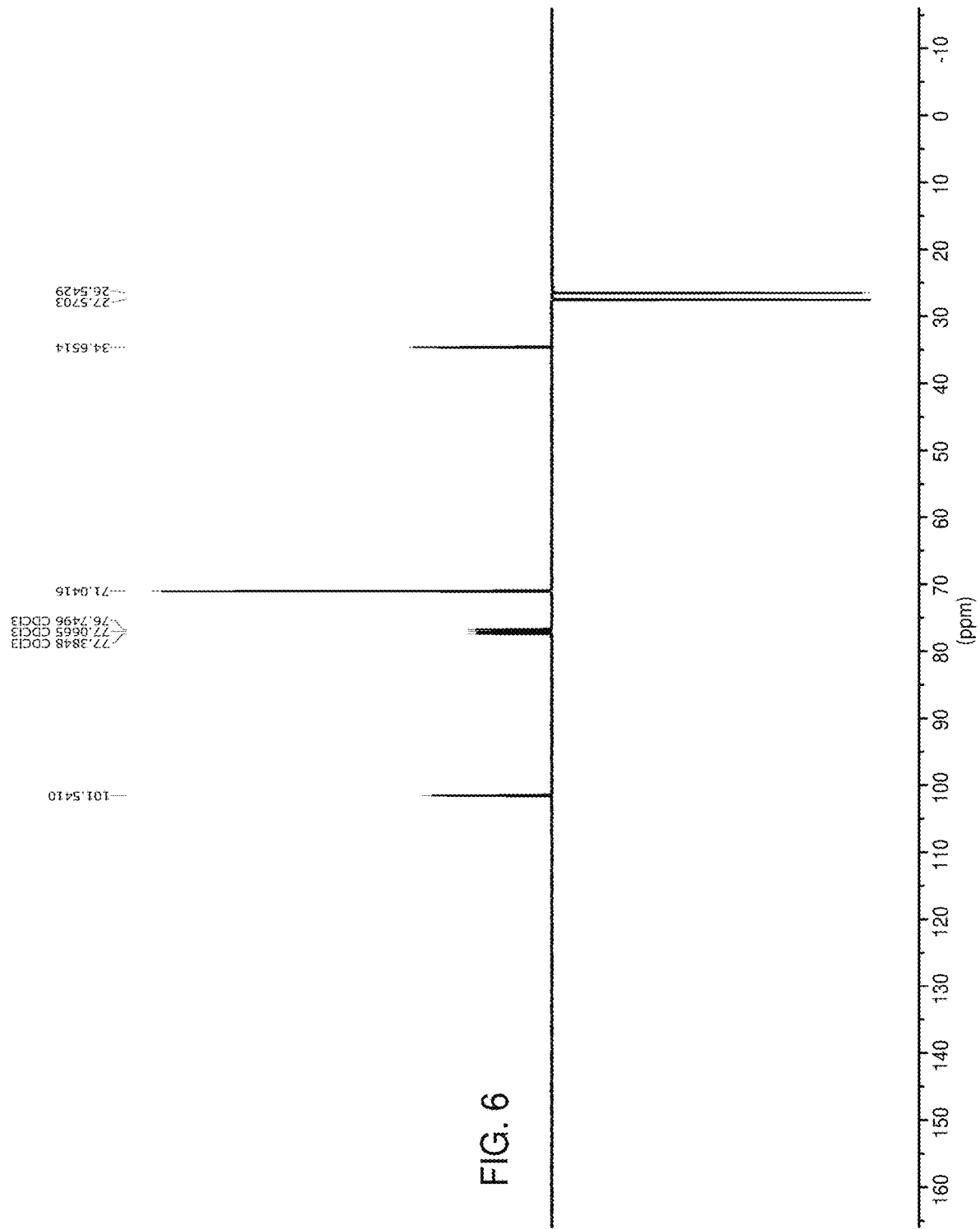
FIG. 6 [Example 2 Compound 3] TMTHSI analytical data
Bruker BioSpin GmbH; Method Pulse Sequence: jmod. Relaxation Delay: 8 s. Solvent: $CDCl_3$. Temperature: ~301.3172 K. Number of Scans: 1024. Frequency 100.622829802853 MHz. Nucleus: 13C.
Figure 7:
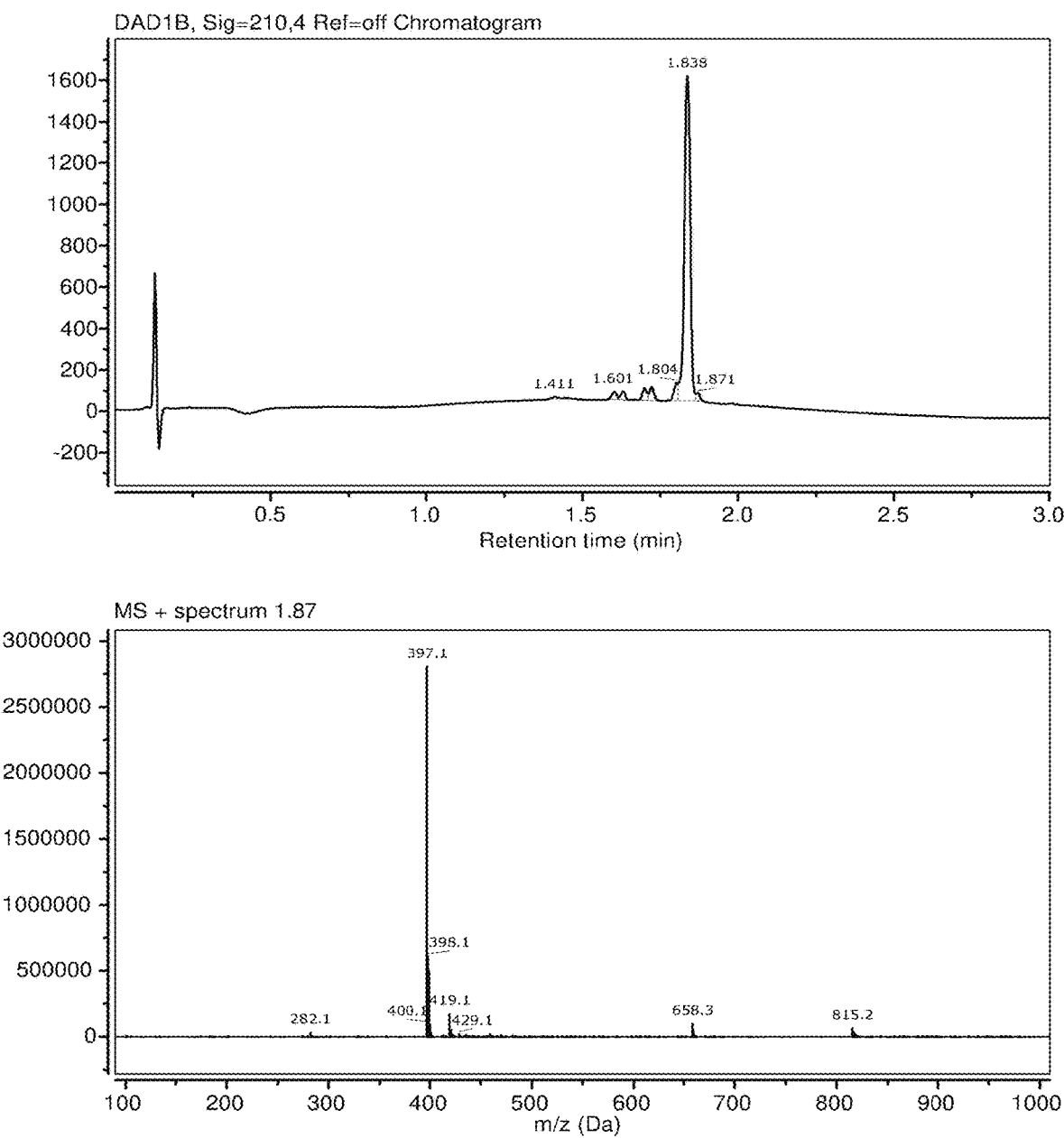
FIG. 7 [Example 3 Compound 4] TMTHSI-Suc-NHS analytical data
Column: Waters XSelect CSH C18 (30×2.1 mm, 3.5µ). Flow: 1 ml/min; Column temp: 35° C. Eluent A: 0.1% Formic acid in acetonitrile. Eluent B: 0.1% Formic acid in water. Lin. Gradient: t=0 min 5% A, t=1.6 min 98% A, t=3 min 98% A. Post time: 1.3 min. Detection: DAD (220-320 nm, 210 and 220 nm). Detection PDA (210-400 nm). Detection: MSD ESI pos/neg (mass range: 100-1000). Detection: ELSD (Alltech 3300): gas flow 1.5 ml/min, gas temp: 40° C.
Figure 8:
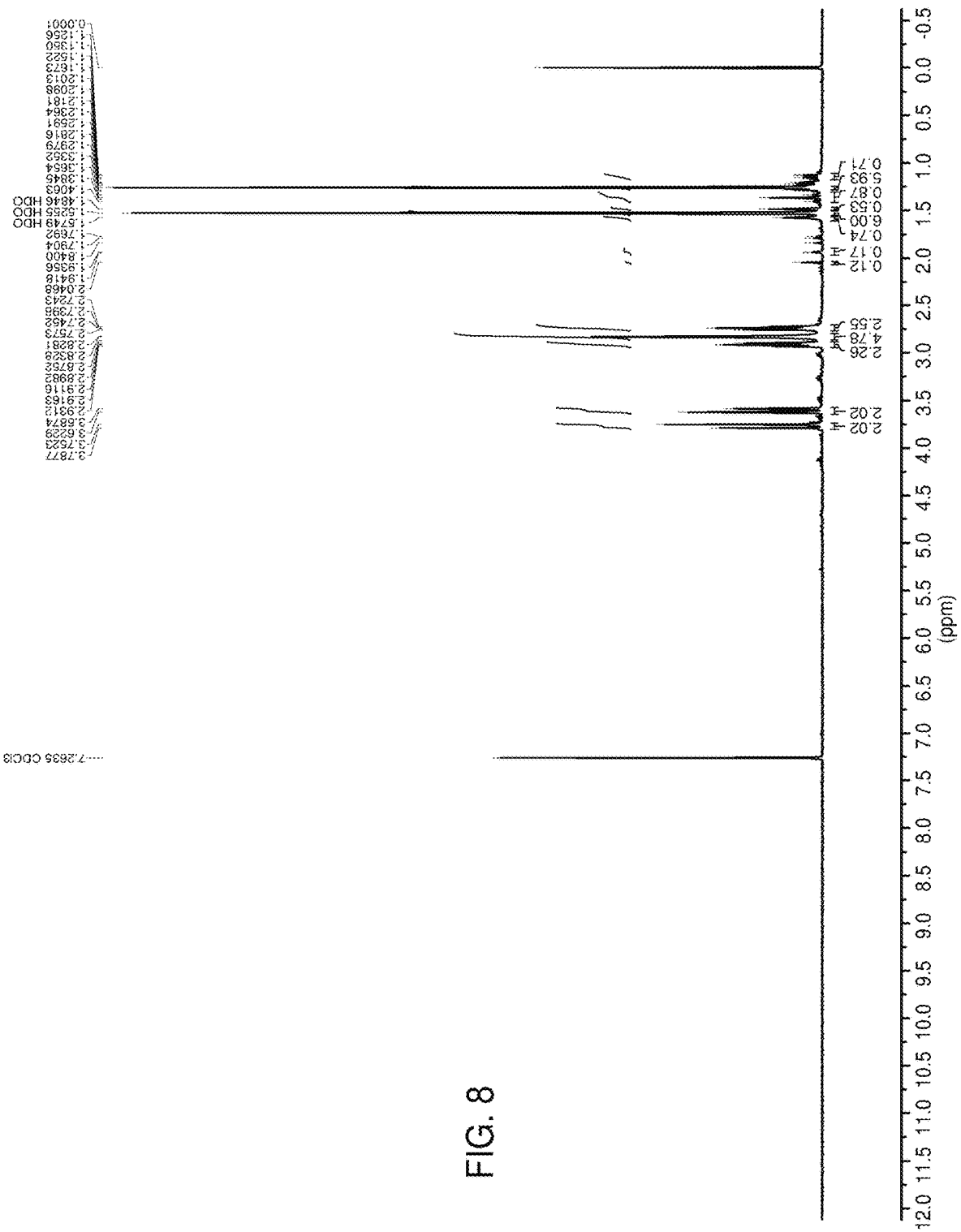
FIG. 8 [Example 3 Compound 4] TMTHSI-Suc-NHS analytical data.
Bruker BioSpin GmbH: Method Pulse Sequence: zg30. Relaxation Delay: 1 s. Solvent: $CDCl_3$. Temperature: ~298.2043 K. Number of Scans: 16. Frequency: 400.132470966543 MHz. Nucleus: 1H.
Figure 9:
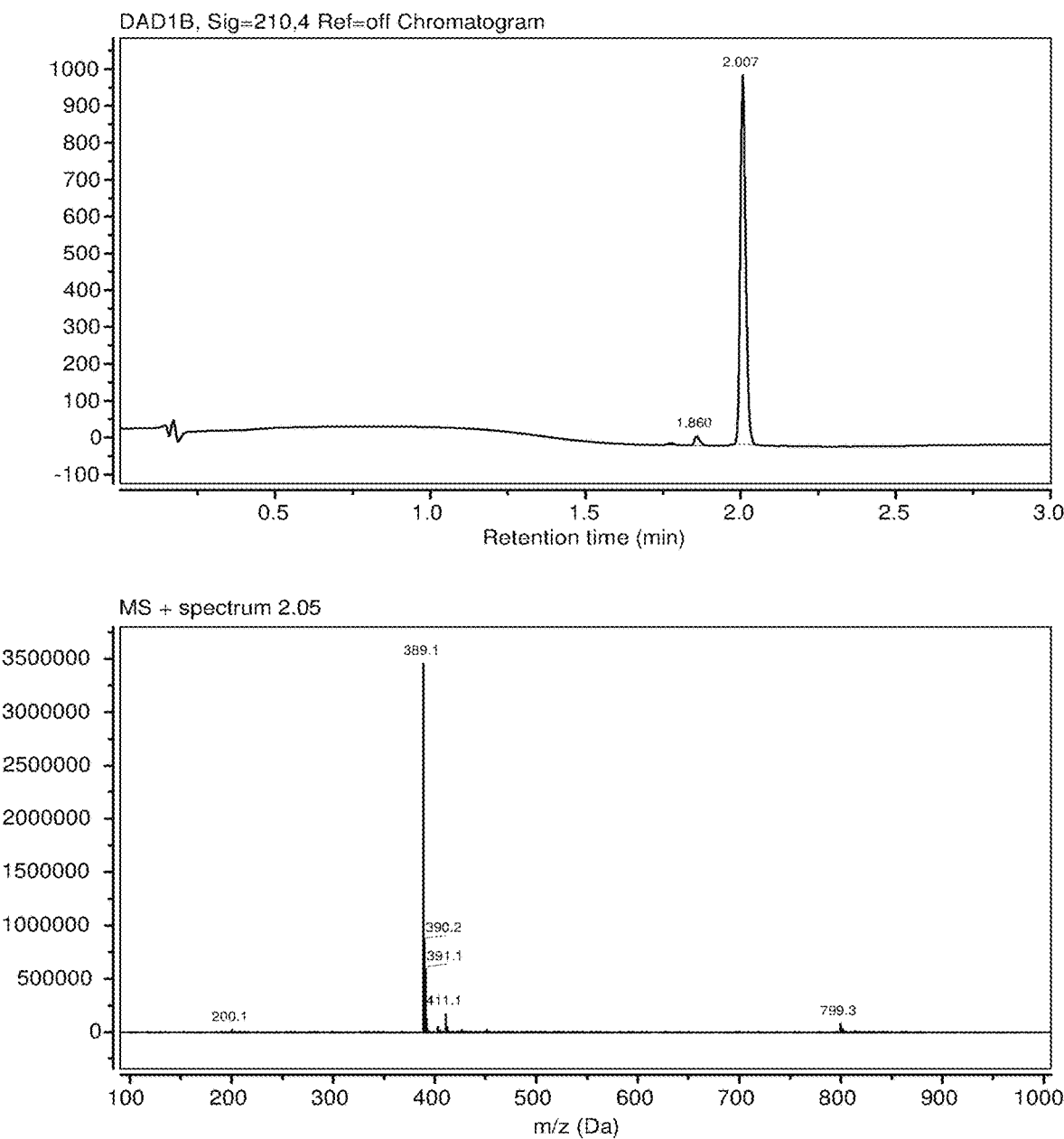
FIG. 9 [Example 3 Compound 4] TMTHSI-Suc-NHBn analytical data
Column: Waters XSelect CSH C18 (30×2.1 mm 3.5µ). Flow: 1 ml/min; Column Temp: 25° C. Eluent A: acetonitrile. Eluent B: 10 mM ammonium bicarbonate in water. Lin. Gradient t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).
Figure 10:
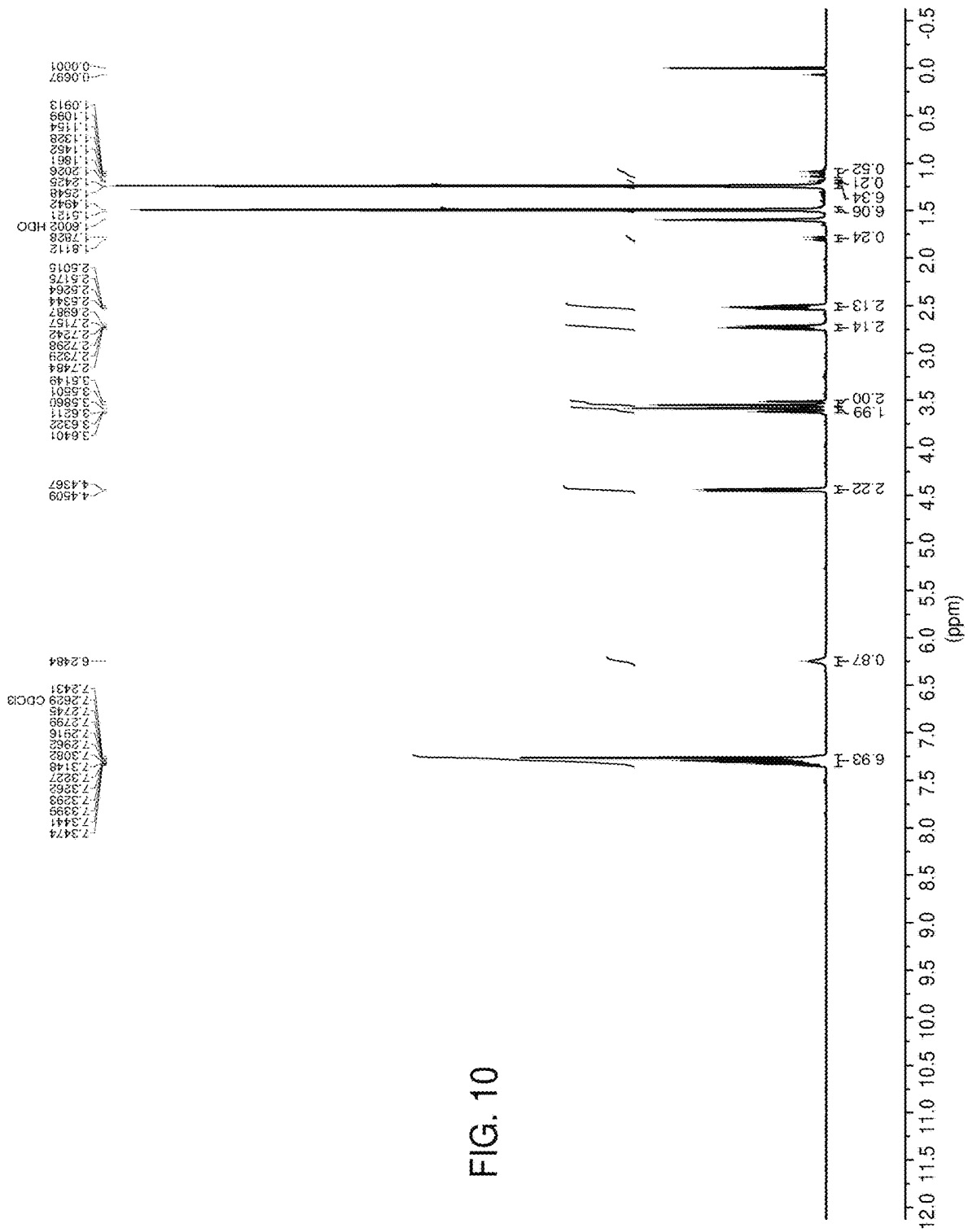
FIG. 10 [Example 3 Compound 4] TMTHSI-Suc-NHBn analytical data
Bruker BioSpin GmbH: Method Pulse Sequence: zg30. Relaxation Delay: 1 s. Solvent: $CDCl_3$. Temperature: ~298.5264 K. Number of Scans: 64. Frequency: 400.132470966543 MHz. Nucleus: 1H.
Figure 11:
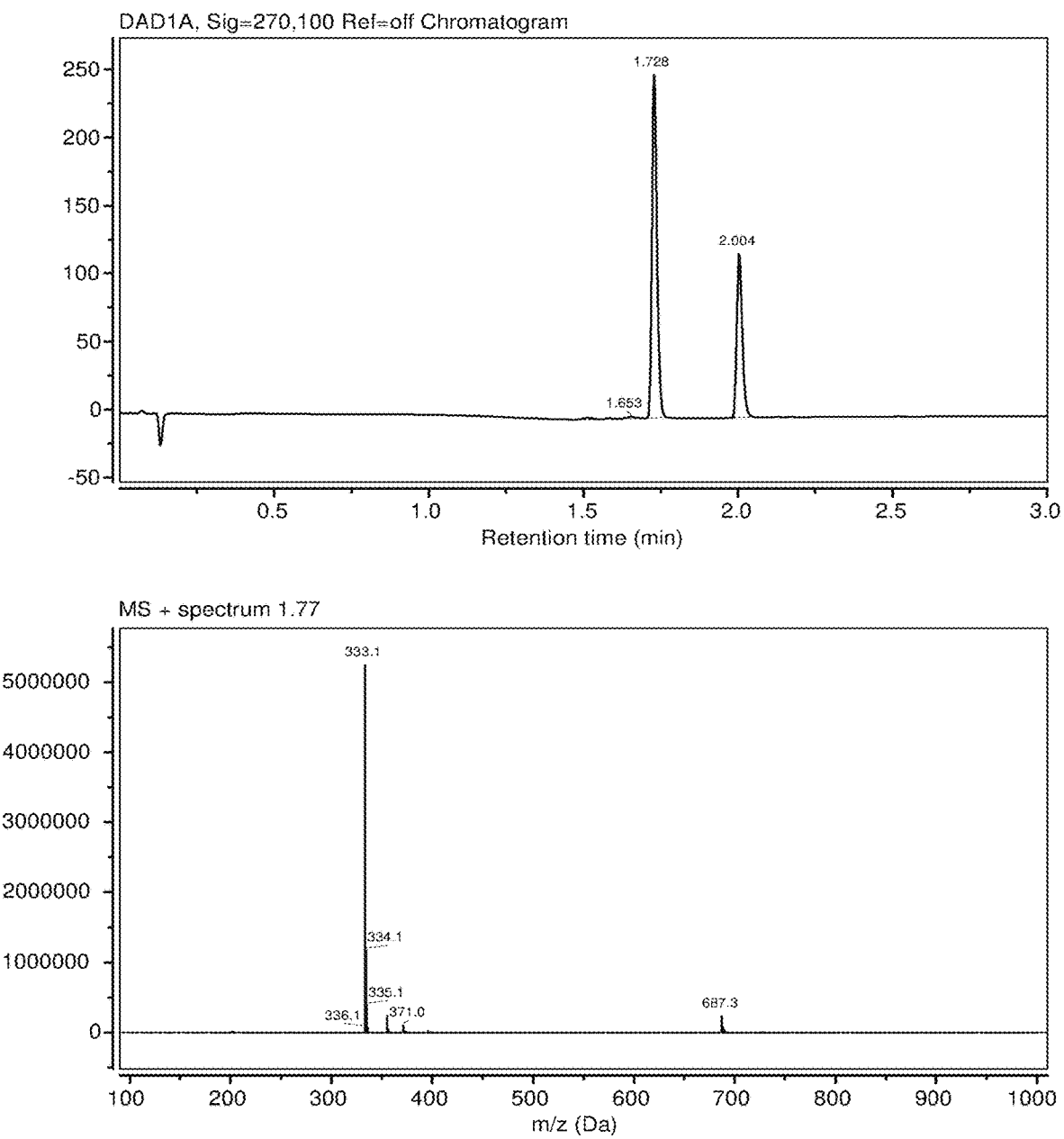
FIG. 11 [Example 5 Compound 6] PoC TMTHSI analytical data
Column: Waters XSelect CSH C18 (30×2.1 mm 3.5µ). Flow: 1 ml/min; Column Temp: 25° C. Eluent A: 95% acetonitrile+5% 10 mM ammonium bicarbonate in water. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection PDA (210-320 nm). Detection: MSD ESI pos/neg (mass range 100-1000).
Figure 12:
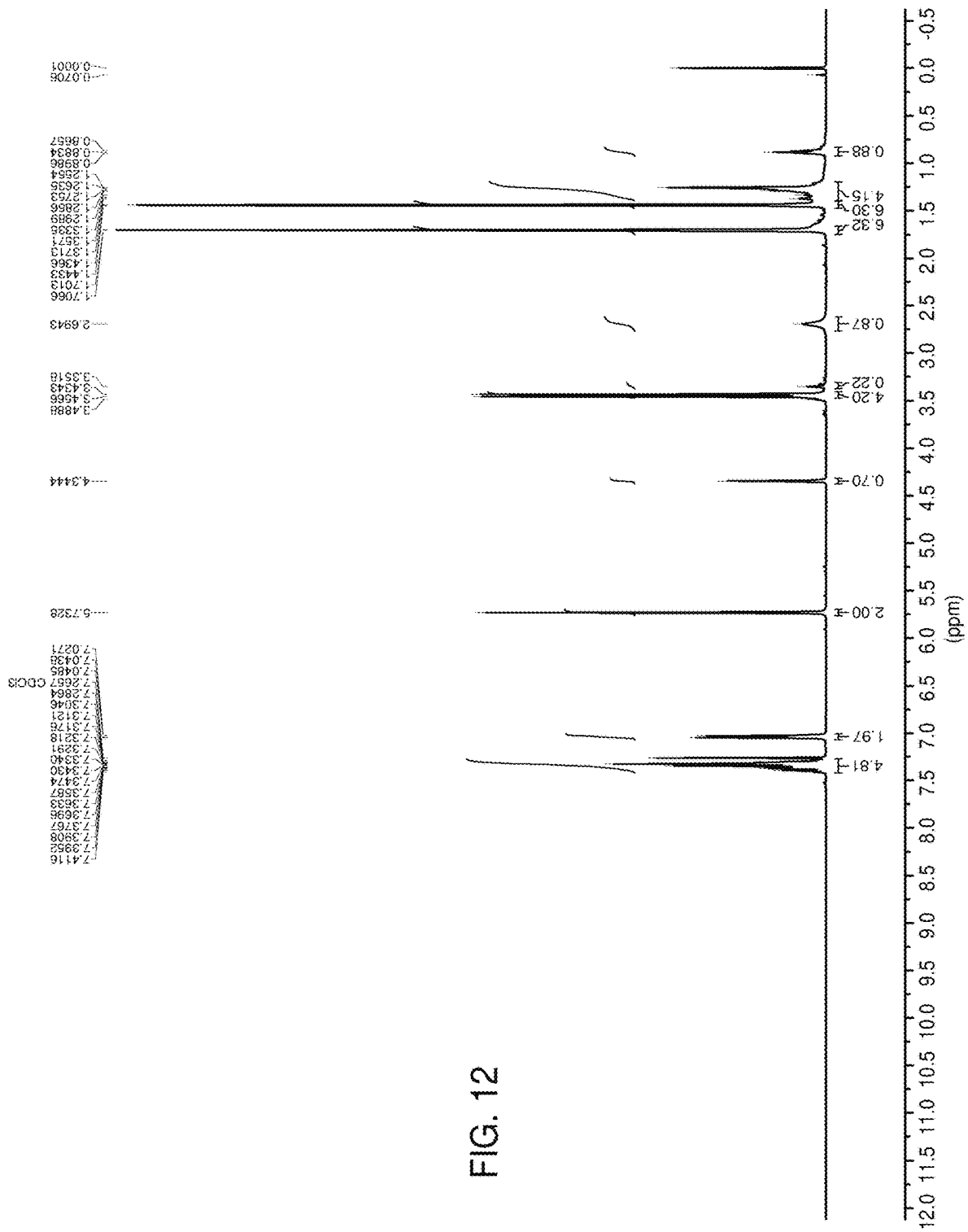
FIG. 12 [Example 5 Compound 6] PoC TMTHSI analytical data
Bruker BioSpin GmbH: Method Pulse Sequence: zg30. Relaxation Delay: 1 s. Solvent: $CDCl_3$. Temperature: ~297.6677 K. Number of Scans: 16. Frequency: 400.132470966543 MHz. Nucleus: 1H.
Figure 13:
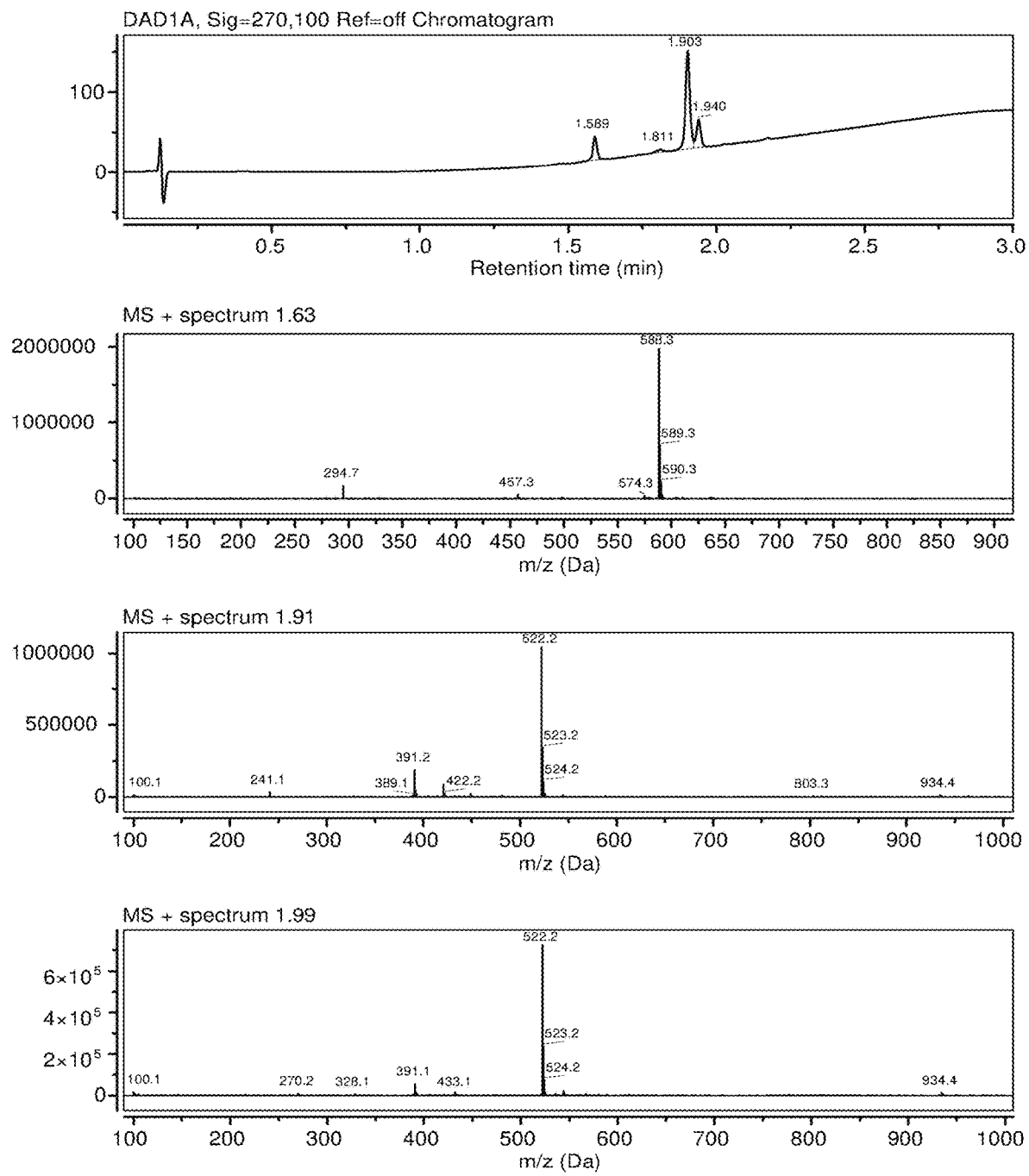
FIG. 13 [Example 6 Compound 9] PoC TMTHSI-Suc-NHBn analytical data
Column: Waters XSelect CSH C18 (30×2.1 mm, 3.5µ). Flow: 1 ml/min; Column temp: 35° C. Eluent A: 0.1% Formic acid in acetonitrile. Eluent B: 0.1% Formic acid in water. Lin. Gradient: t=0 min 5% A, t=1.6 min 98% A, t=3 min 98% A. Post time: 1.3 min. Detection DAD (220-320 nm, 210 and 220 nm). Detection: PDA (210-400 nm). Detection: MSD ESI pos/neg (mass range: 100-1000). Detection: ELSD (Alltech 3300): gas flow 1.5 ml/min, gas temp: 40° C.
Figure 14:
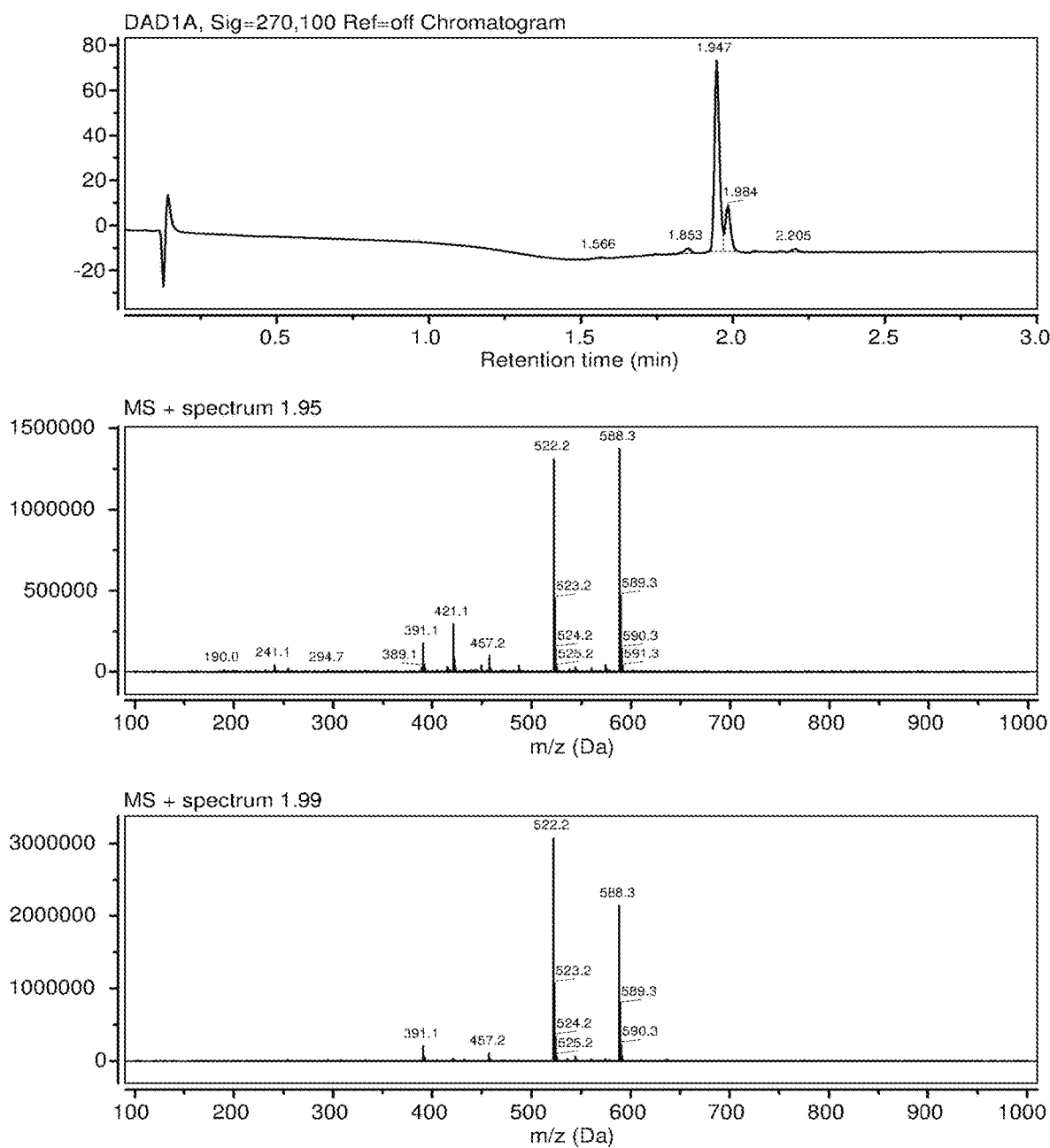
FIG. 14 [Example 6 Compound 9] PoC TMTHSI-Suc-NHBn analytical data
Column: Waters XSelect CSH C18 (30×2.1 mm 3.5µ). Flow: 1 ml/min; Column Temp: 25° C. Eluent A: acetonitrile. Eluent B: 10 mM ammonium bicarbonate in water. Lin. Gradient: t=0 min 5% A, t=1.6 min 98% A, t=3 min 98% A. Post time: 1.3 min. Detection: DAD (220-320 nm, 210 and 220 nm). Detection: PDA (210-320 nm). Detection: MSD ESI pos/neg (mass range 100-1000).
Figure 15:
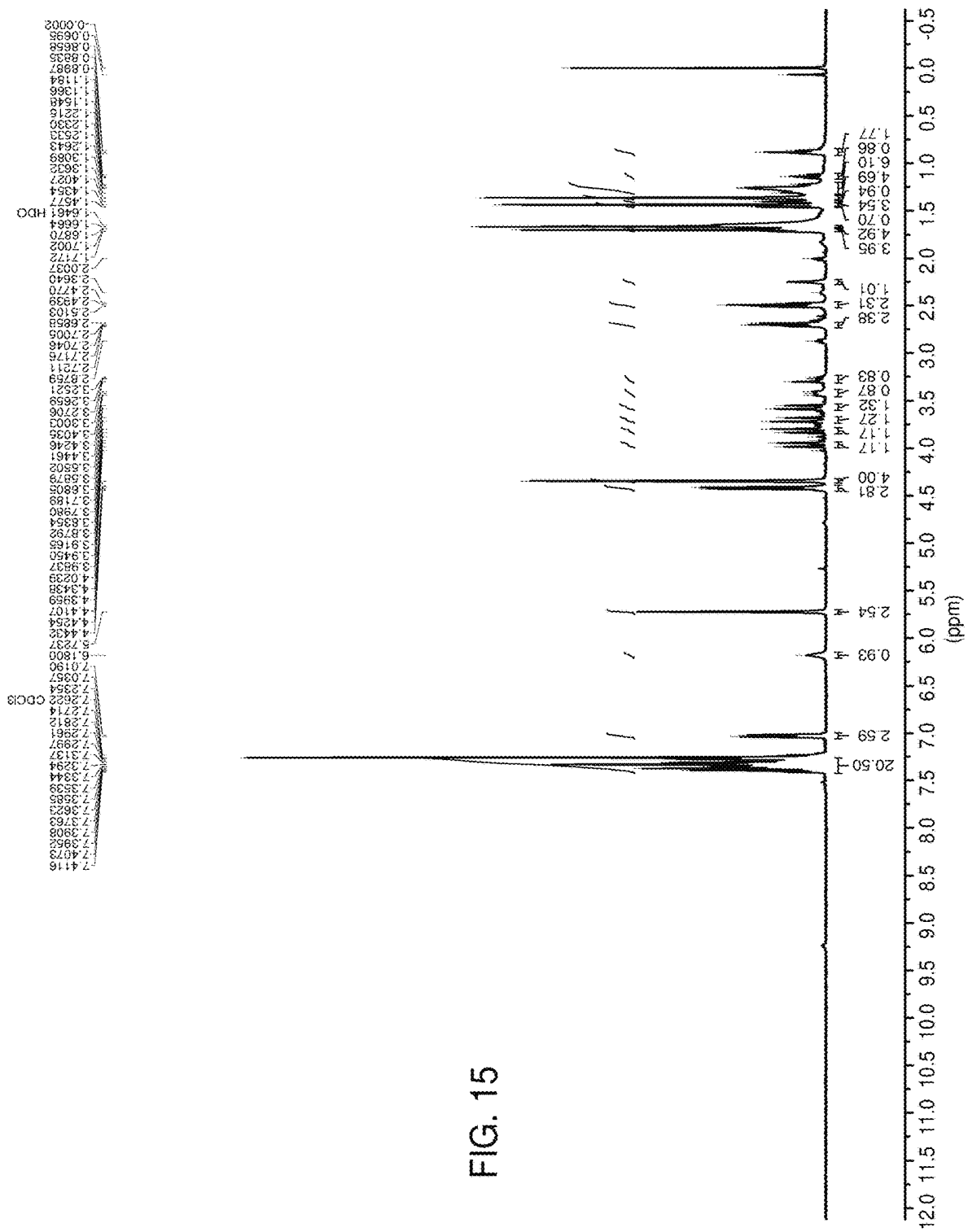
FIG. 15 [Example 6 Compound 9] PoC TMTHSI-Suc-NHBn analytical data
Bruker BioSpin GmbH: Method Pulse Sequence: zg30. Relaxation Delay: 1 s. Solvent: $CDCl_3$. Temperature: ~298.097 K. Number of Scans: 16. Frequency: 400.132470966543 MHz. Nucleus: 1H.
Figure 16:
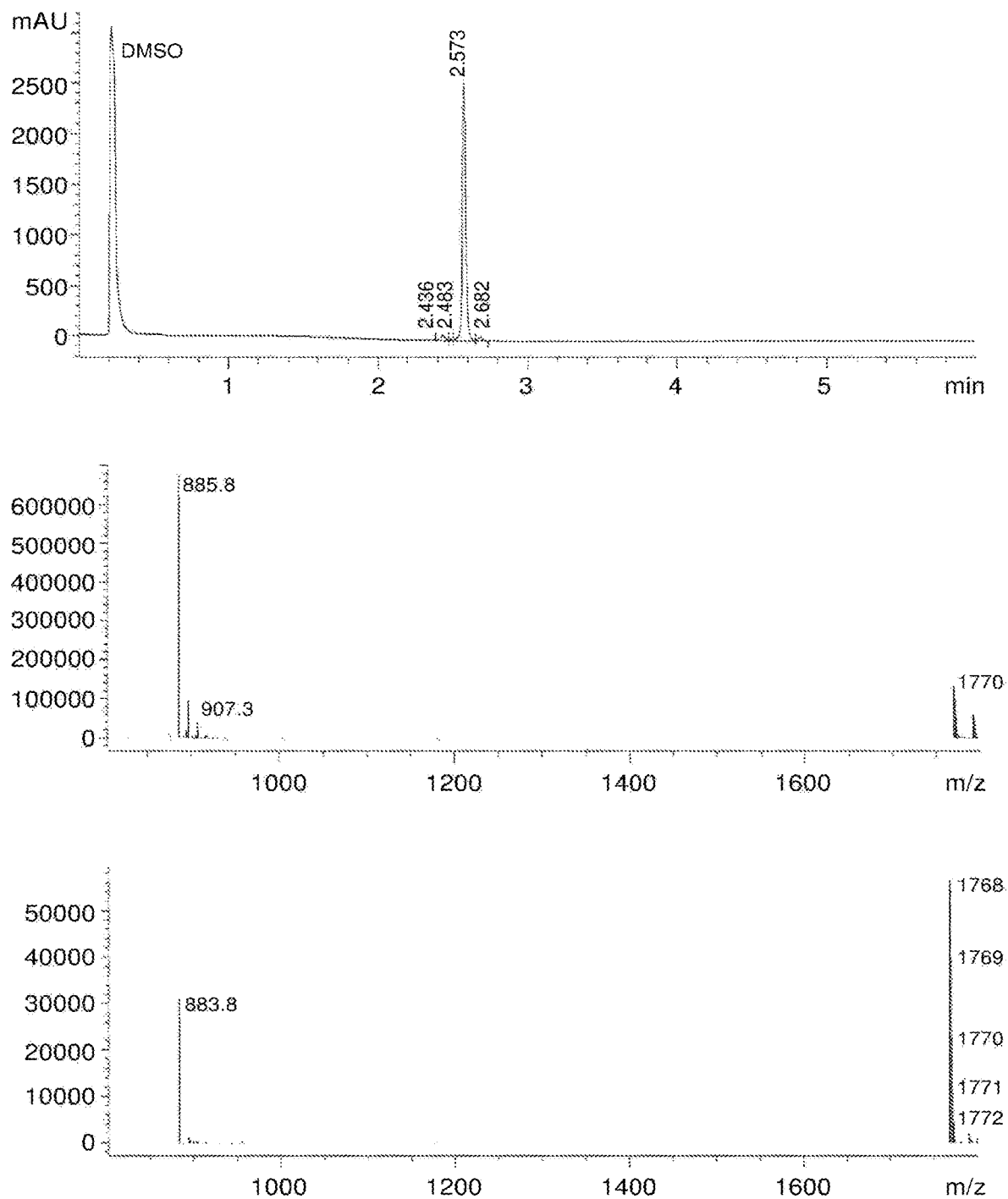
FIG. 16 [Example 8 Compound 8] TMTHSI-HER2 analytical data
Column: Waters XSelect CSH C18 (50×2.1 mm 3.5µ). Flow: 0.8 ml/min; Column Temp: 25° C. Eluent A: acetonitrile. Eluent B: 10 mM ammonium bicarbonate in water. Lin. Gradient: t=0 min 5% A, t=3.5 min 98% A, t=3 min 98% A. Post time: 2 min. Detection DAD (220-320 nm, 210 and 220 nm). Detection PDA (210-320 nm). Detection: MSD ESI pos/neg (mass range 100-1000).
Figure 17A:
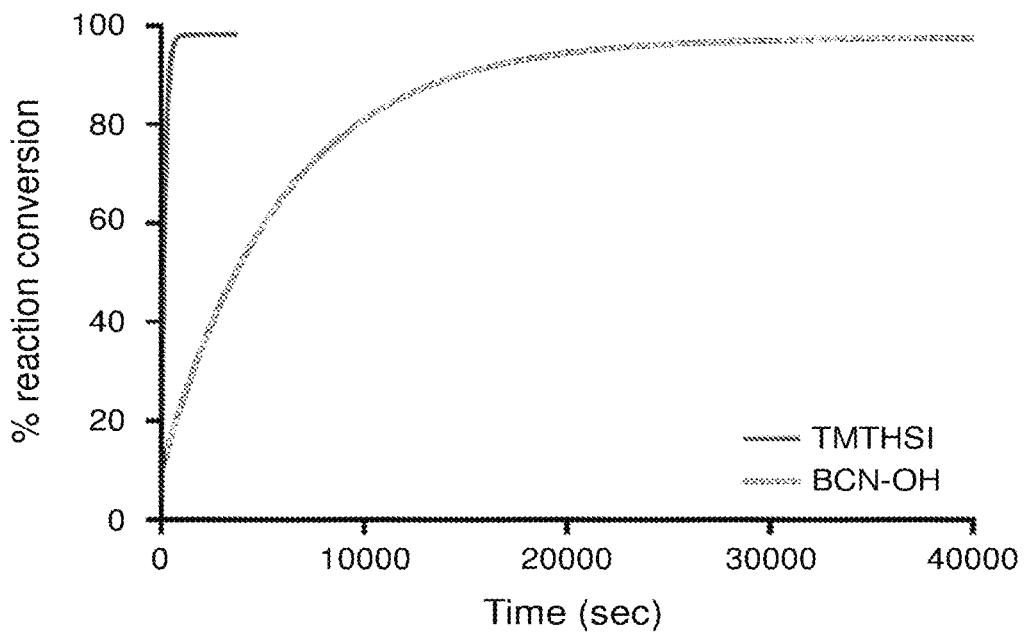
FIG. 17A comparison of reaction kinetics of TMTHSI with BCN-OH. TMTHSI (upper curve) is significantly faster than BCN-OH (lower curve).
Figure 17B:
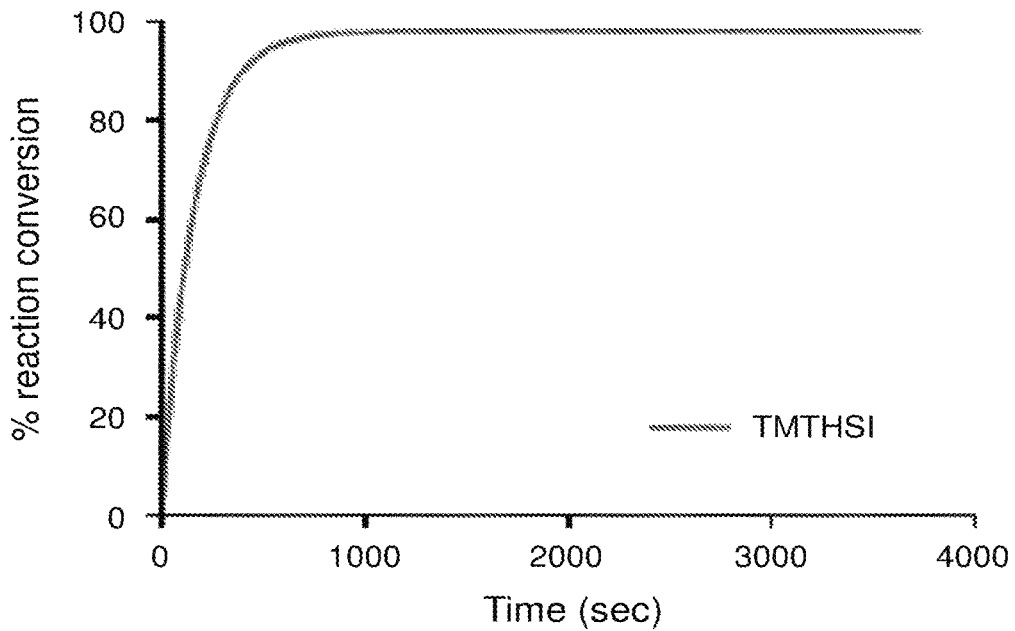
FIG. 17B An enlargement of the measurements for TMTHSI.

Example 10: Comparison of Reaction Kinetics of a Model Click Reaction Between TMTHSI and BCNOH and Benzyl Azide The alkyne (TMTSHI or BCN-OH) was reacted with 1.3 eq benzylazide and reaction kinetics were measured using NMR (CDCl$_3$). Conversion of TMTHSI with benzyl azide reached 79% after 225 seconds, the reaction with BCN-OH took about 40-fold longer (9312 seconds). The reaction conversion (%) is calculated based on triazole signals, taking the plateau of triazole signal at the end of reaction as 100% level=when all TMTHSI or BCN-OH fully reacted with benzylazide. The results of the measurements are included in FIG. 17A. TMTHSI (upper curve) is significantly faster than BCN-PH (lower curve). An enlargement of the measurements for TMTHSI is presented in FIG. 17B.

Example 11: Synthesis of $N^1$-(2-(2-(2-aminoethoxy)ethoxy)ethyl)-$N^4$-(3,3,6,6-tetramethyl-1-oxido-4,5-didehydro-2,3,6,7-tetrahydro-1$\lambda^6$-thiepan-1-ylidene)succinamide

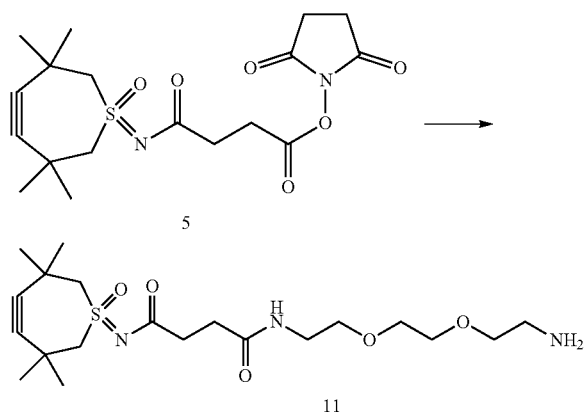

A solution of 2,5-dioxopyrrolidin-1-yl 4-oxo-4-((3,3,6,6-tetramethyl-1-oxido-4,5-didehydro-2,3,6,7-tetrahydro-1$\lambda^6$-thiepin-1-ylidene)amino)butanoate (89 mg, 0.22 mmol) in dichloromethane (2 ml) was added dropwise over 5 minutes to a solution of 1,2-bis(2-aminoethoxy)ethane (131 µl, 0.90 mmol, 4 eq.) in dichloromethane (5 ml). After addition was complete, the mixture was allowed to stir at room temperature for 15 minutes. Then the mixture was quenched with saturated aqueous NH$_4$Cl solution (5 ml) and the organic phase was pipetted over a phase separator. The aqueous residue was extracted with dichloromethane (2×) each time the organic phase was pipetted over a phase separator. The combined filtrates were concentrated under reduced pressure to afford 47.7 mg of the crude product. The residue was purified by preparative RP-MPLC (Reveleris, XSelect 10-50% MeCN in water, 10 mM NH$_4$HCO$_3$, pH=9.5) the product fractions were combined and concentrated under reduced pressure to ~15 ml and transferred to a 50 ml round bottom flask and lyophilised to afford 26 mg (27%) of the product as a white solid.

Figure 18:
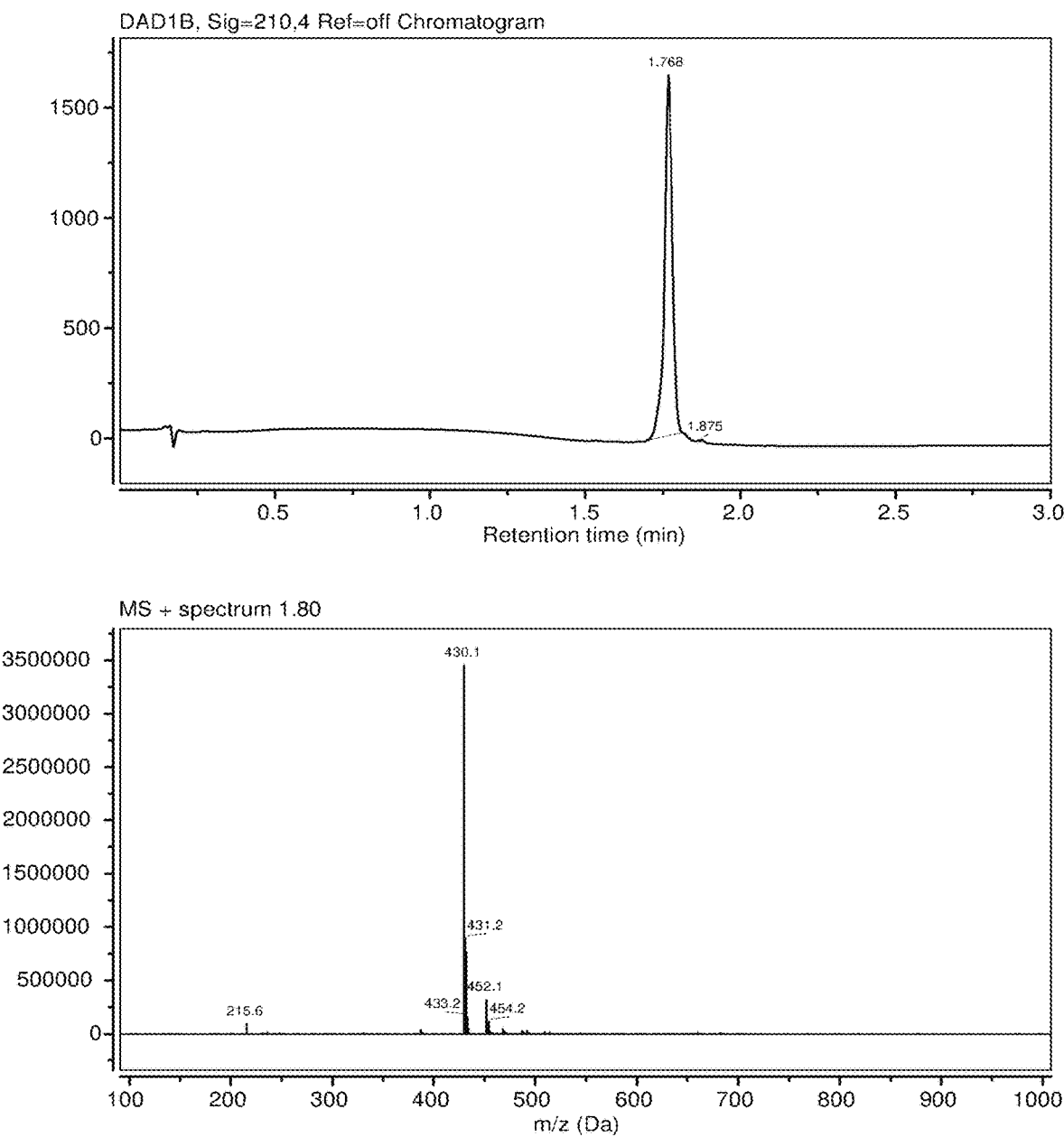
FIG. 18: [Example 11 Compound 11] LCMS and Mass data of $N^1$-(2-(2-(2-aminoethoxy)ethoxy)ethyl)-$N^1$-(3,3,6,6-tetramethyl-1-oxido-4,5-didehydro-2,3,6,7-tetrahydro-1$\lambda^6$-thiepan-1-ylidene)succinamide.

LC/MS (SC_BASE) $t_R$ 1.77 min, purity 99%, mass found [M+H]$^+$ 430. FIG. 18

$^1$H NMR (400 MHz, Chloroform-d) δ 6.73 (t, J=5.4 Hz, 1H), 3.68 (d, J=14.1 Hz, 2H), 3.63 (s, 4H), 3.59 (d, J=10.3 Hz, 2H), 3.57-3.52 (m, 4H), 3.45 (q, J=5.3 Hz, 2H), 2.90 (t, J=5.1 Hz, 2H), 2.69 (t, J=6.9 Hz, 2H), 2.48 (t, J=6.9 Hz, 2H), 2.16 (bs, 2H), 1.51 (s, 6H), 1.27 (s, 6H).

Example 12: Synthesis of 2,5-dioxopyrrolidin-1-yl (3,3,6,6-tetramethyl-1-oxido-4,5-didehydro-2,3,6,7-tetrahydro-1$\lambda^6$-thiepan-1-ylidene)carbamate

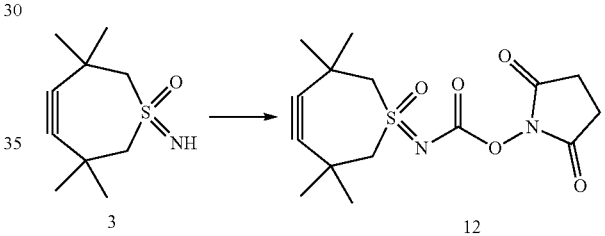

An 8 ml screwcap vial was charged with N,N'-disuccinimidyl carbonate (52 mg, 0.20 mmol, 2 eq.) and dissolved in acetonitrile (2 ml). To this, a solution of 1-imino-3,3,6,6-tetramethyl-4,5-didehydro-2,3,6,7-tetrahydro-1H-1$\lambda^6$-thiepine 1-oxide (20 mg, 0.1 mmol) in acetonitrile (1 ml) was drop wise, using a syringe. The mixture was stirred at room temperature for one hour. The mixture was diluted with a mixture of diethylether (15 ml) and ethyl acetate (15 ml) and quenched with water. The organic layer was washed again with water, followed by brine, dried over Na$_2$SO$_4$ and concentrated under reduced pressure to afford 117 mg of the crude product as a white solid. The residue was purified by flash column chromatography (silica, 4 g; 20-50% EtOAc in heptane), the product fractions were combined and concentrated under reduced pressure to afford 49 mg (43%) of the product as a white fluffy solid.

LC/MS (SC_BASE) $t_R$ 1.97 min, purity, 95%, mass found [M+Na]$^+$ 363, [2M+Na]$^+$ 703.

$^1$H NMR (400 MHz, Chloroform-d) δ 3.92 (d, J=14.2 Hz, 2H), 3.45 (d, J=14.2 Hz, 2H), 2.80 (s, 4H), 1.52 (s, 6H), 1.29 (s, 6H).

TMTHSI was proven to be stable during storage. Compound 12 was stored as a powder at both light and dark locations under atmospheric pressure. $^1$H-NMR en LC/MS (SC_BASE) proved the compound was still in tact after 4 months of storage.

Example 13: Synthesis of 2,2,2-trifluoro-N-(3,3,6,6-tetramethyl-1-oxido-4,5-didehydro-2,3,6,7-tetrahydro-1λ⁶-thiepin-1-ylidene)acetamide

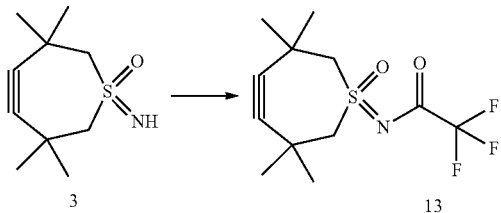 [SMILES: CC1(C)C#CC(C)(C)CS(=N)(=O)C1 ; CC1(C)C#CC(C)(C)CS(=O)(=NC(=O)C(F)(F)F)C1]

An 8 ml screwcap vial was charged with TMTHSI (50 mg, 0.25 mmol) and the material was dissolved in acetonitrile (2 ml). $K_2CO_3$ (69 mg, 0.50 mmol, 2 eq.) was added followed by trifluoroacetic anhydride (38 μl, 0.27 mmol, 1.1 eq.). The mixture was stirred at room temperature for one hour. The mixture was diluted with diethyl ether and washed with water (2×). The organic layer was washed with brine, dried over $Na_2SO_4$ and concentrated under reduced pressure to afford 56 mg of the crude product as a white solid.

The residue was purified by preparative RP-MPLC (Reveleris Prep, LUNA-C18, 20-60% MeCN in water, 0.1% (v/v) formic acid). The product fractions were combined and lyophilised to afford 35 mg (47%) of the product as a white solid.

LC/MS (SC_BASE) $t_R$ 2.18 min, purity 99.0%, mass found [M+H]⁺ 296.

¹H NMR (400 MHz, Chloroform-d) δ 3.86 (d, J=14.1 Hz, 2H), 3.66 (d, J=14.1 Hz, 2H), 1.57 (s, 6H), 1.33 (s, 6H).

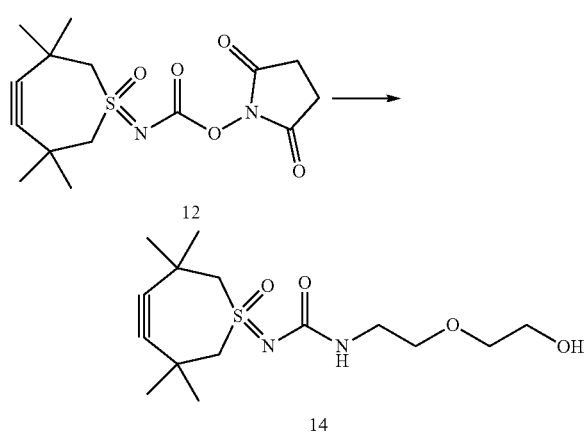

Example 14: Synthesis of 1-(2-(2-hydroxyethoxy)ethyl)-3-(3,3,6,6-tetramethyl-1-oxido-4,5-didehydro-2,3,6,7-tetrahydro-1γ⁶-thiepin-1-ylidene)urea An 8 ml screwcap vial was charged with 2-(2-aminoethoxy)ethanol (29 μl, 0.29 mmol, 2 eq.) and diisopropylethylamine (63 μl, 0.36 mmol, 2.5 eq.) and dissolved in dichloromethane (2 ml). A suspension of 2,5-dioxopyrrolidin-1-yl (3,3,6,6-tetramethyl-1-oxido-4,5-didehydro-2,3,6,7-tetrahydro-1λ⁶-thiepan-1-ylidene)carbamate (49 mg, 0.14 mmol) in dichloromethane (1 ml) was added slowly via pipette and the mixture was stirred at room temperature for 16 hours. The mixture was diluted with water and extracted with dichloromethane (3×), each organic layer was filtered over a phase separator. The combined organic extracts were concentrated under reduced pressure to afford 43 mg of the crude product. The residue was purified by preparative RP-MPLC (Reveleris, XSelect 10-50% MeCN in water, 10 mM $NH_4HCO_3$, pH=9.5), product fractions were combined and lyophilised to afford 12 mg (25%) of the product as a fluffy solid.

LC/MS (SC_BASE) $t_R$ 1.73 min, purity 94%, mass found [M+H]⁺ 331.

¹H NMR (400 MHz, Chloroform-d) δ 5.41-5.30 (m, 1H), 3.84-3.75 (m, 2H), 3.75-3.70 (m, 2H), 3.60-3.53 (m, 4H), 3.48 (d, J=14.1 Hz, 2H), 3.43-3.34 (m, 2H), 1.49 (s, 6H), 1.27 (s, 6H).

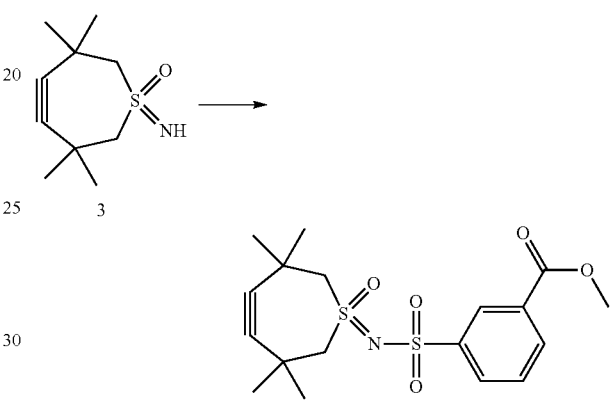

Example 15: Synthesis of methyl 3-(N-(3,3,6,6-tetramethyl-1-oxido-4,5-didehydro-2,3,6,7-tetrahydro-1λ⁶-thiepin-1-ylidene)sulfamoyl)benzoate An 8 ml screwcap vial was charged with 1-imino-3,3,6,6-tetramethyl-4,5-didehydro-2,3,6,7-tetrahydro-1H-1λ⁶-thiepine 1-oxide (57 mg, 0.28 mmol) and dissolved in dichloromethane (1.5 ml), pyridine was added (50 μl, 0.62 mmol, 2.16 eq.) and the mixture as stirred for 15 minutes. Methyl 3-(chlorosulfonyl)benzoate (81 mg, 0.34 mmol, 1.5 eq.) was added and the mixture was stirred at room temperature for 3 hours. The mixture was quenched in aqueous 0.1 N HCl solution (15 ml) and extracted with dichloromethane (3×), each organic extract was filtered over a phase separator. The combined extracts were concentrated under reduced pressure to afford 100 mg of the crude product as an oily residue. The residue was purified by preparative RP-MPLC (Reveleris, LUNA-C18, 30-70% MeCN in water, 0.1% (v/v) formic acid). The product fractions were combined and lyophilised to afford 39 mg (34%) of the product as a white fluffy solid.

LC/MS (SC_BASE) $t_R$ 2.16 min, purity 100%, mass found [M+H]⁺ 398.

¹H NMR (400 MHz, Chloroform-d) δ 8.65-8.61 (m, 1H), 8.21 (d, J=7.8 Hz, 1H), 8.17 (d, J=7.9 Hz, 1H), 7.58 (t, J=7.8 Hz, 1H), 4.08 (d, J=14.3 Hz, 2H), 3.95 (s, 3H), 3.41 (d, J=14.2 Hz, 2H), 1.49 (s, 6H), 1.28 (s, 6H).

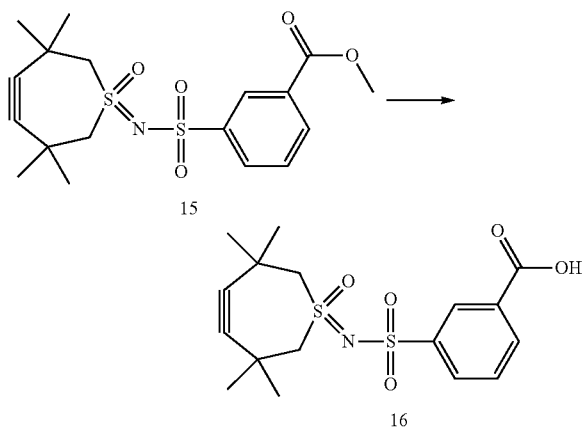

Example 16: Synthesis of 3-(N-(3,3,6,6-tetramethyl-1-oxido-4,5-didehydro-2,3,6,7-tetrahydro-1λ⁶-thiepin-1-ylidene)sulfamoyl)benzoic Acid An 8 ml screwcap vial was charged with 3-(N-(3,3,6,6-tetramethyl-1-oxido-4,5-didehydro-2,3,6,7-tetrahydro-1λ⁶-thiepin-1-ylidene)sulfamoyl)benzoate (29 mg, 73 μmol) and the material was dissolved in THF (0.5 ml). A solution of LiOH E20 (7 mg, 167 μmol, 2.3 eq.) in water (0.5 ml). The resulting mixture was stirred at room temperature for 16 hours. The reaction mixture was purified by preparative RP-MPLC (Reveleris, LUNA-C18, 30-70% MeCN in water, 0.1% (v/v) formic acid). The product fractions were combined and lyophilised to afford 26 mg (93%) of the product as white fluffy solid.

LC/MS (SC_BASE) $t_R$ 1.70 min, purity 98%, mass found [M+H]⁺ 384.

¹H NMR (400 MHz, Chloroform-d) δ 8.70 (t, J=1.8 Hz, 1H), 8.26 (d, J=7.7 Hz, 1H), 8.22 (d, J=7.8 Hz, 1H), 7.62 (t, J=7.8 Hz, 1H), 4.10 (d, J=14.3 Hz, 2H), 3.42 (d, J=14.2 Hz, 2H), 1.49 (s, 6H), 1.29 (s, 6H).

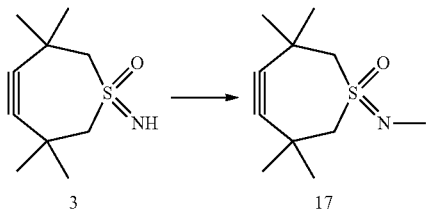

Example 17: Synthesis of 3,3,6,6-tetramethyl-1-(methylimino)-4,5-didehydro-2,3,6,7-tetrahydro-1H-1λ⁶-thiepine 1-oxide An 8 ml screwcap vial was charged with 1-imino-3,3,6,6-tetramethyl-4,5-didehydro-2,3,6,7-tetrahydro-1H-1λ⁶-thiepine 1-oxide (50 mg, 0.25 mmol) and dissolved in THF (1 ml), the solution was treated with KOtBu (1.7 M in THF; 200 μl, 1.35 eq.). The resulting suspension was stirred for 5 minutes, then iodomethane (30 μl, 0.48 mmol, 1.9 eq.) was added and the mixture was stirred at room temperature for 2 hours. The mixture was diluted with diethylether and quenched with water. The layers were separated and the aqueous layer was extracted with diethylether (2×). The combined organic layers were washed with brine, dried over Na₂SO₄ and concentrated under reduced pressure to afford 44 mg of the crude product as a clear oil. The residue was purified by preparative RP-MPLC (Reveleris, XSelect 10-50% MeCN in water, 10 mM NH₄HCO₃, pH=9.5), the product fractions were combined and concentrated under reduced pressure. The residue was diluted with acetonitrile and lyophilised to afford 31.3 mg (58%) of the product as a white solid.

LC/MS (SC_BASE) $t_R$ 1.79 min, purity 99%, mass found [M+H]⁺ 214.

¹H NMR (400 MHz, Chloroform-d) δ 3.32 (d, J=13.9 Hz, 2H), 3.07 (d, J=14.0 Hz, 2H), 2.84 (s, 3H), 1.43 (s, 6H), 1.28 (s, 6H).

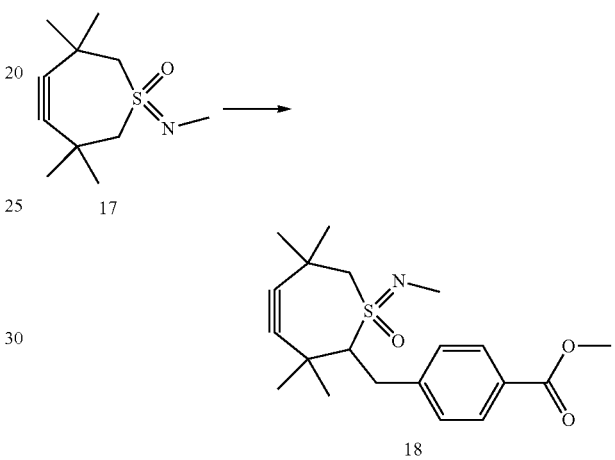

Example 18: Synthesis of methyl 4-((3,3,6,6-tetramethyl-1-(methylimino)-1-oxido-4,5-didehydro-2,3,6,7-tetrahydro-1H-1λ⁶-thiepin-2-yl)methyl)benzoate An 8 ml screwcap vial was charged with 3,3,6,6-tetramethyl-1-(methylimino)-4,5-didehydro-2,3,6,7-tetrahydro-1H-1λ⁶-thiepine 1-oxide (31 mg, 0.14 mmol) and dissolved in anhydrous THF (1 ml). LiHMDS (1M in THF; 174 μl, 0.17 mmol, 1.2 eq.) was added and the mixture was stirred at room temperature for 15 minutes, then methyl 4-(bromomethyl)benzoate (50 mg, 0.22 mmol, 1.5 eq) was added and the mixture was stirred at room temperature for 20 hours. The mixture was quenched in water and extracted with diethylether (3×10 ml). The combined organic layers were washed with brine and concentrated under reduced pressure to afford a semi-solid residue. The residue was purified by preparative RP-MPLC (Reveleris, LUNA-C18, 30-70% MeCN in water, 0.1% (v/v) formic acid). The product fractions were combined and lyophilised to afford 9 mg (17%) of the product as a white fluffy solid.

LC/MS (SC_BASE) $t_R$ 2.20 min, purity 97%, mass found [M+H]⁺ 362.

¹H NMR (400 MHz, Chloroform-d) δ 7.97 (d, J=8.2 Hz, 2H), 7.43 (d, J=8.2 Hz, 2H), 6.72 (d, J=15.7 Hz, 1H), 6.25 (d, J=15.8 Hz, 1H), 3.91 (s, 3H), 3.81-3.69 (m, 1H), 3.02 (d, J=12.8 Hz, 1H), 2.83-2.76 (m, 4H), 1.44 (s, 3H), 1.39 (s, 3H), 1.37 (s, 6H).

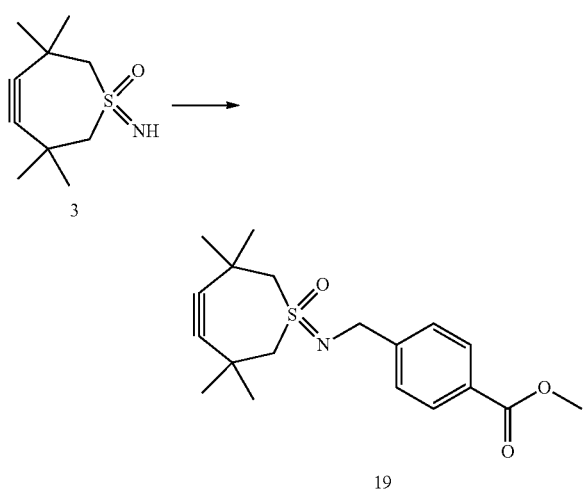

Example 19: Synthesis of methyl 4-(((3,3,6,6-tetramethyl-1-oxido-4,5-didehydro-2,3,6,7-tetrahydro-1l6-thiepin-1-ylidene)amino)methyl)benzoate An 8 ml screwcap vial was charged with 1-imino-3,3,6,6-tetramethyl-4,5-didehydro-2,3,6,7-tetrahydro-1H-1λ⁶-thiepine 1-oxide (75 mg, 0.37 mmol) and dissolved in anhydrous THF (1.5 ml). KOtBu (1.7 M soln in THF; 280 µl, 0.47 mmol, 1.26 eq.) was added and the resulting mixture was stirred at room temperature for 15 minutes. Methyl-4(bromomethyl)benzoate (129 mg, 0.56 mmol, 1.5 eq.) was added to the resulting suspension and the mixture was stirred at room temperature for 6 hours. The mixture was quenched in water and extracted with diethylether (3×15 ml), the combined organic extracts were washed with brine, dried over Na$_2$SO$_4$ and concentrated under reduced pressure to afford 128 mg of the crude product as a semi-solid residue. The residue was purified by preparative RP-MPLC (Reveleris, LUNA C18, 30-70% MeCN in water, 0.1% (v/v) formic acid). The product fractions were combined and lyophilised to afford 28 mg (21%) of the product as an oily residue.

LC/MS (SC_BASE) $t_R$ 2.14 min, purity 86%, mass found [M+H]⁺ 348.

¹H NMR (400 MHz, Chloroform-d) δ 7.99 (d, J=8.3 Hz, 2H), 7.46 (d, J=8.0 Hz, 2H), 4.39 (s, 2H), 3.91 (s, 3H), 3.35 (d, J=14.0 Hz, 2H), 3.18 (d, J=14.1 Hz, 2H), 1.45 (s, 6H), 1.28 (s, 6H).

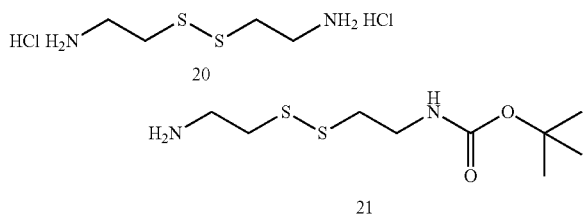

Example 20: Synthesis of tert-butyl (2-((2-aminoethyl)disulfaneyl)ethyl) carbamate A 250 ml round bottom flask was charged with bis-(2-aminoethyl)disulfide dihydrochloride (1.49 g, 6.62 mmol) and MeOH (75 ml). Triethylamine (2.89 ml, 20.8 mmol, 3.15 eq.) was added and when all solids were dissolved, di-tert-butyl dicarbonate (1.45 g, 6.64 mmol, 1 eq.) was added. The mixture was stirred at room temperature for approximately 1 hour.

The mixture was quenched by the addition of aqueous 1M NaH$_2$PO$_4$ (50 ml) and the organic solvent was removed by evaporation. The aqueous residue was washed with diethyl ether (3×30 ml), then rendered alkaline using aqueous 1N NaOH solution (~70 ml). The aqueous mixture was extracted with diethyl ether (3×60 ml). The combined organic extracts were dried over Na$_2$SO$_4$ and concentrated under reduced pressure to afford 0.71 g of a colourless oil. The aqueous layers were extracted further with dichloromethane (3×50 ml), the combined organic extracts were dried over Na$_2$SO$_4$ and concentrated with the previously isolated amount to afford 0.78 g (46%) of the product as a clear thick oil.

LC/MS (SC_BASE) $t_R$ 1.83 min, purity 98%, mass found [M+H]⁺ 253.

¹H NMR (400 MHz, Chloroform-d) δ 4.93 (s, 1H), 3.53-3.39 (m, 2H), 3.03 (t, J=6.2 Hz, 2H), 2.84-2.74 (m, 4H), 1.62 (s, 2H), 1.45 (s, 9H).

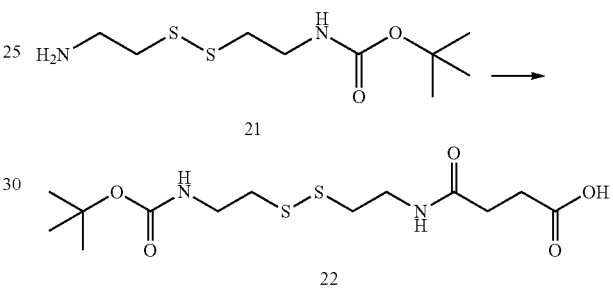

Example 21: Synthesis of 2,2-dimethyl-4,13-dioxo-3-oxa-8,9-dithia-5,12-diazahexadecan-16-oic Acid A 250 ml round bottom flask was charged with tert-butyl (2-((2-aminoethyl)di-sulfaneyl)ethyl)carbamate (0.78 g, 3.09 mmol) and the material was dissolved in dichloromethane (25 ml). DMAP (0.11 g, 0.93 mmol, 0.3 eq.) was added followed by succinic anhydride (0.3 g, 3.09 mmol, 1 eq.). The resulting mixture was stirred at room temperature for 1 hour. The mixture was quenched with aqueous 1N KHSO$_4$ solution (30 ml), the layers were separated and the organic layer was washed with aqueous 1N KHSO$_4$ solution (~30 ml). The combined aqueous layers were extracted with dichloromethane (30 ml), the combined organic layers were washed with brine, dried over Na$_2$SO$_4$ and concentrated under reduced pressure to afford 1.02 g (94%) of the crude product as a solid.

LC/MS (SC_ACID) $t_R$ 1.80 min, purity 100%, mass found [M+Na]⁺ 375, [M−H]⁻ 351.

¹H NMR (400 MHz, Chloroform-d) δ 11.57 (bs, 1H), 7.02 (t, J=5.9 Hz, 1H), 5.07 (t, J=6.3 Hz, 1H), 3.59 (q, J=5.9 Hz, 2H), 3.53-3.34 (m, 2H), 2.86 (t, J=6.0 Hz, 2H), 2.77 (t, J=7.2 Hz, 2H), 2.73-2.66 (m, 2H), 2.64-2.47 (m, 2H), 1.45 (s, 9H).

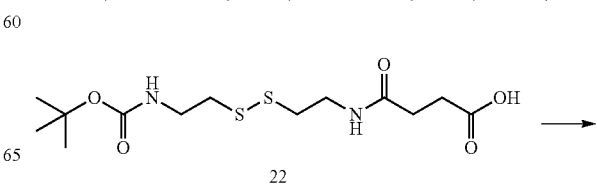

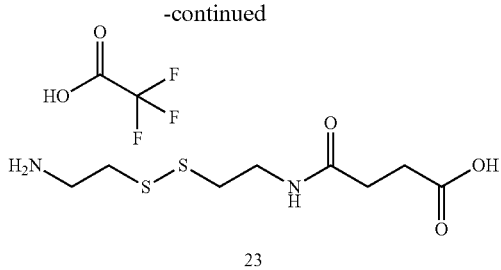

23

Example 22: Synthesis of 4-((2-((2-aminoethyl)disulfaneyl)ethyl)amino)-4-oxobutanoic acid trifluoroacetate Salt A 250 ml round bottom flask was charged with 2,2-dimethyl-4,13-dioxo-3-oxa-8,9-dithia-5,12-diazahexadecan-16-oic acid (1.02 g, 2.89 mmol). The material was dissolved in dichloromethane (5 ml) and treated with trifluoroacetic acid (3 ml, 39.2 mmol, 13.5 eq.). The reaction was stirred at room temperature for approximately 1 hour. The reaction was concentrated under reduced pressure, co-evaporated with toluene, dichloromethane and diethyl ether to afford 1.4 g (132%)

The residue was dissolved in water and washed with dichloromethane (3×). The aqueous layer was lyophilised to afford 1.04 g (98%) of the product as a thick clear oil.

$^1$H NMR (400 MHz, Methanol-$d_4$) δ 3.51 (dt, J=8.4, 6.4 Hz, 2H), 3.36-3.23 (m, 2H, coincides with Methanol-d4 residual peak), 2.99 (dq, J=8.4, 6.1, 5.6 Hz, 2H), 2.86 (dt, J=8.8, 6.6 Hz, 2H), 2.61 (dt, J=8.5, 6.4 Hz, 2H), 2.49 (dt, J=8.7, 6.5 Hz, 2H).

Example 23: Synthesis of 4-oxo-4-((2-((2-(3-(3,3,6,6-tetramethyl-1-oxido-4,5-didehydro-2,3,6,7-tetrahydro-1λ$^6$-thiepin-1-ylidene)ureido)ethyl)disulfaneyl)ethyl)amino)butanoic Acid An 8 ml screw cap vial was charged with 2,5-dioxopyrrolidin-1-yl (3,3,6,6-tetramethyl-1-oxido-4,5-didehydro-2,3,6,7-tetrahydro-1λ$^6$-thiepan-1-ylidene)carbamate (98 mg, 0.29 mmol) and the material was suspended/dissolved in acetonitrile (1 ml). DIPEA (115 µl, 0.66 mmol, 2.3 eq.) was added, followed by the addition of a solution of 4-((2-((2-aminoethyl)disulfaneyl)ethyl)amino)-4-oxobutanoic acid TFA-salt (113 mg, 0.31 mmol, 1.07 eq.) in water (0.5 ml) to form a suspension. An extra amount of acetonitrile (0.5 ml) was added and the mixture was stirred at room temperature for 20 hrs.

The reaction mixture was purified by preparative RP-MPLC (Reveleris Prep, LUNA-C18, 10-50% MeCN in water, 0.1% (v/v) formic acid). The product fractions were combined and lyophilised to afford 38 mg (28%) of the product.

LC/MS (SC_ACID) $t_R$ 1.77 min, purity 96%, mass found [M+H]$^+$ 478.

$^1$H NMR (400 MHz, Chloroform-d) δ 7.73 (s, 1H), 6.52 (s, 0.2H), 6.00 (s, 0.8H), 3.91-3.76 (m, 2H), 3.58-3.38 (m, 6H), 2.92-2.73 (m, 4H), 2.59-2.36 (m, 4H), 1.49 (s, 6H), 1.31 (s, 6H).

12   23

24

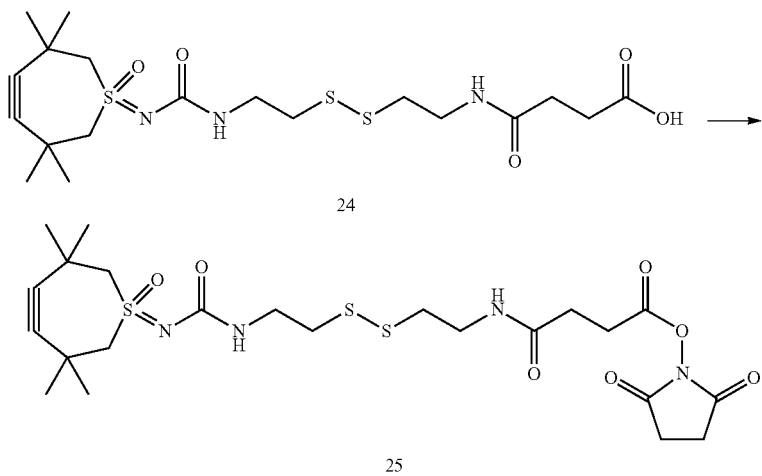

Example 24: Synthesis of 2,5-dioxopyrrolidin-1-yl 4-oxo-4-((2-((2-(3-(3,3,6,6-tetramethyl-1-oxido-4,5-didehydro-2,3,6,7-tetrahydro-1λ6-thiepin-1-ylidene)ureido)ethyl)disulfaneyl)ethyl)amino)butanoate An 8 ml screwcap vial was charged with 4-oxo-4-((2-((2-(3-(3,3,6,6-tetramethyl-1-oxido-4,5-didehydro-2,3,6,7-tetrahydro-1λ6-thiepin-1-ylidene)ureido)ethyl)disulfaneyl)ethyl)amino)butanoic acid (38.8 mg, 0.081 mmol) and dichloromethane (1 ml). N-Hydroxysuccinimide (13 mg, 0.11 mmol, 1.4 eq.) was added followed by the addition of EDC (22 mg, 0.11, 1.4 eq.). The mixture was stirred at room temperature for approximately 2 hours. The mixture was concentrated under reduced pressure and the resulting white foam was purified by preparative RP-MPLC (Reveleris Prep, LUNA-C18, 20-60% MeCN in water, 0.1% (v/v) formic acid). The product fractions were combined and lyophilised. The freeze-dried material was dissolved in dichloromethane and transferred to an 8 ml brown glass vial, the solvent was evaporated under a stream of N2 and co-evaporated with diethyl ether to afford 35 mg (76%) of the product.

LC/MS (SC_ACID) $t_R$ 1.86 min, purity 93%, mass found $[M+H]^+$ 575.

$^1$H NMR (400 MHz, Chloroform-d) δ 6.73 (s, 1H), 5.32 (t, J=6.1 Hz, 1H), 3.78 (d, J=14.1 Hz, 2H), 3.58 (q, J=6.1 Hz, 2H), 3.53-3.41 (m, 4H), 3.00 (t, J=7.1 Hz, 2H), 2.89-2.76 (m, 8H), 2.67 (t, J=7.1 Hz, 2H), 1.47 (s, 6H), 1.28 (s, 6H).

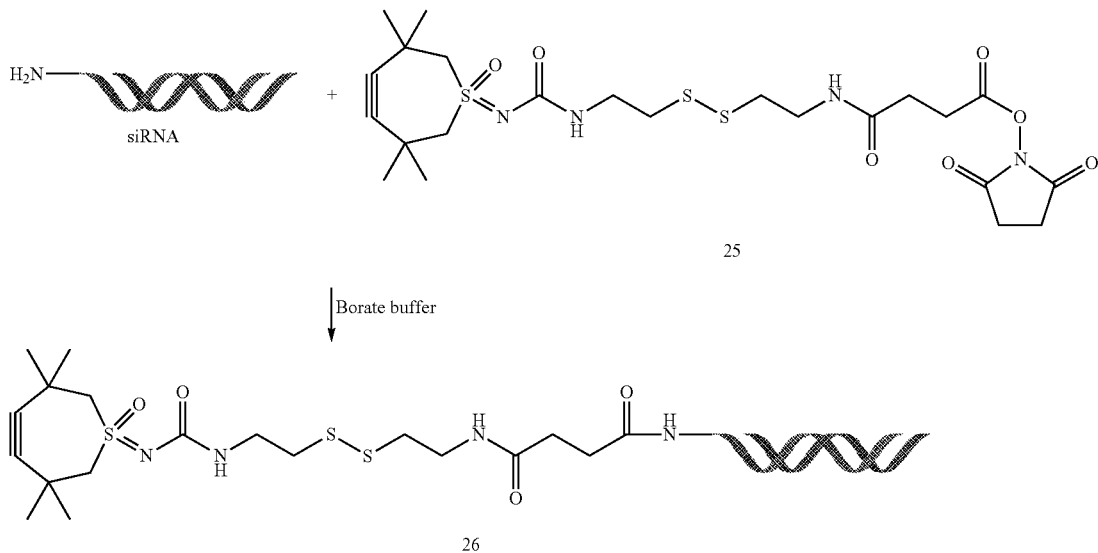

Example 25: Coupling of TMTHSI-Disulfide NHS Ester to siRNA Oligonucleotide. Preparation of TMTHSI—NH-siRNA PLK1

A 2 mL UPLC vial was charged with siRNA PLK1 oligonucleotide (5 mg, 0.36 μmol) and borate buffer pH 8.4 (250 μl) was added. A 20 mM stock solution of 2,5-dioxopyrrolidin-1-yl 4-oxo-4-((2-((2-(3-(3,3,6,6-tetramethyl-1-oxido-4,5-didehydro-2,3,6,7-tetrahydro-1λ6-thiepin-1-ylidene)ureido)ethyl)disulfaneyl)ethyl)amino)butanoate in DMSO was prepared and 5 eq., (90 μl, 1.04 mg, 1.8 μmol) of the stock solution was added to the siRNA containing solution while stirring. The mixture was stirred at room temperature and monitored by UPLC. After addition of an extra 5 eq., of 2,5-dioxopyrrolidin-1-yl 4-oxo-4-((2-((2-(3-(3,3,6,6-tetramethyl-1-oxido-4,5-didehydro-2,3,6,7-tetrahydro-1M-thiepin-1-ylidene)ureido)ethyl)disulfaneyl)ethyl)amino)butanoate (90 µl, 1.04 mg, 1.8 µmol) and additional stirring, the reaction showed >90% conversion towards TMTHSI—NH-siRNA PLK1. The final crude product was purified by PD-10 (buffer swap to phosphate buffer pH 7.4) and Vivaspin (5000 Da MWCO, 4000 g, 3 times phosphate buffer pH 7.4, final concentration step) to remove excess of TMTHSI NHS 2,5-dioxopyrrolidin-1-yl 4-oxo-4-((2-((2-(3-(3,3,6,6-tetramethyl-1-oxido-4,5-didehydro-2,3,6,7-tetrahydro-1λ6-thiepin-1-ylidene)ureido)ethyl)disulfaneyl)ethyl)amino)butanoate. The final solution of TMTHSI-NH-siRNA PLK1 (1000 µl) was transferred to a 2 mL UPLC vial and stored at +4 C.

Example 26: Coupling of Azide-CPP1 Peptide to TMTHSI-NH-siRNA Oligonucleotide. Preparation of CPP1-TMTHSI-NH-siRNA PLK1 Conjugate At first, a stock solution of azide-CPP1 peptide was prepared (0.49 mg, 0.35 µmol) in acetonitrile/water (1:1, 100 µl volume). Initially 50 µl (0.5 eq., 0.25 mg, 0.18 µmol) of the stock solution was added to the 2 mL UPLC, vial containing TMTHSI-NH-siRNA PLK1 (0.35 µmol in 1000 µl phosphate buffer pH 7.4). The mixture was stirred at room temperature and monitored by UPLC. After 30 minutes all azide-CPP1 peptide was converted and the second half of the azide-CPP1 peptide stock solution was added (0.5 eq., 0.25 mg, 0.18 µmol). After an additional 30 minutes of

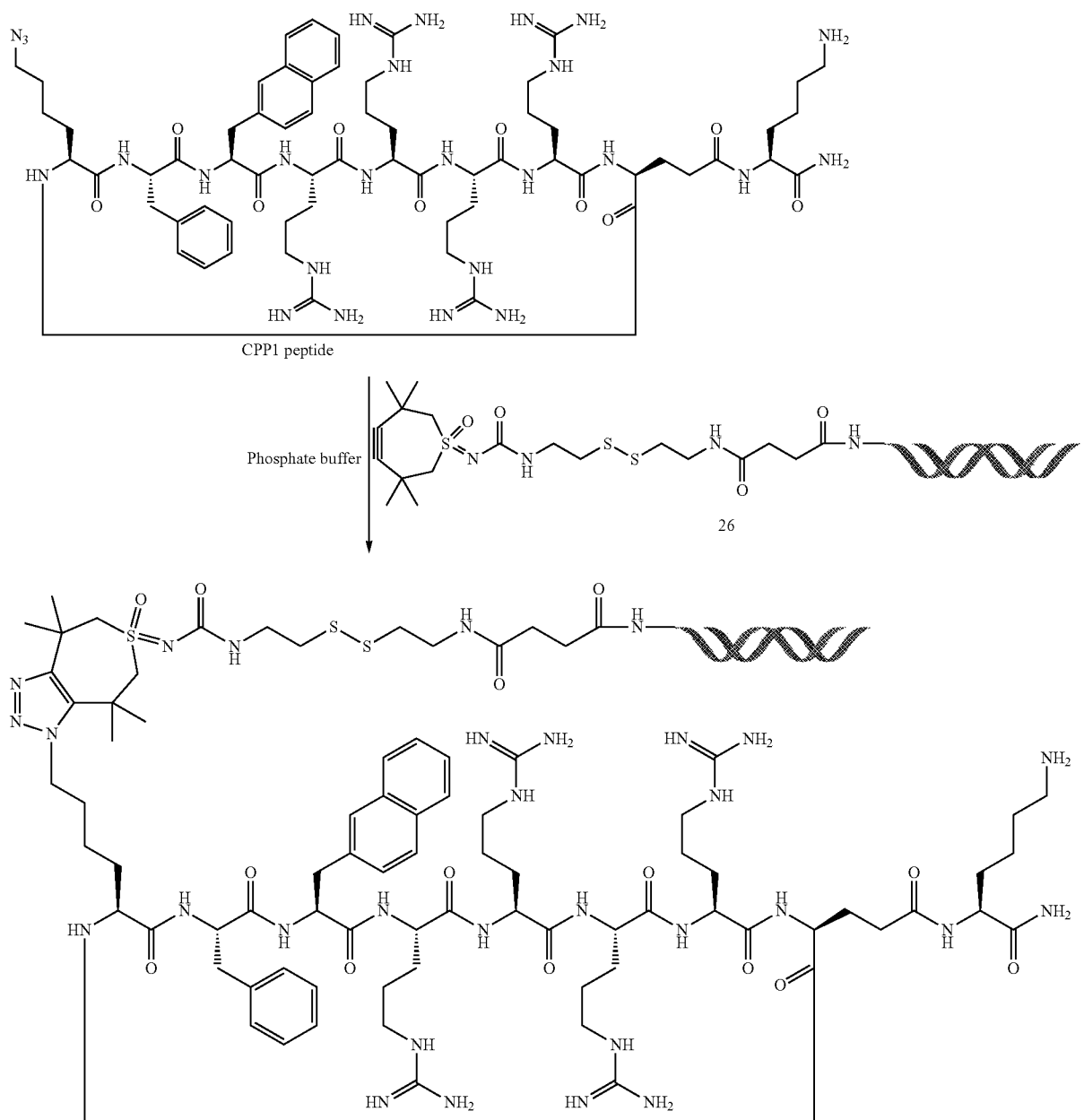

stirring the reaction towards CPP1-TMTHSI-NH-siRNA PLK1 reached full conversion. The final crude product was washed (5000 Da MWCO, 4000 g, 3 times phosphate buffer pH 7.4, final concentration step) and concentrated in a Vivaspin centrifugal tube. Final solution of CPP1-TMTHSI-NH-siRNA PLK1 (750 µl) was transferred to a 2 mL UPLC
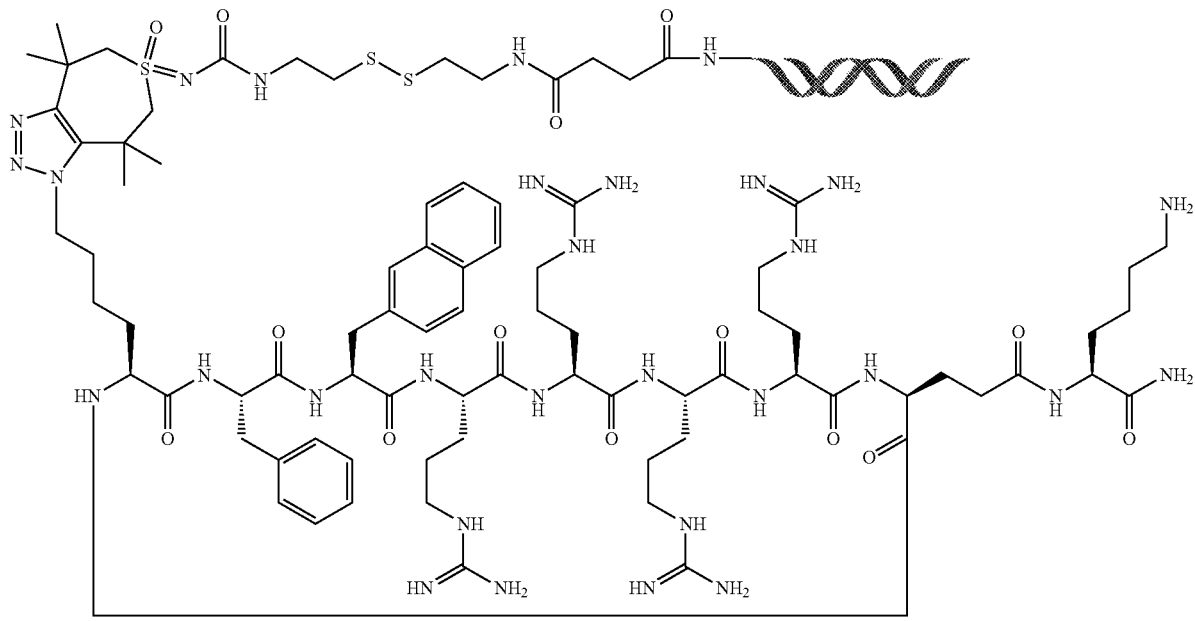
27
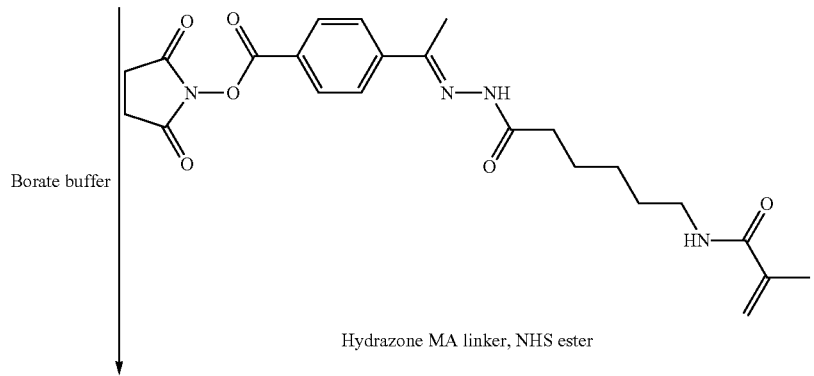
Hydrazone MA linker, NHS ester
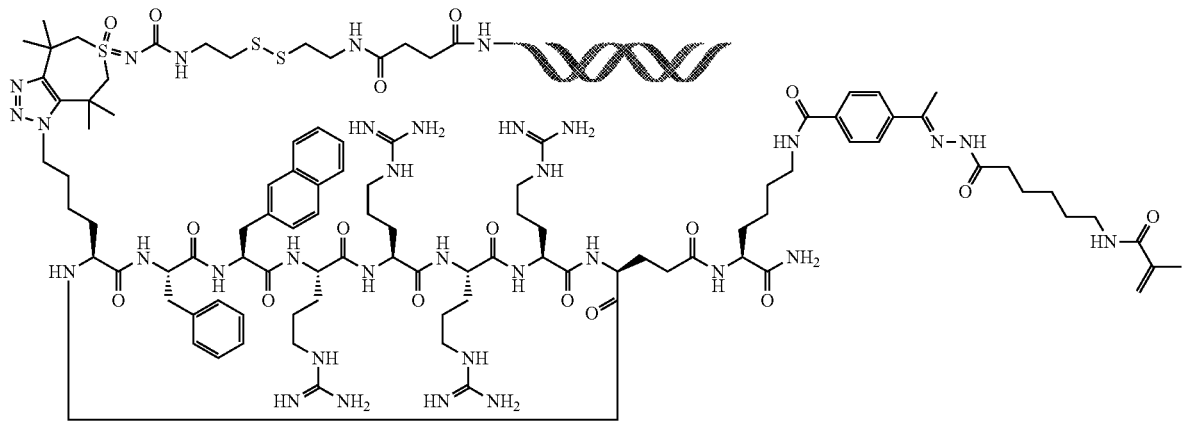
28

Example 27: Coupling of Acid Labile Linker 7 to CPP1-TMTHSI-siRNA Oligonucleotide. Preparation of Linker 7-CPP1-TMTHSI-NH-siRNA PLK1 Conjugate The solution of CPP1-TMTHSI-NH-siRNA PLK1 (750 µl) was transferred to a vivaspin centrifugal tube and buffer swapped to borate buffer pH 8.4 (5000 Da MWCO, 4000 g, 3 times borate buffer pH 8.4, final concentration step). Final volume after vivaspin: 1200 µl. A 20 mM stock solution of hydrazone MA linker NHS ester (linker 7) was prepared in DMSO. While stirring, 5 eq., of hydrazone MA linker NHS ester stock solution in DMSO (66 µl, 0.73 mg, 1.6 µmol) was added to CPP1-TMTHSI-siRNA (0.32 µmol) in borate buffer (1000 µl) at room temperature and monitored by UPLC. After 45 minutes the reaction showed full conversion to Linker 7—CPP1-TMTHSI—siRNA PLK1 conjugate. The final crude conjugate was purified by PD-10 (5000 Da MWCO, 4000 g, buffer swap to phosphate buffer pH 7.4) and Vivaspin (5000 Da MWCO cut-off, 4000 g, 3 times phosphate buffer pH 7.4, final concentration step) to remove excess of hydrazone MA linker NHS ester.

then EDC (840 mg, 4.38 mmol, 1.05 eq.) was added and the mixture was stirred at room temperature for 17 hours.

The reaction mixture was purified (in seven portions) by preparative RP-MPLC (Reveleris, XSelect 5-30% MeCN in water, 10 mM $NH_4HCO_3$, pH=9.5). The product fractions were combined and partly concentrated under reduced pressure. The resulting residue was lyophilised to afford 0.91 g (34%) of the product.

LC/MS (SC_BASE) $t_R$ 1.37 min, purity 100%, mass found $[M-H]^-$ 626.

$^1$H NMR (400 MHz, DMSO-$d_6$+$D_2O$) δ 8.66 (s, 1H), 7.99 (q, J=4.9 Hz, 1H), 7.65 (dd, J=11.6, 8.5 Hz, 2H), 6.75 (d, J=6.1 Hz, 1H), 6.67 (dd, J=9.0, 2.7 Hz, 2H), 4.52 (s, 2H), 4.33 (dd, J=8.9, 4.8 Hz, 0.4H), 4.19 (dd, J=8.1, 4.7 Hz, 0.6H), 3.45-3.31 (m, 4H), 3.26-3.13 (m, 2H), 3.11-3.01 (m, 2H), 2.26 (t, J=7.1, 6.4 Hz, 1H), 2.15 (t, J=8.0 Hz, 1H), 2.08-1.82 (m, 2H), 1.35 and 1.33 (2× s, combined 9H).

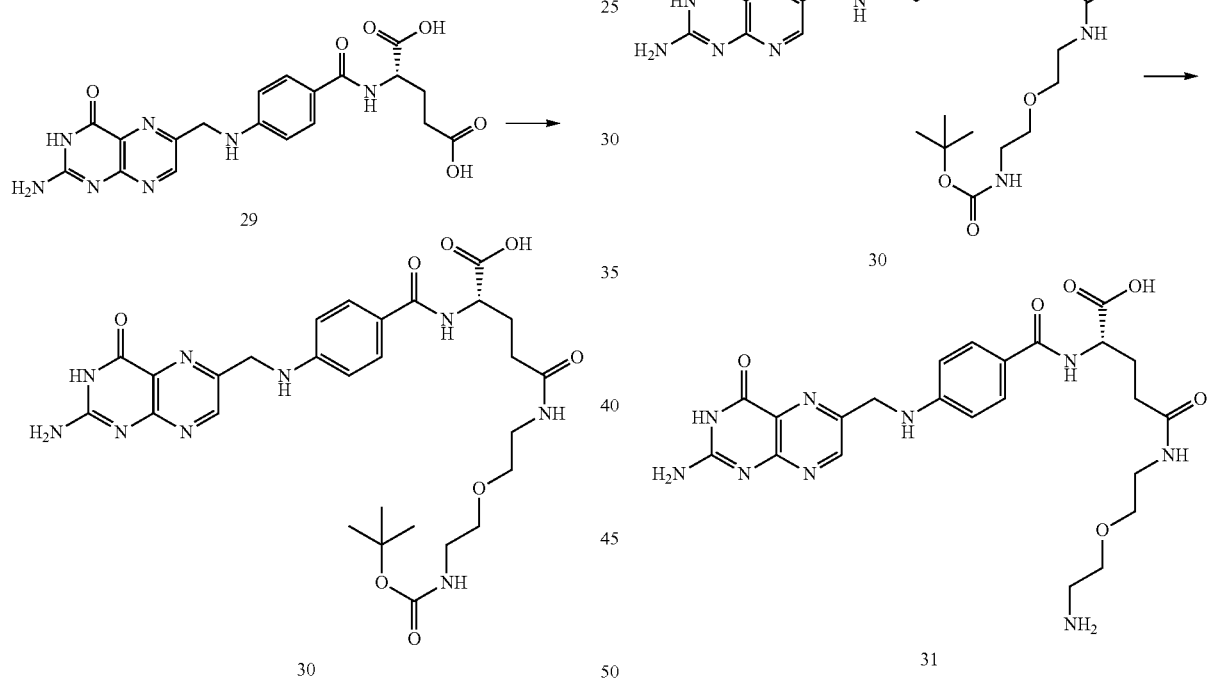

Example 29: Synthesis of (S)-15-(4-(((2-amino-4-oxo-3,4-dihydropteridin-6-yl)methyl)amino)benzamido)-2,2-dimethyl-4,12-dioxo-3,8-dioxa-5,11-diazahexadecan-16-oic Acid. (Product Isolated as a Mixture of Oily Regio Isomers)

Folic acid (1.84 g, 4.17 mmol) was suspended in anhydrous dimethyl sulfoxide (15 ml) and the flask was placed in a sand bath of 100° C. until a solution was formed. Then the solution was allowed to cool to room temperature and N-hydroxysuccinimide (503 mg, 4.37 mmol, 1.05 eq.) was added followed by a solution of N-Boc-2-(2-amino-ethoxy)-ethylamine (852 mg, 4.17 mmol) in anhydrous dimethyl sulfoxide (3 ml). The mixture was stirred for 10 minutes,

Example 30: Synthesis of $N^2$-(4-(((2-amino-4-oxo-3,4-dihydropteridin-6-yl)methyl)amino)benzoyl)-$N^5$-(2-(2-aminoethoxy)ethyl)-L-glutamine. (Product Isolated as a Mixture of α/γ Region Isomers)

(S)-15-(4-(((2-amino-4-oxo-3,4-dihydropteridin-6-yl) methyl)amino)benzamido)-2,2-dimethyl-4,12-dioxo-3,8-dioxa-5,11-diazahexadecan-16-oic acid (403 mg, 0.64 mmol) was dissolved in trifluoroacetic acid (2 ml, 26.0 mmol) and the resulting mixture was stirred at room temperature for 25 minutes. The reaction mixture was concentrated under reduced pressure, the residue was co-evaporated with dichloromethane (2×). The residue was taken up in N,N-dimethylformamide (1 ml) and warmed until fully dissolved, then allowed to cool to room temperature. The solution was treated with triethylamine (3×200 μl) to give an orange precipitate. The mixture was diluted with acetone, the solids were collected by filtration. The residue was washed with acetone (3×) and air dried to afford 346 mg (97%) of the product as an orange solid.

$^1$H NMR (400 MHz, DMSO-$d_6$) δ 8.66-8.57 (m, 1H), 8.24 (t, J=5.5 Hz, 0.6H), 8.07 (t, J=5.6 Hz, 0.4H), 7.72-7.62 (m, 1H), 7.62-7.51 (m, 1H), 7.30 (bs, 2H), 6.91 (q, J=6.1 Hz, 1H), 6.63 (t, J=7.6 Hz, 2H), 4.52-4.38 (m, 2H), 4.30 (q, J=6.3 Hz, 0.4H), 4.10 (q, J=6.4 Hz, 0.6H), 3.55 (q, J=6.2, 5.6 Hz, 3H), 3.43 (bs, 3H), 3.31-3.13 (m, 4H), 2.94 (q, J=6.2, 5.8 Hz, 2H), 2.21-2.11 (m, 2H), 2.06-1.79 (m, 3H), 0.97 (t, J=7.2 Hz, 1H.

NMR shows very broad HOD signal underneath signals between 4.5 and 2.5 ppm.

Example 31: Synthesis of N$^2$-(4-(((2-amino-4-oxo-3,4-dihydropteridin-6-yl)methyl)amino)benzoyl)-N$^5$-(2-(2-(3-(3,3,6,6-tetramethyl-1-oxido-4,5-didehydro-2,3,6,7-tetrahydro-1λ$^6$-thiepin-1-ylidene)ureido) ethoxy)ethyl)-L-glutamine. (Product Isolated as a Mixture of α/γ Regio Isomers)

N$^2$-(4-(((2-amino-4-oxo-3,4-dihydropteridin-6-yl) methyl)amino)benzoyl)-N$^5$-(2-(2-amino ethoxy)ethyl)-L-glutamine (90.3 mg, 0.13 mmol) was dissolved in hot dimethyl sulfoxide (1.5 ml) and allowed to cool to room temperature. Triethylamine (107 μl, 0.77 mmol, 6 eq.) was added and the resulting mixture was added to 2,5-dioxopyrrolidin-1-yl (3,3,6,6-tetramethyl-1-oxido-4,5-didehydro-2,3,6,7-tetrahydro-1λ$^6$-thiepan-1-ylidene)carbamate (52 mg, 0.15 mmol, 1.2 eq.). The reaction mixture was stirred at room temperature for 4 days.

The reaction mixture was purified by preparative RP-MPLC (Reveleris, XSelect 5-40% MeCN in water, 10 mM NH$_4$HCO$_3$, pH=9.5). The product fractions were combined and lyophilised to afford 51 mg (53%) of the product.

LC/MS (SC_BASE) $t_R$ 1.45 min, purity 99%, mass found [M+H]$^+$ 753.

$^1$H NMR (400 MHz, DMSO-$d_6$+D$_2$O) δ 8.66 (s, 1H), 8.02-7.90 (m, 1H), 7.70-7.59 (m, 2H), 6.72-6.61 (m, 3H), 4.50 (s, 2H), 4.37-4.32 (in, 0.4H), 4.22-4.13 (m, 0.6H), 3.90-3.79 (m, 2H), 3.59 (dd, J=14.0, 4.5 Hz, 2H), 3.44-3.30 (m, 5H), 3.25-3.14 (m, 2H), 3.09 (t, J=5.8 Hz, 2H), 2.26 (t, J=7.7 Hz, 1H), 2.15 (t, J=7.6 Hz, 1H), 2.05-1.93 (m, 1H), 1.90 (d, J=13.5 Hz, 1H), 1.33 (s, 6H), 1.19 (s, 6H).

Example 32: Coupling of TMTHSI-Containing Linker Folic Acid to an Azide Containing Nanoparticle (CriPec)

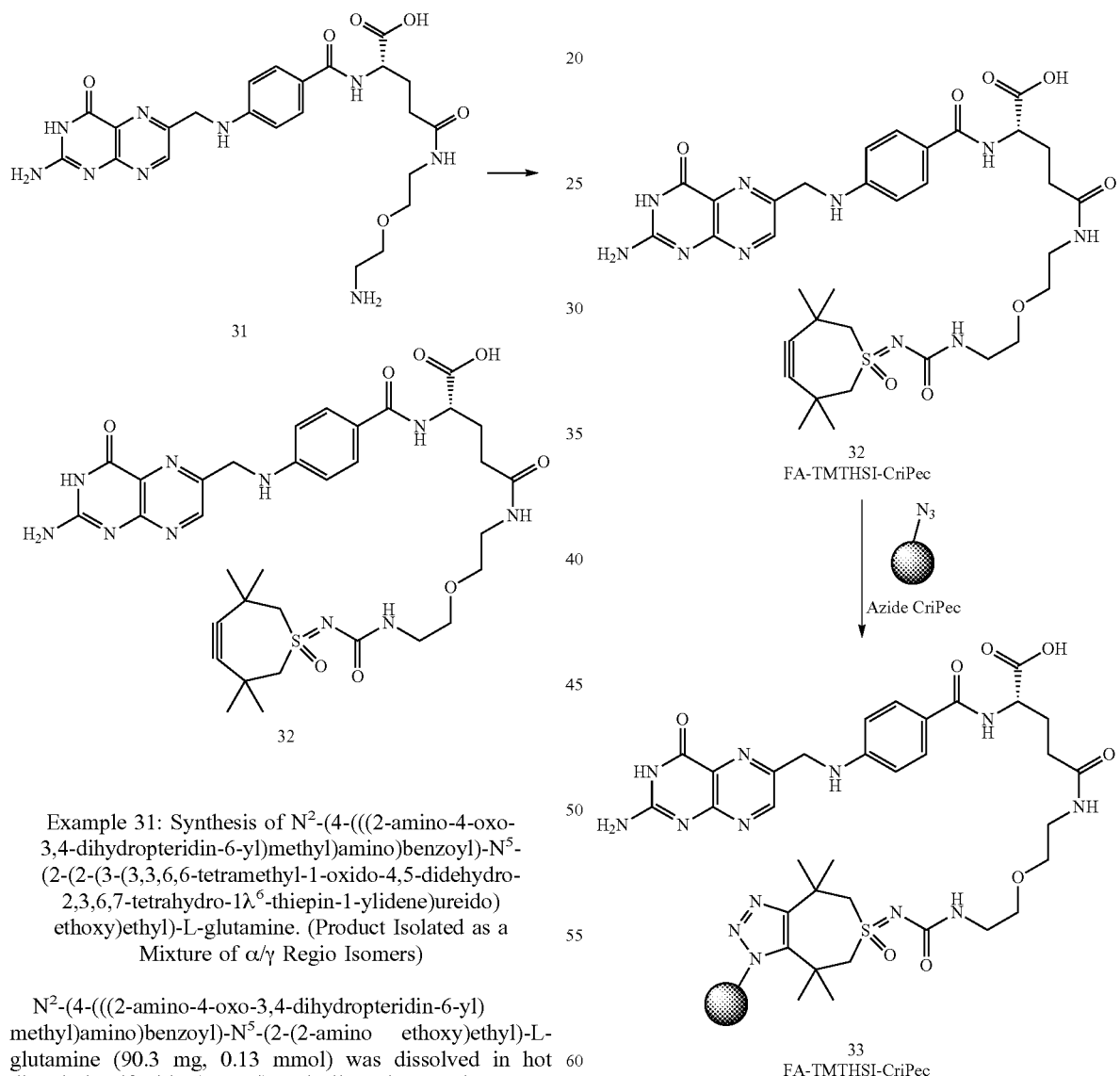

Folic acid-labelled core-crosslinked polymeric micelles were generated by conjugating Folic acid to the surface of the polymeric micelles shell and used for targeting studies. To allow for Folic acid conjugation via click chemistry, azide functionalized polymeric micelles were manufactured essentially following the reported protocol [Hu et al. Biomaterials. 2015; 53:370-8], except that a fraction of azide-functionalized block copolymer (22 kDa, derivatized with 10 mol % crosslinker L2 [1], 5 w % of total block copolymer) was added next to the (95 w %) non-functionalized block copolymer (22 kDa, derivatized with 10 mol % crosslinker L2 [Biomaterials. 2015; 53:370-8],], 95 w % of total block copolymer). These two block copolymers were synthesized following the same procedures, except that for the former (azide-PEG$_{5000}$))$_2$-ABCPA initiator synthesized from azide-PEG$_{5000}$-OH was used instead. The obtained azide-functionalized polymeric micelles were then purified in 20 mM ammonium acetate pH 5 buffer containing 130 mM NaCl, buffer swapped to 20 mM sodium phosphate pH 7.4 buffer containing 130 mM NaCl and concentrated to approx. 96 mg/mL polymer equiv. using Tangential Flow Filtration (TFF) equipped with a modified Polyethersulfone (mPES) 100 kDa module (Spectrumlabs). Next, Folic acid was conjugated to the concentrated azide-functionalized core-crosslinked polymeric micelles via copper-free click chemistry using the following approach:

At RT, DMSO (93 μL) was added to 200 μL of azide-functionalized modified core-crosslinked polymeric micelles (0.13 μmol azide equiv.) while stirring (300 rpm) in an amber UPLC vial. Upon dissipation of heat, Folic acid (1.0 eq., 0.13 μmol, 5 μL, Mercachem) was added dropwise to the reaction mixture. The progress of the conjugation reaction was monitored by UPLC-UV for 4 hours after which the reaction was stopped. Based on UPLC, conversion of Folic Acid was determined to be 45%, which translates to 2.3% Folic acid labelled core-crosslinked polymeric micelles.

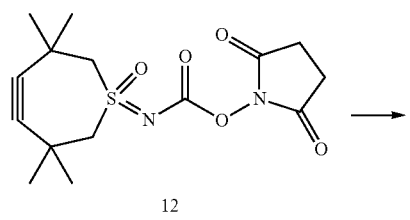

12

Example 33: Synthesis of 1-(2-(2-(2-aminoethoxy)ethoxy)ethyl)-3-(3,3,6,6-tetramethyl-1-oxido-4,5-didehydro-2,3,6,7-tetrahydro-1λ$^6$-thiepin-1-ylidene) urea

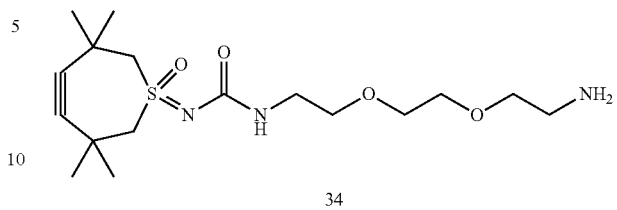

34

Under N$_2$-atmosphere, 2,5-dioxopyrrolidin-1-yl (3,3,6,6-tetramethyl-1-oxido-4,5-didehydro-2,3,6,7-tetrahydro-1λ$^6$-thiepan-1-ylidene)carbamate (197 mg, 0.58 mmol) was dissolved in dichloromethane (12.5 ml) and 2,2'-(ethane-1,2-diylbis(oxy))bis(ethan-1-amine) (0.42 ml, 2.89 mmol, 5 eq.) was added. The reaction was stirred at room temperature for 2 hours. The reaction mixture was concentrated under reduced pressure. The residue was taken up in a 1:1 mixture of acetonitrile/water (4 ml) and purified (in two portions) by preparative RP-MPLC (Reveleris, XSelect 10-50% MeCN in water, 10 mM NH$_4$HCO$_8$, pH=9.5). The product fractions were combined and lyophilised to afford 156 mg (72%) of the product as a white fluffy solid.

LC/MS (SC_BASE) t$_R$ 1.67 min, purity 99%, mass found [M+H]$^+$ 374.

$^1$H NMR (400 MHz, DMSO-d$_6$+D$_2$O) δ 3.86 (d, J=14.0 Hz, 2H), 3.61 (d, J=13.9 Hz, 2H), 3.54-3.46 (m, 4H), 3.40 (q, J=6.0 Hz, 4H), 3.15-3.04 (m, 3H), 2.67 (t, J=5.7 Hz, 1H), 1.34 (s, 6H), 1.21 (s, 6H).

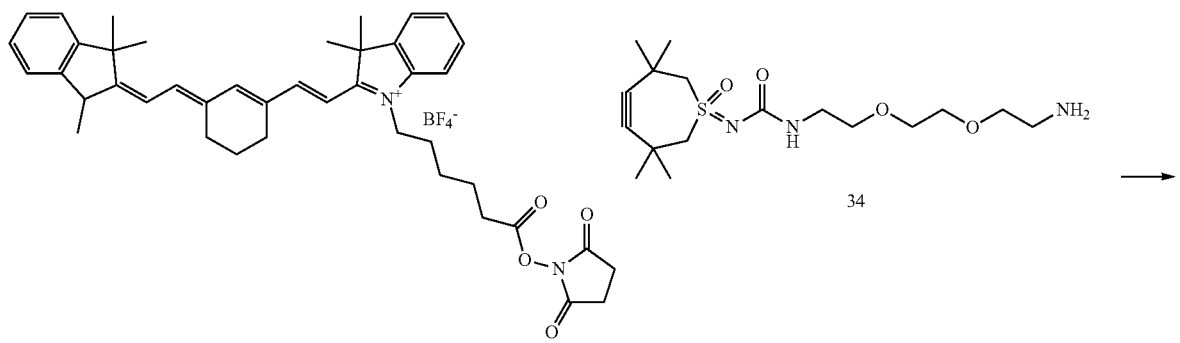

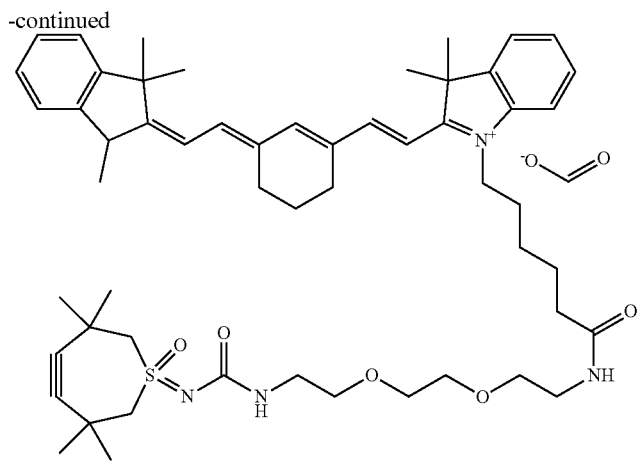

Example 34: Synthesis of 1-(2-(2-(2-aminoethoxy)ethoxy)ethyl)-3-(3,3,6,6-tetramethyl-1-oxido-4,5-didehydro-2,3,6,7-tetrahydro-1λ⁶-thiepin-1-ylidene)urea-Cy7 Adduct Formate Salt An 8 ml screwcap vial was charged with Cy7-NHS ester (95 mg, 0.13 mol) and MeCN (1.5 ml), a solution of 1-(2-(2-(2-aminoethoxy)ethoxy)ethyl)-3-(3,3,6,6-tetramethyl-1-oxido-4,5-didehydro-2,3,6,7-tetrahydro-1λ⁶-thiepin-1-ylidene)urea (66.5 mg, 0.18 mmol, 1.37 eq.) in MeCN (1.5 ml) was added and the mixture was stirred at room temperature for 2 hours. Then the mixture was stored at −20° C. overnight. The mixture was allowed to warm to room temperature, then purified by preparative MPLC (Reveleris Prep, LUNA-C18, 20-60% MeCN in water, 0.1% (v/v) formic acid), the product fractions were concentrated under reduced pressure and the residue was diluted with a little of MeCN and lyophilised overnight to afford 95 mg (77%) of the product as a dark green solid.

LC/MS (AN_ACID_DAY_UV800) $t_R$ 3.46 min, purity 88%, mass found $[M]^+$ 905, $[M+H]^{2+}$ 453.

$^1$H NMR (400 MHz, Methanol-$d_4$) δ 8.37 (s, 1H), 8.02-7.95 (m, 0.5H), 7.75 (dd, J=14.0, 8.5 Hz, 1.5H), 7.47 (d, J=7.5 Hz, 2H), 7.43-7.34 (m, 1H), 7.31-7.20 (m, 3H), 7.15-6.92 (m, 1H), 6.81-6.34 (m, 2H), 6.24-6.09 (m, 1H), 4.11 (t, J=7.3 Hz, 1H), 3.86 (d, J=14.1 Hz, 2H), 3.66-3.55 (m, 8H), 3.55-3.45 (m, 5H), 3.39-3.32 (m, 3H), 3.29-3.21 (m, 2H), 2.57 (q, J=5.6 Hz, 3H), 2.50-2.28 (m, 1H), 2.27-2.15 (m, 2H), 2.00-1.89 (m, 2H), 1.89-1.74 (m, 3H), 1.75-1.61 (m, 10H), 1.59-1.52 (m, 2H), 1.51-1.42 (m, 2H), 1.40 (s, 7H), 1.33-1.20 (m, 8H), 1.03 (s, 1H).

Method: AN_ACID_DAY_UV800, Apparatus: Agilent 1260 Bin. Pump: G1312B, degasser; autosampler, ColCom, DAD: Agilent G1315D, 210-800 nm, MSD: Agilent LC/MSD G6130B ESI, pos/neg 100-1000, ELSD Alltech 3300 gas flow 1.5 ml/min, gas temp: 40° C.; column: Waters XSelect™ C18, 50×2.1 mm, 3.5 g, Temp: 35° C., Flow: 0.8 mL/min, Gradient: $t_0$=5% A, $t_{3.5\ min}$=98% A, $t_{6\ min}$=98% A, Post time: 2 min; Eluent A: 0.1% formic acid in acetonitrile, Eluent B: 0.1% formic acid in water).

MS Parameters

Source: ESI, Capillary voltage: 3000V, Drying gas flow: 12 L/min, Nebulizer Pressure 60 psig, Drying Gas Temp: 350° C., Fragmentor 70, MS scan: MS range 100-1000 (positive and negative mode), scan speed: 0.84 sec/cycle.

Example 35: Reaction Kinetics of TMTHSI with Benzyl Azide to Determine Reaction Rate Constant Value kt The kt value for the conversion of benzylazide with BCN-OH and TMTHSI was investigated by monitoring the reactions via mass spectrometry. In this study, QTOF mass spectrometry with an ESI source coupled to it, was utilized as a method of measurements. In detail, the alkyne (TMTSHI or BCN-OH in ACN/water/acetic acid (3:1:0.01%) was reacted with 1.0 eq benzylazide and reaction kinetics were measured using MS. The results of the measurements are included in FIG. 55. The measured kt value for TMTHSI in the reaction with benzylazide is 0.83 $M^{-1}S^{-1}$, which is approximately 7 times faster than BCN-OH (0.12 $M^{-1}S^{-1}$).

CITED LITERATURE

A. Krebs and H. Kimling, Tetrahedron Lett., 1970, 761-764.
de Almeida, Sletten, E. M., Nakamura, H., Palaniappan E. K., Bertozzi, C. R., Augew. Chem. Int. Ed., 2012, 51, 2443-2447
Li et al. Molecules, 2016, 21, 1393.
Tota, A., Zenzola, M., Chawner, S. J., St John-Campbell, S., Carlucci, C. Romanazzi, G., Degennaro, L., Bull, J. A., Luisi, R., Chem. Commun., 2017, 53, 348-351.
Hu et al. Biomaterials. 2015; 53:370-8
King et al, Chem Comm, 2012, 48, 9308-9309.
Dommerholt et al. Nature Communications 5, Article number: 5378 (2014)
Dommerholt et al. Top Curr Chem (Z) 2016, 374:16

The invention claimed is:

1. A compound of Formula (I)

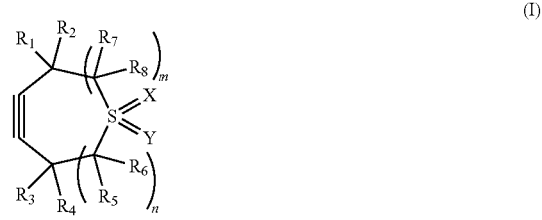

wherein:

n and m are independently 0, 1, or 2 and n+m is 2;

X is O or $NR^9$,

Y is $NR^{10}$, $R^1$, $R^2$, $R^3$, $R^4$ are independently selected from the group consisting of hydrogen, halogen O, N, P, S, $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups and $C_7$-$C_{24}$ heteroarylalkyl groups, wherein the O, N, P, and S are -further independently coupled to hydrogen, halogen, $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, the $C_1$-$C_{12}$ alkyl groups optionally being interrupted by one of more hetero-atoms selected from the group consisting of O, N, P and S, wherein the $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups and $C_7$-$C_{24}$ heteroarylalkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups are optionally substituted, the $C_1$-$C_{12}$ alkyl groups, the $C_1$-$C_{12}$ alkoxy groups, the $C_3$-$C_{12}$ cycloalkyl groups and the $C_3$-$C_{12}$ cycloalkoxy groups are optionally interrupted by one of more hetero-atoms selected from the group consisting of O, N, P and S, wherein the silyl groups are represented by the formula $(R^{11})_3Si-$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups are optionally substituted, the $C_1$-$C_{12}$ alkyl groups, the $C_1$-$C_{12}$ alkoxy groups, the $C_3$-$C_{12}$ cycloalkyl groups and the $C_3$-$C_{12}$ cycloalkoxy groups being optionally interrupted by one of more hetero-atoms selected from the group consisting of O, N, P and S;

$R^5$, $R^6$, $R^7$, $R^8$ are independently selected from the group consisting of hydrogen, halogen, O, N, P, S, $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups and $C_7$-$C_{24}$ heteroarylalkyl groups, wherein the O, N, P, and S are further independently coupled to hydrogen, halogen, $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, the $C_1$-$C_{12}$ alkyl groups optionally being interrupted by one of more hetero-atoms selected from the group consisting of O, N, P and S, wherein the $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups and $C_7$-$C_{24}$ heteroarylalkyl groups are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups are optionally substituted, the $C_1$-$C_{12}$ alkyl groups, the $C_1$-$C_{12}$ alkoxy groups, the $C_3$-$C_{12}$ cycloalkyl groups and the $C_3$-$C_{12}$ cycloalkoxy groups being optionally interrupted by one of more hetero-atoms selected from the group consisting of O, N, P and S, wherein the silyl groups are represented by the formula $(R^{11})_3Si-$, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups are optionally substituted, the $C_1$-$C_{12}$ alkyl groups, the $C_1$-$C_{12}$ alkoxy groups, the $C_3$-$C_{12}$ cycloalkyl groups and the $C_3$-$C_{12}$ cycloalkoxy groups being optionally interrupted by one of more hetero-atoms selected from the group consisting of O, N, P and S;

wherein, optionally, R1 and R7, R1 with R8, R2 with R7, R2 with R8, R3 with R5, R3 with R6, R4 with R5-, and/or R4 with R6 independently form fused ring systems;

$R^9$, $R^{10}$ are independently selected from the group consisting of hydrogen, halogen, $R^{12}$, $-CH=C(R^{12})_2$, $-C\equiv CR^{12}$, $-[C(R^{12})_2C(R^{12})_2O]_q-R^{12}$, wherein q is in the range of 1 to 200, $-CN$, $-N_3$, $-NCX$, $-XCN$, $-XR^{12}$, $-N(R^{12})_2$, $-^+N(R^{12})_3$, $-C(X)N(R^{12})_2$, $-C(R^{12})_2XR^{12}$, $-C(X)R^{12}$, $-C(X)XR^{12}$, $-S(O)R^{12}$, $-S(O)_2R^{12}$, $-S(O)OR^{12}$, $-S(O)_2OR^{12}$, $-S(O)N(R^{12})_2$, $-S(O)_2N(R^{12})_2$, $-OS(O)R^{12}$, $-OS(O)_2R^{12}$, $-OS(O)OR^{12}$, $-OS(O)_2OR^{12}$, $-P(O)(R^{12})(OR^{12})$, $-P(O)(OR^{12})_2$, $-OP(O)(OR^{12})_2$, $-Si(R^{12})_3$, $-XC(X)R^{12}$, $-XC(X)XR^{12}$, $-XC(X)N(R^{12})_2$, $-N(R^{12})C(X)R^{12}$, $-N(R^{12})C(X)XR^{12}$ and $-N(R^{12})C(X)N(R^{12})_2$, wherein X is oxygen or sulphur and wherein $R_{12}$ is independently selected from the group consisting of hydrogen, halogen, $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups and $C_7$-$C_{24}$ heteroarylalkyl groups.

2. The compound according to claim 1, wherein n is 1 and m is 1 and the compound is of Formula (II)

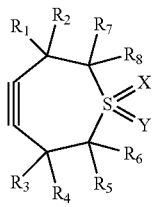

(II)

and $R^1$-$R^8$, X, Y are as defined in claim 1.

3. The compound according to claim 1, wherein X is O, and/or $R^{10}$ is H.

4. The compound according to claim 1, wherein $R^1$, $R^2$, $R^3$, $R^4$, $R^5$, $R^6$, $R^7$, $R^8$ are independently H, halogen or $C_1$-$C_{24}$ alkyl.

5. The compound according to claim 4, wherein:
$R^1$, $R^2$, $R^3$, $R^4$, $R^5$, $R^6$, $R^7$, $R^8$ are methyl, or
$R^1$, $R^2$, $R^3$, $R^4$ are methyl and $R^5$, $R^6$, $R^7$, $R^8$ are H.

6. A compound of Formula (III)

(Formula I)-L-Q      (III)

wherein Formula I is as defined in claim 1, whereby X and/or Y and/or one of the atoms in the ring adjacent to the S atom of the compound of Formula (I), independently, are coupled to an optional linking group (L) and a functional group (Q) to yield the compound of Formula (III):
wherein
the linking group (L) is absent or selected from linear or branched $C_1$-$C_{24}$ alkylene groups, $C_2$-$C_{24}$ alkenylene groups, $C_2$-$C_{24}$ alkynylene groups, $C_3$-$C_{24}$ cycloalkylene groups, $C_5$-$C_{24}$ cycloalkenylene groups, $C_5$-$C_{24}$ cycloalkynylene groups, $C_7$-$C_{24}$ alkylarylene groups, $C_7$-$C_{24}$ alkylheteroarylene groups, $C_7$-$C_{24}$ arylalkylene groups, $C_7$-$C_{24}$ heteroarylalkylene groups, $C_5$-$C_{24}$ arylalkenylene groups, $C_5$-$C_{24}$ heteroarylalkenylene groups, $C_9$-$C_{24}$ arylalkynylene groups, and $C_9$-$C_{24}$ heteroarylalkynylene groups, the alkylene groups, alkenylene groups, alkynylene groups, cycloalkylene groups, cycloalkenylene groups, cycloalkynylene groups, alkylarylene groups, alkylheteroarylene groups, arylalkylene groups, heteroarylalkylene groups, arylalkenylene groups, heteroarylalkenylene groups, arylalkynylene groups and heteroarylalkynylene groups optionally being substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_5$-$C_{12}$ cycloalkenyl groups, $C_5$-$C_{12}$ cycloalkynyl groups, $C_8$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens (F, CL, Br, I), amino groups, oxo and silyl groups, wherein the silyl groups can be represented by the formula $(R^{11})_3Si$—, wherein $R^{11}$ is defined as above, or L is a chain with a length of 1-25 atoms, and comprises one or more moieties independently selected from the group consisting of —S(O)$_2$—, —S—, —S—S—, —C(O)NH—, —NHC(O)—, —C(O)O— and phenylene, whereby said chain length is determined by the number of atoms in the longest linear chain of atoms, whereby said longest linear chain may comprise one or more further heteroatoms; and
Q is selected from the group consisting of —OR$^{12}$, —N(R$^{12}$)$_2$, —N(R$^{12}$)$_3$, —C(O)N(R$^{12}$)$_2$, —C(O)OR$^{12}$, —OC(O)R$^{12}$, —OC(O)OR$^{12}$, —OC(O)N(R$^{12}$)$_2$, —N(R$^{12}$)C(O)R$^{12}$, —N(R$^{12}$)C(O)OR$^{12}$ and —N(R$^{12}$)C(O)N(R$^{12}$)$_2$, wherein $R^{12}$ is independently selected from the group consisting of hydrogen, halogen, $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups, and $C_7$-$C_{24}$ heteroarylalkyl groups, or Q comprises an alcohol, amine, thiol, carboxylic ester, carboxylic acid or an activated ester, ketone, aldehyde, nitrile, maleimide, alkene, alkyne, heteroaromate, leaving group or phosphoramidite.

7. The compound according to claim 6, wherein L is absent or a —[C(R$^{12}$)$_2$C(R$^{12}$)$_2$O]$_q$—R$^{12}$, wherein q is in the range of 1 to 200, —CN, —NCX, —XCN, —XR$^{12}$, —N(R$^{12}$)$_2$, —$^+$N(R$^{12}$)$_3$, —C(X)N(R$^{12}$)$_2$, —C(R$^{12}$)$_2$XR$^{12}$, —C(X)R$^{12}$, —C(X)XR$^{12}$, —S(O)R$^{12}$, —S(O)$_2$R$^{12}$, —S(O)OR$^{12}$, —S(O)$_2$OR$^{12}$, —S(O)N(R$^{12}$)$_2$, —S(O)$_2$N(R$^{12}$)$_2$, —OS(O)R$^{12}$, —OS(O)$_2$R$^{12}$, —OS(O)OR$^{12}$, —OS(O)$_2$OR$^{12}$, —P(O)(R$^{12}$)(OR$^{12}$), —P(O)(OR$^{12}$)$_2$, —OP(O)(OR$^{12}$)$_2$, —Si(R$^{12}$)$_3$, —XC(X)R$^{12}$, —XC(X)XR$^{12}$, —XC(X)N(R$^{12}$)$_2$, —N(R$^{12}$)C(X)R$^{12}$, —N(R$^{12}$)C(X)XR$^{12}$ and —N(R$^{12}$)C(X)N(R$^{12}$)$_2$, wherein X is oxygen or sulphur and wherein $R^{12}$ is as defined in claim 6, and/or
wherein Q is selected from the group consisting of —OR$^{12}$, —N(R$^{12}$)$_2$, —N(R$^{12}$)$_3$, —C(O)N(R$^{12}$)$_2$, —C(O)OR$^{12}$, —OC(O)R$^{12}$, —OC(O)OR$^{12}$, —OC(O)N(R$^{12}$)$_2$, —N(R$^{12}$)C(O)R$^{12}$, —N(R$^{12}$)C(O)OR$^{12}$ and —N(R$^{12}$)C(O)N(R$^{12}$)$_2$, wherein $R^{12}$ is as defined in claim 6.

8. The compound according to claim 6 wherein the functional group Q is coupled to one or more of a drug, an antibody, a protein, a peptide, an oligonucleotide, a ligand, a imaging label, a targeting ligand, a delivery agent, a nanoparticle, a carrier compound.

9. The compound according to claim 6, composed of a compound of formula (I) coupled to an optional linking group (L) and a functional group (Q), to yield a compound of Formula (III):

(Formula I)-L-Q      (III)

wherein
formula (I) is coupled to optional linking group (L) and functional group (Q) at atom Y,
m and n are both 1,
X is O,
$R^1$, $R^2$, $R^3$, $R^4$ are identical and selected from the group consisting of H and $C_1$-$C_4$ alkyl,
$R^5$, $R^6$, $R^7$, $R^8$ are identical and selected from the group consisting of H and $C_1$-$C_4$ alkyl,
Y is NR$^{10}$, whereby $R^{10}$ is replaced by L-Q,
L is absent or is a chain with a length of 1-25 atoms and comprises one or more moieties independently selected from the group consisting of —S(O)$_2$—, —S—, —S—S—, —C(O)NH—, —NHC(O)—, —C(O)O— and phenylene, whereby said chain length is determined by the number of atoms in the in the longest linear chain of atoms, and whereby said longest linear chain may comprise one or more further heteroatoms, and Q comprises an alcohol, amine, thiol, carboxylic ester, carboxylic acid or an activated ester, ketone, aldehyde, nitrile, maleimide, alkene, alkyne, heteroaromate, leaving group and phosphoramidite.

10. A compound comprising the compound according to claim 9, coupled to a molecule of interest via functional group Q wherein the molecule of interest is selected from the group consisting of a drug, an antibody, a protein, a peptide, an oligonucleotide, a ligand, an imaging label, a targeting ligand, a delivery agent, a nanoparticle and a carrier compound.

11. A compound comprising the compound according to claim 10 coupled to a compound comprising a 1,3-dipole, a 1,3-diene or a 1,3-heterodiene, wherein the alkyne group of the compound of Formula (I) is coupled to the compound comprising a 1,3-dipole, a 1,3-diene or a 1,3-heterodiene.

12. A method for coupling the compound as defined in claim 10 with a compound comprising a 1,3-dipole, a 1,3-diene or a 1,3-heterodiene, comprising a step of coupling the compound as defined in claim 10 with a compound comprising a 1,3-dipole, a 1,3-diene or a 1,3-heterodiene.

13. A method for the preparation of a nanoparticle coupled to an active compound selected from the group of a drug, an antibody, a protein, a peptide, an oligonucleotide, a ligand, an imaging label, a targeting ligand, a delivery agent, a nanoparticle, and a carrier compound, the method comprising coupling of the compound as defined in claim 6 with an azide-containing compound to form a triazole compound, wherein:

1) the nanoparticle is the azide-containing compound and the active compound comprises the compound as defined in claim 6, whereby the active compound is coupled to functional group Q in the compound as defined in claim 6, and wherein the alkyne group of the compound as defined in claim 6 is coupled to the azide, or 2) the nanoparticle comprises the compound as defined in claim 6 and the active compound comprises the azide-containing compound, whereby the nanoparticle is coupled to functional group Q in the compound as defined in claim 6, and wherein the alkyne group of the compound of Formula (III) is coupled to the azide.

14. A method for the preparation of the compound of Formula (I) according to claim 1 wherein X is O and Y is NH, m and n are both 1, $R^1$-$R^4$ are methyl and $R^5$-$R^8$ are hydrogen, the method comprising the steps of:

a. converting a bishydrazone (2) to an iminodidehydrosulfonimino (3)

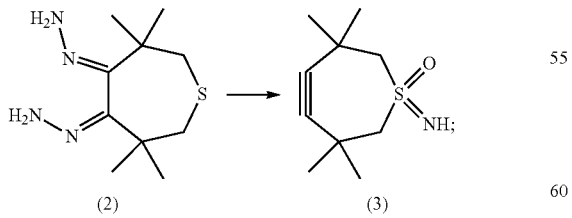

(2)     (3)

b. isolating the resulting iminodidehydrosulfonimino (3).

15. The method according to claim 14, wherein the conversion comprises an oxidation reaction wherein the bishydrazone (2) is reacted with an oxidant to oxidise the sulfur functionality to the sulfonimino functionality and wherein the conversion further comprises an oxidation reaction wherein the bishydrazone (2) is reacted with an oxidant to oxidise the hydrazone functionality to the alkyne functionality.

16. A method for coupling two molecules of interest comprising coupling said two molecules via the compound as defined in claim 6, wherein one of the two molecules is coupled to functional group Q of the compound as defined in claim 6 and one of the two molecules is coupled to the alkyne group of the compound as defined in claim 6 and wherein optionally, the molecules are independently selected from amongst a drug, an antibody, a protein, a peptide, an oligonucleotide, a ligand, a imaging label, a targeting ligand, a delivery agent, a nanoparticle, and a carrier compound.

17. The method according to claim 16, wherein said method comprises a bioorthogonal, optional copper-free, click reaction.

18. The method according to claim 16, wherein one of the two molecules of interest is a nanoparticle and one of the two molecule of interest is a drug, an antibody, a protein, a peptide, an oligonucleotide, a ligand, a imaging label, a targeting ligand, a delivery agent, a nanoparticle, and a carrier compound and wherein the coupling comprises a copper free click reaction.

19. The compound according to claim 1, wherein the fused ring systems are selected from the group consisting of cycloalkyl, cycloaryl, cycloheteraryl, cycloalkylaryl, cycloalkylheteroaryl, cycloarylalkyl, cycloheteroarylalkyl systems, wherein the cycloalkyl groups of the fused ring systems optionally are interrupted by one or more hetero-atoms selected from the group consisting of O, N, P and S, wherein the cycloalkyl, cycloaryl, cycloheteraryl, cycloalkylaryl, cycloalkylheteroaryl, cycloarylalkyl, cycloheteroarylalkyl systems of the fused systems are independently optionally substituted with one or more substituents independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups, halogens, amino groups, oxo groups and silyl groups, wherein the $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups, $C_3$-$C_{12}$ cycloalkyloxy groups are optionally substituted, the $C_1$-$C_{12}$ alkyl groups, the $C_1$-$C_{12}$ alkoxy groups, the $C_3$-$C_{12}$ cycloalkyl groups and the $C_3$-$C_{12}$ cycloalkoxy groups being optionally interrupted by one of more hetero-atoms selected from the group consisting of O, N, P and S, wherein the silyl groups are represented by the formula $(R^{11})_3Si$—, wherein $R^{11}$ is independently selected from the group consisting of $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups, wherein the $C_1$-$C_{12}$ alkyl groups, $C_2$-$C_{12}$ alkenyl groups, $C_2$-$C_{12}$ alkynyl groups, $C_3$-$C_{12}$ cycloalkyl groups, $C_1$-$C_{12}$ alkoxy groups, $C_2$-$C_{12}$ alkenyloxy groups, $C_2$-$C_{12}$ alkynyloxy groups and $C_3$-$C_{12}$ cycloalkyloxy groups are optionally substituted, the $C_1$-$C_{12}$ alkyl groups, the $C_1$-$C_{12}$ alkoxy groups, the $C_3$-$C_{12}$ cycloalkyl groups and the $C_3$-$C_{12}$ cycloalkoxy groups being optionally interrupted by one of more hetero-atoms selected from the group consisting of O, N, P and S.

20. The compound according to claim 6, wherein the functional group Q is selected from the group consisting of hydrogen, halogen, $R^{12}$, —CH=C($R^{12}$)$_2$, —C≡C$R^{12}$, —[C($R^{12}$)$_2$C($R^{12}$)$_2$O]$_q$—$R^{12}$, wherein q is in the range of 1 to 200, —CN, —N$_3$, —NCX, —XCN, —X$R^{12}$, —N($R^{12}$)$_2$, —$^+$N($R^{12}$)$_3$, —C(X)N($R^{12}$)$_2$, —C($R^{12}$)$_2$X$R^{12}$, —C(X)$R^{12}$, —C(X)X$R^{12}$, —S(O)$R^{12}$, —S(O)$_2$$R^{12}$, —S(O)O$R^{12}$, —S(O)$_2$O$R^{12}$, —S(O)N($R^{12}$)$_2$, —S(O)$_2$N($R^{12}$)$_2$, —OS(O)$R^{12}$, —OS(O)$_2$$R^{12}$, —OS(O)O$R^{12}$, —OS(O)$_2$O$R^{12}$, —P(O)($R^{12}$)(O$R^{12}$), —P(O)(O$R^{12}$)$_2$, —OP(O)(O$R^{12}$)$_2$, —Si($R^{12}$)$_3$, —XC(X)$R^{12}$, —XC(X)X$R^{12}$, —XC(X)N($R^{12}$)$_2$, —N($R^{12}$)C(X)$R^{12}$, —N($R^{12}$)C(X)X$R^{12}$ and —N($R^{12}$)C(X)N($R^{12}$)$_2$, wherein X is oxygen or sulphur and wherein $R^{12}$ is independently selected from the group consisting of hydrogen, halogen, $C_1$-$C_{24}$ alkyl groups, $C_6$-$C_{24}$ aryl groups, $C_6$-$C_{24}$ heteroaryl groups, $C_7$-$C_{24}$ alkylaryl groups, $C_7$-$C_{24}$ alkylheteroaryl groups, $C_7$-$C_{24}$ arylalkyl groups and $C_7$-$C_{24}$ heteroarylalkyl groups.

21. The compound according to claim 11, wherein the compound comprising a 1,3-dipole, a 1,3-diene or a 1,3-heterodiene is an azide-comprising compound and the azide-alkyne coupling results in the formation of a triazole compound.

* * * * *